United States Patent
Davis et al.

(10) Patent No.: US 10,570,428 B2
(45) Date of Patent: Feb. 25, 2020

(54) VARIANT THIOESTERASES AND METHODS OF USE

(71) Applicant: Corbion Biotech, Inc., South San Francisco, CA (US)

(72) Inventors: David Davis, South San Francisco, CA (US); Scott Franklin, Woodside, CA (US); Jeffrey L. Moseley, Redwood City, CA (US); Riyaz Bhat, South San Francisco, CA (US)

(73) Assignee: CORBION BIOTECH, INC., South San Francisco, CA (US)

( * ) Notice: Subject to any disclaimer, the term of this patent is extended or adjusted under 35 U.S.C. 154(b) by 0 days.

(21) Appl. No.: 16/283,373

(22) Filed: Feb. 22, 2019

(65) Prior Publication Data

US 2019/0249208 A1    Aug. 15, 2019

Related U.S. Application Data

(63) Continuation of application No. 15/684,941, filed on Aug. 24, 2017, now Pat. No. 10,246,728, which is a continuation of application No. 14/808,361, filed on Jul. 24, 2015, now Pat. No. 9,765,368.

(60) Provisional application No. 62/028,641, filed on Jul. 24, 2014.

(51) Int. Cl.
| | | |
|---|---|---|
| *C12N 9/16* | (2006.01) | |
| *C12P 7/64* | (2006.01) | |
| *C12N 15/82* | (2006.01) | |

(52) U.S. Cl.
CPC .............. *C12P 7/6463* (2013.01); *C12N 9/16* (2013.01); *C12N 15/8247* (2013.01); *C12Y 301/02014* (2013.01)

(58) Field of Classification Search
CPC ......... C12N 9/16; C12N 15/8247; C12P 7/64; C12Y 301/02014
See application file for complete search history.

(56) References Cited

U.S. PATENT DOCUMENTS

| | | |
|---|---|---|
| 4,049,724 A | 9/1977 | Sheng et al. |
| 4,288,378 A | 9/1981 | Japikse et al. |
| 4,335,156 A | 6/1982 | Kogan et al. |
| 4,584,139 A | 4/1986 | Gray et al. |
| 4,603,188 A | 7/1986 | Kusakawa et al. |
| 4,683,202 A | 7/1987 | Mullis |
| 4,798,793 A | 1/1989 | Eigtved |
| 4,940,835 A | 7/1990 | Shah et al. |
| 4,940,845 A | 7/1990 | Hirota et al. |
| 4,945,050 A | 7/1990 | Sanford et al. |
| 4,992,189 A | 2/1991 | Chen et al. |
| 5,080,848 A | 1/1992 | Strauss et al. |
| 5,091,116 A | 2/1992 | Krishnamurthy et al. |
| 5,156,963 A | 10/1992 | Eigtved |
| 5,233,099 A | 8/1993 | Tabata |
| 5,233,100 A | 8/1993 | Tabata et al. |
| 5,258,197 A | 11/1993 | Wheeler et al. |
| 5,268,192 A | 12/1993 | Zook et al. |
| 5,298,421 A | 3/1994 | Davies et al. |
| 5,298,637 A | 3/1994 | Cooper |
| 5,304,481 A | 4/1994 | Davies et al. |
| 5,304,664 A | 4/1994 | Peppmoller et al. |
| 5,342,768 A | 8/1994 | Pedersen et al. |
| 5,344,771 A | 9/1994 | Davies et al. |
| 5,346,724 A | 9/1994 | Ohgake et al. |
| 5,380,894 A | 1/1995 | Burg et al. |
| 5,391,383 A | 2/1995 | Sullivan et al. |
| 5,427,704 A | 6/1995 | Lawate |
| 5,434,278 A | 7/1995 | Pelloso et al. |
| 5,451,332 A | 9/1995 | Lawate |
| 5,455,167 A | 10/1995 | Voelker et al. |
| 5,458,795 A | 10/1995 | Lawate |
| 5,475,160 A | 12/1995 | Singleton et al. |
| 5,506,201 A | 4/1996 | McDermott et al. |
| 5,512,482 A | 4/1996 | Voelker et al. |
| 5,567,359 A | 10/1996 | Cassidy et al. |
| 5,576,027 A | 11/1996 | Friedman et al. |
| 5,639,790 A | 6/1997 | Voelker et al. |
| 5,654,495 A | 8/1997 | Voelker et al. |
| 5,667,997 A | 9/1997 | Voelker et al. |
| 5,674,385 A | 10/1997 | Ivaschenko et al. |
| 5,686,131 A | 11/1997 | Sato et al. |
| 5,693,507 A | 12/1997 | Daniell et al. |

(Continued)

FOREIGN PATENT DOCUMENTS

| | | |
|---|---|---|
| CN | 102 066 569 A | 5/2011 |
| CN | 102 300 996 A | 12/2011 |

(Continued)

OTHER PUBLICATIONS

U.S. Office Action, dated Jul. 16, 2015, issued in U.S. Appl. No. 13/797,733.

(Continued)

*Primary Examiner* — Maryam Monshipouri

(74) *Attorney, Agent, or Firm* — Leydig, Voit & Mayer, Ltd.

(57) ABSTRACT

The present invention relates to variant thioesterases and their use in plants, e.g., to increase enzymatic activity and to promote increased production of mid-chain length fatty acids (e.g., 8 to 14 carbons) and at desired ratios. Further disclosed herein are methods of manufacturing renewable chemicals through the manufacture of novel triglyceride oils followed by chemical modification of the oils. Oils containing fatty acid chain lengths of C8, C10, C12 or C14 are also disclosed and are useful as feedstocks in the methods described herein.

20 Claims, 3 Drawing Sheets

Specification includes a Sequence Listing.

(56) References Cited

U.S. PATENT DOCUMENTS

| | | |
|---|---|---|
| 5,723,761 A | 3/1998 | Voelker et al. |
| 5,776,741 A | 7/1998 | Pedersen et al. |
| 5,807,893 A | 9/1998 | Voelker et al. |
| 5,833,999 A | 11/1998 | Trinh et al. |
| 5,850,022 A | 12/1998 | Dehesh et al. |
| 5,885,440 A | 3/1999 | Hoehn et al. |
| 5,888,947 A | 3/1999 | Lambert et al. |
| 5,910,631 A | 6/1999 | Topfer et al. |
| 5,928,696 A | 7/1999 | Best et al. |
| 5,942,479 A | 8/1999 | Frankenbach et al. |
| 5,945,585 A | 8/1999 | Hitz et al. |
| 6,020,509 A | 2/2000 | Weerasooriya et al. |
| 6,022,577 A | 2/2000 | Chrysam et al. |
| 6,027,900 A | 2/2000 | Allnutt et al. |
| 6,051,539 A | 4/2000 | Kodali et al. |
| 6,057,375 A | 5/2000 | Wollenweber et al. |
| 6,080,853 A | 6/2000 | Corrigan et al. |
| 6,086,903 A | 7/2000 | Trinh et al. |
| 6,113,971 A | 9/2000 | Elmaleh |
| 6,140,302 A | 10/2000 | Lueder et al. |
| 6,150,512 A | 11/2000 | Yuan |
| 6,217,746 B1 | 4/2001 | Thakkar et al. |
| 6,268,517 B1 | 7/2001 | Filler et al. |
| 6,278,006 B1 | 8/2001 | Kodali et al. |
| 6,320,101 B1 | 11/2001 | Kaplan et al. |
| 6,331,664 B1 | 12/2001 | Rubin-Wilson et al. |
| 6,342,208 B1 | 1/2002 | Hyldgaard et al. |
| 6,380,410 B1 | 4/2002 | Oftring et al. |
| 6,391,815 B1 | 5/2002 | Weston et al. |
| 6,395,965 B1 | 5/2002 | Xia |
| 6,398,707 B1 | 6/2002 | Wu et al. |
| 6,407,044 B2 | 6/2002 | Dixon |
| 6,465,642 B1 | 10/2002 | Kenneally et al. |
| 6,468,955 B1 | 10/2002 | Smets et al. |
| 6,538,169 B1 | 3/2003 | Pittman et al. |
| 6,590,113 B1 | 7/2003 | Sleeter |
| 6,596,155 B1 | 7/2003 | Gates et al. |
| 6,596,768 B2 | 7/2003 | Block et al. |
| 6,630,066 B2 | 10/2003 | Cash et al. |
| 6,680,426 B2 | 1/2004 | Daniell et al. |
| 6,692,730 B2 | 2/2004 | Perron et al. |
| 6,750,048 B2 | 6/2004 | Ruecker et al. |
| 6,770,104 B2 | 8/2004 | Murphy |
| 6,808,737 B2 | 10/2004 | Ullanoormadam |
| 6,869,597 B2 | 3/2005 | Arnaud |
| 6,881,873 B2 | 4/2005 | Gillespie et al. |
| 6,924,333 B2 | 8/2005 | Bloom et al. |
| 6,946,430 B2 | 9/2005 | Sakai et al. |
| 6,977,322 B2 | 12/2005 | Gillespie |
| 7,041,866 B1 | 5/2006 | Gillespie |
| 7,053,267 B2 | 5/2006 | Knauf et al. |
| 7,081,567 B2 | 7/2006 | Xue et al. |
| 7,115,173 B2 | 10/2006 | Caswell et al. |
| 7,115,760 B2 | 10/2006 | Sparso et al. |
| 7,118,773 B2 | 10/2006 | Floeter et al. |
| 7,135,290 B2 | 11/2006 | Dillon |
| 7,135,620 B2 | 11/2006 | Daniell et al. |
| 7,196,124 B2 | 3/2007 | Parker et al. |
| 7,232,935 B2 | 6/2007 | Jakkula et al. |
| 7,238,277 B2 | 7/2007 | Dahlberg et al. |
| 7,262,158 B1 | 8/2007 | Lukenbach et al. |
| 7,264,886 B2 | 9/2007 | Cui et al. |
| 7,268,276 B2 | 9/2007 | Ruezinksy et al. |
| 7,288,278 B2 | 10/2007 | Mellerup et al. |
| 7,288,685 B2 | 10/2007 | Marker |
| 7,588,931 B2 | 9/2009 | Damude et al. |
| 7,622,570 B2 | 11/2009 | Oswald et al. |
| 8,029,579 B2 | 10/2011 | Knuth et al. |
| 8,530,207 B2 | 9/2013 | Watts et al. |
| 8,956,834 B2 | 2/2015 | Roessler et al. |
| 9,290,749 B2 | 3/2016 | Rudenko et al. |
| 9,567,615 B2 | 2/2017 | Davis |
| 9,765,368 B2 | 9/2017 | Davis et al. |
| 9,783,836 B2 | 10/2017 | Rudenko et al. |
| 9,816,079 B2 | 11/2017 | Davis |
| 9,969,990 B2 | 5/2018 | Davis et al. |
| 10,125,382 B2 | 11/2018 | Casolari et al. |
| 2002/0178467 A1 | 11/2002 | Dehesh |
| 2003/0097686 A1 | 5/2003 | Knauf et al. |
| 2003/0145350 A1 | 7/2003 | Spener et al. |
| 2005/0005333 A1 | 1/2005 | Ruezinsky et al. |
| 2005/0102716 A1 | 5/2005 | Venkatramesh et al. |
| 2005/0262588 A1 | 11/2005 | Dehesh et al. |
| 2007/0175091 A1 | 8/2007 | Danzer et al. |
| 2007/0261138 A1 | 11/2007 | Graham et al. |
| 2009/0176272 A1 | 7/2009 | Champagne et al. |
| 2009/0317878 A1 | 12/2009 | Champagne et al. |
| 2010/0058651 A1 | 3/2010 | Knuth et al. |
| 2010/0105955 A1 | 4/2010 | Alibhai et al. |
| 2010/0151538 A1 | 6/2010 | Franklin et al. |
| 2010/0154293 A1 | 6/2010 | Hom et al. |
| 2011/0072714 A1 | 3/2011 | Gaertner et al. |
| 2011/0145944 A1 | 6/2011 | Laga et al. |
| 2011/0250659 A1 | 10/2011 | Roberts et al. |
| 2011/0293785 A1 | 12/2011 | Franklin |
| 2012/0009636 A1 | 1/2012 | Berry et al. |
| 2012/0283460 A1 | 11/2012 | Franklin et al. |
| 2012/0288930 A1 | 11/2012 | Trimbur et al. |
| 2013/0029387 A1 | 1/2013 | Nikolau et al. |
| 2013/0031678 A1 | 1/2013 | Zheng et al. |
| 2013/0034887 A1 | 2/2013 | Franklin et al. |
| 2013/0219557 A1 | 8/2013 | Tojo et al. |
| 2014/0215654 A1 | 7/2014 | Davis |
| 2014/0234920 A1 | 8/2014 | Davis |
| 2014/0275586 A1 | 9/2014 | Rudenko et al. |
| 2014/0288320 A1 | 9/2014 | Rudenko et al. |
| 2016/0001006 A1 | 1/2016 | Davis et al. |
| 2016/0032332 A1 | 2/2016 | Davis et al. |
| 2016/0083758 A1 | 3/2016 | Cacorbri et al. |
| 2016/0251685 A1 | 9/2016 | Rudenko et al. |
| 2018/0148747 A1 | 5/2018 | Davis et al. |
| 2018/0171312 A1 | 6/2018 | Davis |
| 2018/0208953 A1 | 7/2018 | Rudenko et al. |

FOREIGN PATENT DOCUMENTS

| | | |
|---|---|---|
| CN | 102 459569 A | 5/2012 |
| CN | 102 559 727 A | 7/2012 |
| CN | 102 586 350 A | 7/2012 |
| EP | 1 605 048 A1 | 12/2005 |
| EP | 1 640 437 A1 | 3/2006 |
| EP | 1 681 337 A1 | 7/2006 |
| EP | 1 741 767 A1 | 1/2007 |
| EP | 1 741 768 A1 | 1/2007 |
| EP | 1 795 576 A1 | 6/2007 |
| EP | 1 682 466 B1 | 11/2008 |
| JP | 11-505115 A | 5/1999 |
| JP | 2012-510275 A | 5/2012 |
| WO | WO 89/01032 A1 | 2/1989 |
| WO | WO 92/11373 A1 | 7/1992 |
| WO | WO 92/020236 | 11/1992 |
| WO | WO 92/20636 A1 | 11/1992 |
| WO | WO 94/10288 A2 | 5/1994 |
| WO | WO 95/06740 | 3/1995 |
| WO | WO 95/13390 A2 | 5/1995 |
| WO | WO 96/23892 A2 | 8/1996 |
| WO | WO 96/36719 A1 | 11/1996 |
| WO | WO 98/55633 A1 | 12/1998 |
| WO | WO 00/61740 A1 | 10/2000 |
| WO | WO 00/66750 A2 | 11/2000 |
| WO | WO 02/08403 A2 | 1/2002 |
| WO | WO 2005/047216 A1 | 5/2005 |
| WO | WO 2006/055322 A2 | 5/2006 |
| WO | WO 2007/106903 A2 | 9/2007 |
| WO | WO 2008/002643 A2 | 1/2008 |
| WO | WO 2008/151149 A2 | 12/2008 |
| WO | WO 2010/019813 A2 | 2/2010 |
| WO | WO 2010/063031 A2 | 6/2010 |
| WO | WO 2010/063032 A2 | 6/2010 |
| WO | WO 2010/120939 A2 | 10/2010 |
| WO | WO 2011/003034 A2 | 1/2011 |
| WO | WO 2011/008565 A1 | 1/2011 |
| WO | WO 2011/127069 A1 | 10/2011 |
| WO | WO 2011/150410 A2 | 12/2011 |

(56) References Cited

FOREIGN PATENT DOCUMENTS

| | | |
|---|---|---|
| WO | WO 2011/150411 A1 | 12/2011 |
| WO | WO 2012/061647 A2 | 5/2012 |
| WO | WO 2012/106560 A1 | 8/2012 |
| WO | WO 2012/154626 A1 | 11/2012 |
| WO | WO 2013/158938 A1 | 10/2013 |
| WO | WO 2014/120829 A1 | 8/2014 |
| WO | WO 2014/151904 A1 | 9/2014 |
| WO | WO 2015/051319 A2 | 4/2015 |
| WO | PCT/US2015/42044 | 7/2015 |
| WO | WO 2016/007862 | 1/2016 |
| WO | WO 2016/014968 A1 | 1/2016 |
| WO | WO 2016/044779 A2 | 3/2016 |

OTHER PUBLICATIONS

U.S. Final Office Action, dated Dec. 14, 2015, issued in U.S. Appl. No. 13/797,733.
U.S. Office Action, dated Jul. 26, 2016, issued in U.S. Appl. No. 13/797,733.
U.S. Notice of Allowance, dated Sep. 21, 2016, issued in U.S. Appl. No. 13/797,733.
U.S. Office Action (Requirement for Restriction/Election), dated Jul. 12, 2016, issued in U.S. Appl. No. 14/167,908.
U.S. Office Action, dated Apr. 3, 2017, issued in U.S. Appl. No. 14/167,908.
U.S. Office Action, dated Jul. 22, 2015, issued in U.S. Appl. No. 13/837,996.
U.S. Notice of Allowance, dated Nov. 17, 2015, issued in U.S. Appl. No. 13/837,996.
U.S. Office Action (Requirement for Restriction/Election), dated Jul. 12, 2016, issued in U.S. Appl. No. 14/209,931.
U.S. Office Action, dated Jan. 26, 2017, issued in U.S. Appl. No. 14/209,931.
PCT International Search Report and Written Opinion dated Jun. 24, 2014 issued in PCT/US2014/013676.
PCT International Preliminary Report on Patentability and Written Opinion dated Aug. 13, 2015 issued in PCT/US2014/013676.
Database Geneseq [Online] (Jun. 6, 2000) "Bay C18:1 preferring acyl-ACP thioesterase protein from clone 3A-17.", retrieved from EBI accession No. GSP:AAY80558 Database accession No. AAY80558; and Database Geneseq [Online] (Jun. 6, 2000) "Bay C18:1 preferring acyl-ACP thioesterase protein.", retrieved from EBI accession No. GSP:AAY80559 Database accession No. AAY80559.
Database Geneseq [Online] (Nov. 2, 1995) "Camphor thioesterase.", retrieved from EBI accession No. GSP:AAR74148 Database accession No. AAR74148.
Database Geneseq [Online] (Oct. 26, 1996) "Cuphea C14:0-ACP thioesterase.", retrieved from EBI accession No. GSP:AAW02081 Database accession No. AAW02081.
Database Geneseq [Online] (Aug. 5, 2010) "U. californica fatty acyl-ACP thioesterase protein (without PTS), SEQ:139.", retrieved from EBI accession No. GSP:AYC84249 Database accession No. AYC84249.
European Examination Report dated Oct. 25, 2016 issued in EP 14 706 996.7.
Mexican Office Action [no translation] dated Sep. 21, 2015 issued in MX/a/2015/009730.
PCT Invitation To Pay Additional Fees And, Where Applicable, Protest Fee dated Jun. 18, 2014 issued in PCT/US2014/026644.
PCT International Search Report and Written Opinion dated Aug. 29, 2014 issued in PCT/US2014/026644.
PCT International Preliminary Report on Patentability dated Sep. 24, 2015 issued in PCT/US2014/026644.
Genbank Accession No. U17097, Umbellularia californica UC FatB2 (FatB) mRNA, complete cds., Jun. 1, 1995, 2pp.
Genbank: Accession No. U39834.1, Cuphea hookeriana 8:0- and 10:0-ACP specific thioesterase (FatB2) mRNA, complete cds, May 21, 2014, 2pp.
Genbank Accession No. AAC49001, UC FatB2 (FatB) Umbellularica californica, May 30, 1995, 2pp.
European Partial Supplementary Search Report (Communication pursuant to Rule 164(1)EPC) dated Jul. 6, 2016 issued in EP 14 76 9502.7.
European Extended Search Report dated Oct. 13, 2016 issued in EP 14 76 9502.7.
PCT International Search Report and Written Opinion dated Dec. 22, 2015 issued in PCT/US2015/042044.
PCT International Preliminary Report on Patentability dated Feb. 2, 2017 issued in PCT/US2015/042044.
Database UniProt [Online] (Jul. 24, 2013) "SubName: Full =FatB type acyl-ACP thioesterase-3 {EC0:0000313:EMBL:AGG79285.1}," retrieved on Nov. 10, 2015 from EBI accession No. UNIPROT:R4J2L6, Database accession No. R4J2L6 sequence, 1 page.
Database UniProt [Online] (Jul. 9, 2014) "SubName: Full= Uncharacterized protein {EC0:0000313:EMBL:KCW58039.1}," retrieved on Nov. 16, 2015 from EBI accession No. UNIPROT:A0A059AWB4, Database accession No. A0A059AWB4 sequence, 1 page.
PCT Invitation To Pay Additional Fees And, Where Applicable, Protest Fee dated Jan. 13, 2016 issued in PCT/US2015/051042.
PCT International Search Report and Written Opinion dated Mar. 31, 2016 issued in PCT/US2015/051042.
Apt et al., (1996) "Stable nuclear transformation of the diatom *Phaeodactylum tricornutum,*" *Molecular and General Genetics*, 252:572-579.
Barnes et al., (2005) "Contribution of 5'- and 3'-untranslated regions of plastid mRNAs to the expression of *Chlamydomonas reinhardtii* chloroplast genes," *Mol Gen Genomics* 274:625-636.
Blatti et al., (Sep. 2012) "Manipulating Fatty Acid Biosynthesis in Microalgae for Biofuel through Protein-Protein Interactions," *PLoS ONE* 7(9):e42949, 12pp.
Blowers et al., (Jan. 1989) "Studies on *Chlamydomonas* Chloroplast Transformation: Foreign DNA Can Be Stably Maintained in the Chromosome," *The Plant Cell*, 1:123-132.
Bonaventure et al., (Apr. 2003) "Disruption of the FATB Gene in *Arabidopsis dethonstrates* an Essential Role of Saturated Fatty Acids in Plant Growth," *The Plant Cell* 15:1020-1033.
Boynton et al., (1988) "Chloroplast Transformation in *Chlamydomonas* with High Velocity Microprojectiles," *Science*, 240(4858):1534-1538.
Chasan, (Mar. 1995) "Engineering Fatty Acids—The Long and Short of It," *Plant Cell*, 7:235-237.
Chen et al., (1988) "Recognition of prokaryotic transcription terminators by spinach chloroplast RNA polymerase," *Nucleic Acids Research*, 16(17):8411-8431.
Chen et al., (2001) "Highly efficient expression of rabbit neutrophil peptide-1 gene in *Chlorella ellipsoidea* cells," *Current Genetics*, 39(5):365-370.
Chow et al., (1999) "Electrotransformation of *Chlorella vulgaris,*" *Plant Cell Reports*, 18:778-780.
Cobley et al., (Sep. 1993) "Construction of Shuttle Plasmids Which Can Be Efficiently Mobilzed from *Escherichia coli* into the Chromatically Adapting Cyanobacterium, *Fremyella diplosiphon,*" *Plasmid*, 30(2): 90-105.
Cobley et al., (2002) "CpeR is an activator required for expression of the phycoerythrin operon (cpeBA) in the cyanobacterium Fremyella diplosiphon and is encoded in the phycoerythrin linker-polypeptide operon (cpeCDESTR)," *Molecular Microbiololgy*, 44(6): 1517-1531.
Comai et al., (Oct. 15, 1988) "Chloroplast Transport of a Ribulose Bisphosphate Carboxylase Small Subunit-5-Enolpyruvyl 3-Phosphoshikimate Synthase Chimeric Protein Requires Part of the Mature Small Subunit in Addition to the Transit Peptide," *The Journal of Biological Chemistry*, 263(29): 15104-15109.
Courchesne, Noémie Manuelle Dorval el al., (2009) "Enhancement of lipid production using biochemical, genetic and transcription factor engineering approaches," *Journal of Biotechnology*, 141(1):31-41.

(56) References Cited

OTHER PUBLICATIONS

Davies et al., (1992) "Expression of the arylsulfatase gene from the β₂-tubulin promoter in Chlamydomonas reinhardtii," Nucleic Acids Res., 20(12):2959-2965.
Dawson et al.,(1997) "Stable Transformation of Chlorella: Rescue of Nitrate Reductase-Deficient Mutants with the Nitrate Reductase Gene," Current Microbiol., 35(6):356-362.
Debuchy et al.,(1989) "The argininosuccinate lyase gene of Chlamydomonas reinhardtii: an important tool for nuclear transformation and for correlating the genetic and molecular maps of the ARG7 locus," EMBO Journal, 8(10):2803-2809.
Dehesh et al. (1996) "Production of high levels of 8:0 and 10:0 fatty acids in transgenic canola by overexpression of Ch FatB2, a thioesterase cDNA from Cuphea hookeriana," The Plant Journal, 9(2): 167-172.
Dehesh et al., (1998) "KAS IV: a 3-ketoacyl-ACO synthase from Cuphea sp. is a medium chain specific condensing enzyme," The Plant Journal, 15:383-390.
Deshnium et al., (1995) "Transformation of Synechococcus with a gene for choline oxidase enhances tolerance to salt stress," Plant Mol. Biol.,29(5):897-907.
Dörmann et al., (Jan. 1995) "Cloning and Expression in Escherichia coli of a Novel Thioesterase from Arabidopsis thaliana Specific for Long-Chain Acyl-Acyl Carrier Proteins," Archives of Biochemistry and Biophysics, 316(1):612-618.
Dubois et al., (2007) "Fatty acid profiles of 80 vegetable oils with regard to their nutritional potential," Eur. J. Lipid Sci. Technol., 109:710-732.
Eccleston et al., (1996) "Medium-chain fatty Acid biosynthesis and utilization in Brassica napus plants expressing lauroyl-acyl carrier protein thioesterase," Planta, 198:46-53.
El-Sheekh et al., (1999) "Stable transformation of the intact cells of Chlorella kessleri with high velocity microprojectiles," Biologia Plantarium, 42:(2):209-216.
Facciotti et al., (1998) "Molecular dissection of the plant acyl-acyl carrier protein thioesterases," Fett/Lipid, 100(4-5, S.):167-172.
Facciotti et al., (Jun. 1, 1999) "Improved stearate phenotype in transgenic canola expressing a modified acyl-acyl carrier protein thioesterase," Nat Biotechnol., 17(6):593-597.
Falciatore et al., (May 1999) "Transformation of Nonselectable Reporter Genes in Marine Diatoms," Mar. Biotechnol., 1(3):239-251.
Frenz et al., (1989) "Hydrocarbon recovery by extraction with a biocompatible solvent from free and immobilized cultures of Botryococcus braunii," Enzyme Microb. Technol., 11:717-724.
Fromm et al., (Sep. 1985) "Expression of genes transferred into monocot and dicot plant cells by electroporation," Proc. Natl. Acad. Sci. USA, 82:5824 5828.
Ginalski et al., (2003) "Detection of reliable and unexpected protein fold predictions using 3D-Jury," Nucleic Acids Research,31(13): 3291-3292.
Giuffrida et al., (2004) "Formation and Hydrolysis of Triacylglycerol and Sterol Epdxides: Role of Unsaturated Triacylglycerol Peroxyl Radicals," Free Radical Biology and & Medicine, 37(1):104-114.
Gruber et al., (1991) "Escherichia coli-Anacystis nidulans Plasmid Shuttle Vectors Containing the P_L Promoter from Bacteriophage Lambda," Current Micro. 22:15-19.
Gruber et al., (1996) "Expression of the Volvox gene encoding nitrate reductase: Mutation-dependent activation of cryptic splice sites and intron-enhanced gene expression from a cDNA," Plant Molecular Biology, 31(1):1-12.
Guo et al. (Jun. 22, 2004) "Protein tolerance to random amino acid change," Proc. Natl. Acad. Sci. USA, 101(25):9205-9210.
Hall et al., (1993) "Expression of a foreign gene in Chlamydomonas reinhardtii," Gene, 124:75-81.
Hallmann et al., (Nov. 1994) "Reporter genes and highly regulated promoters as tools for transformation experiments in Volvox carteri," Proc. Natl. Acad. Sci. USA, 91:11562-11566.
Hanley-Bowdoin et al., (Feb. 1987) "Chloroplast promoters," TIBS, 12:67-70.
Hawkins et al., (1999) "Expression of Human Growth Hormone by the Eukaryotic Alga, Chlorella," Current Microbiology, 38:335-341.
Heise et al., (1994) "Factors Controlling Medium-Chain Fatty Acid Synthesis in Plastids From Cuphea Embryos," Prog. Lipid Res., 33(1/2):87-95.
Hejazi et al., (Apr. 2004) "Milking of microalgae," TRENDS in Biotechnology, 22(4): 189-194.
Hill et al., (1998) "Functional Analysis of Conserved Histidines in ADP-Glucose Pyrophosphorylase from Escherichia coli," Biochem. Biophys. Res. Comm., 244(2):573-577.
Hillen et al., (1982) "Hydrocracking of the Oils of Botryococcus braunii to Transport Fuels," Biotechnology and Bioengineering, XXIV:193-205.
Hitz et al., (1994) "Cloning of a Higher-Plant Plastid ω-6 Fatty Acid Desaturase cDNA and Its Expression in a Cyanobacterium," Plant Physiol.,105(2):635-641.
Huang et al. (2006) "Expression of mercuric reductase from Bacillus megaterium MB1 in eukaryotic microalga Chlorella sp. DT: an approach for mercury phytoremediation,"Appl. Microbiol. Biotechnol. 72:197-205.
Inoue et al., (1994) "Analysis of Oil Derived From Liquefaction of Botryococcus braunii," Biomass Bioenergy, 6(4):269-274).
Isbell et al., (Feb. 1994) "Acid-Catalyzed Condensation of Oleic Acid into Estolides and Polyestolides," JAOCS, 71(2):169-174.
Jakobiak et al. (Dec. 2004) "The Bacterial Paromomycin Resistance Gene, aphH, as a Dominant Selectable Marker in Volvox carteri," Protist, 155(4):381-393.
Jarvis et al.(1991) "Transient expression of firefly luciferase in protoplasts of the green alga Chlorella ellipsoidea," Current Genetics, 19:317-321.
Jha et al., (2006) "Cloning and functional expression of an acyl-ACP thioesterase FatB type from Diploknema (Madhuca) butyracea seeds in Escherichia coli," Plant Physiology and Biochemistry, 44:645-655.
Jiang et al., (Apr. 2005) "The Actin Gene Promoter-driven bar as a Dominant Selectable Marker for Nuclear Transformation of Dunaliella salina," Acta Genetica Sinica, 32(4):424-433.
Jones et al., (Mar. 1995) "Palmitoyl-Acyl Carrier Protein (ACP) Thioesterase and the Evolutionary Origin of Plant Acyl-ACP Thioesterases," The Plant Cell, 7:359-371.
Kalscheuer et al., (1999) "Establishment of a gene transfer system for Rhodococcus opacus PD630 based on electroporation and its application for recombinant biosynthesis of poly(3-hydroxyalkanoic acids)," Applied and Environmental Microbiology, 52:508-515.
Kang et al., (Jul. 2000) "The Regulation Activity of Chlorella Virus Gene 5' Upstream Sequence in Escherichia coli and Eucaryotic Algae," [English Abstract] Chinese Journal of Biotechnology, 16(4):6 pages.
Kang et al., (2004) "Genetic diversity in chlorella viruses flanking kcv, a gene that encodes a potassium ion channel protein," Virology, 326(1):150-159.
Kawasaki et al., (2004) "Immediate early genes expressed in chlorovirus infections," Virology, 318(1):214-223.
Kim et al., (2002) Stable Integration and Functional Expression of Flounder Growth Hormone Gene in Transformed Microalga, Chlorella ellipsoidea, Mar. Biotechnol., 4(1):63-73.
Kindle, (Feb. 1990) "High-frequency nuclear transformation of Chlamydomonas reinhardtii," Proc. Natl. Acad. Sci. USA, 87(3): 1228-1232.
Klein et al., (1987) "High-velocity microprojectiles for delivering nucleic acids into living cells," Nature London 327(7):70-73.
Knauf, (Feb. 1987) "The application of genetic engineering to oilseed crops," TIBTECH, 5:40-47.
Knutzon et al., (Jul. 1999) "Lysophosphatidic Acid Acyltransferase from Coconut Endosperm Mediates the Insertion of Laurate at the sn-2 Position of Triacylglycerols in Lauric Rapeseed Oil and Can Increase Total Laurate Levels," Plant Physiology, 120:739-746.
Kojima et al., (1999) "Growth and Hydrocarbon Production of Microalga Botryococcus braunii in Bubble Column Photobioreactors," Journal of Bioscience and Bioengineering, 87(6):811-815.
Koksharova et al., (Feb. 2002) "Genetic tools for cyanobacteria," Appl Microbiol Biotechnol 58(2):123-137.

(56) References Cited

OTHER PUBLICATIONS

Krebbers et al., (1982) "The maize chloroplast genes for the β and ε subunits of the photosynthetic coupling factor $CF_1$ are fused," *Nucleic Acids Research*, 10(16):4985-5002.

La Scala et al., (Jan. 2002) "The Effect of Fatty Acid Composition on the Acrylation Kinetics of Epoxidized Triacylglycerols", *Journal of the American Oil Chemists' Society*, 79(1):59-63.

Lapidot et al., (May 2002) "Stable Chloroplast Transformation of the Unicellular Red Alga *Porphyridium* Species," *Plant Physiol.*, 129(1):7-12.

Larson et al., (2002) "Acyl CoA profilesof transgenic plants that accumulate medium-chain fatty acids indicate inefficient storage lipid synthesis in developing oilseeds," *The Plant Journal*, 32(4):519-527.

Lumbreras et al., (1998) "Efficient foreign gene expression in *Chlamydomonas reinhardtii* mediated by an endogenous intron," *Plant Journal*, 14(4):441-447.

Manuell et al., (2007) "Robust expression of a bioactive mammalian protein in *Chlamydomonas* chloroplast," *Plant Biotechnol Journal*, 5:402-412.

Mayer et al., (Feb. 4, 2005) "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," *The Journal of Biological Chemistry*, 280(5):3621-3627.

Mayer et al., (Jan. 3, 2007) "Identification of amino acid residues involved in substrate specificity of plant acyl-ACP thioesterases using a bioinformatics-guided approach," *BMC Plant Biology*, 7(1):1-11 pages.

Mayfield et al., (Jan. 21, 2003) "Expression and assembly of a fully active antibody in algae," *Proc. Natl. Acad. Sci. USA*, 100(2):438-442.

Mekhedov et al., (Feb. 2000) "Toward a Functional Catalog of the Plant Genome. A Survey of Genes for Lipid Biosynthesis," *Plant Physiology*, 122:389-401.

Mendes et al. (2003) "Supercritical carbon dioxide extraction of compounds with pharmaceutical importance from microalgae," *Inorganica Chimica Acta*, 356:328-334.

Metzger et al., (Jun. 2003) "Lycopanerols I-L, Four New Tetraterpenoid Ethers from *Botryococcus braunii*," *J Nat. Prod.* 66(6):772-778.

Metzger et al., (2005) "*Botryococcus braunii*: a rich source for hydrocarbons and related ether lipids," *Appl Microbiol Biotechnol* 66:486-496.

Miao et al., (2004) "High yield bio-oil production from fast pyrolysis by metabolic controlling of *Chlorella prototheocoides*," *Journal of Biotechnology*, 110:85-93.

Miao et al., (2006) "Biodiesel production from heterotrophic microalgal oil," *Biosource Technology*, 97:841-846.

Minowa et al., (1995) "Oil production from algal cells of *Dunaliella tertiolecta* by direct thermochemical liquefaction," *Fuel*, 74(12):1735-1738.

Mitra et al., (Oct. 14, 1994) "A Chlorella Virus Gene Promoter Functions as a Strong Promoter Both in Plants and Bacteria," *Biochemical Biophysical Research Communication*, 204(1): 187-194.

Mitra et al., (Oct. 1994) "The *Chlorella* virus adenine methyltransferase gene promoter is a strong promoter in plants," *Plant Mol. Biol.*, 26(1):85-93.

Mittendorf et al., (1999) "Polyhydroxyalkanoate synthesis in transgenic plants as a new tool to study carbon flow through β-oxidation," *The Plant Journal*, 20(1):45-55.

Moreno-Pérez et al., (2012) "Reduced expression of FatA thioesterases in *Arabidopsis* affects the oil content and fatty acid composition of the seeds," *Planta*, 235:629-639.

Mullet et al., (1985) "Multiple transcripts for higher plant rbcL and atpB genes and localization of the transcription initiation site of the rbcL gene," *Plant Molecular Biology*, 4:39-54.

Oda et al., (2000) "Degradation of Polylactide by Commercial Proteases," *Journal of Polymers and the Environment*, 8(1):29-32.

Onai et al., (2004) "Natural transformation of the thermophilic cyanobacterium *Thermosynechococcus elongatus* BP-1: a simple and efficient method for gene transfer," *Mol Genet Genomics*, 271(1):50-59.

Park et al., (2005) "ICORBtion and Characterization of Chlorella Virus from Fresh Water in Korea and Application in Chlorella Transformation System," The Plant Patholology Journal, 21(1):13-20.

Pröschold et al., (Aug. 2005) "Portrait of a species: *Chlamydomonas reinhardtii*," *Genetics*, 170:1601-1610.

Radakovits et al., (Apr. 2010) "Genetic Engineering of Algae for Enhanced Biofuel Production," *Eukaryotic Cell*, 9(4):486-501.

Rao et al., (2006) "Antioxidant Activity of *Botryococcus braunii* Extract Elucidated in Vitro Models," *J. Agric. Food Chem.*, 54(13):4593-4599.

Rehm et al., (2001)"Heterologous expression of the acyl-acyl carrier protein thioesterase gene from the plant *Umbellularia califomica* mediates polyhydroxyalkanoate biosynthesis in recombinant *Escherichia coli*," *Appl Microbiol Biotechnol*, 55:205-209.

Rismani-Yazdi et al., (2011) "Transcriptome sequencing and annotation of the microalgae *Dunaliella tertiolecta*: Pathway description and gene discovery for production of next-generation biofuels," *BMC Genomics*, 12:148, 17 pages; doi:10.1186/1471-2164-12-148.

Rosenberg, Julian N. et al., (2008) "A green light for engineered algae: redirecting metabolism to fuel a biotechnology revolution," *Current Opinion in Biotechnology*, 19(5):430-436.

Salas et al., (Jul. 1, 2002) "Characterization of substrate specificity of plant FatA and FatB acyl-ACP thioesterases," *Archives of Biochemistry and Biophysics*, 403(1):25-34.

Sanford, (Dec. 1988) "The biolistic process," *Trends In Biotech.* 6:299-302.

Sawayama et al. (1999) Possibility of renewable energy production and $CO_2$ mitigation by thermochemical liquefaction of microalgae *Biomass and Bioenergy*, 17:33-39.

Schreier et al., (1985) "The use of nuclear-encoded sequences to direct the light-regulated synthesis and transport of a foreign protein into plant chloroplasts," *EMBO J.* 4(1):25-32.

Schultz et al., (Apr. 2005) "A common core of secondary structure of the internal transcribed spacer 2 (ITS2) throughout the Eukaryota," *RNA*, 11(4):361-364.

Schütt et al., (1998) "The role of acyl carrier protein isoforms from *Cuphea lanceolata* seeds in the de-novo biosynthesis of medium-chain fatty acids," *Publication, Planta*, 205:263-268.

Shao et al., (2002) "Cloning and expression of metallothionein mutant α-KKS-α in *Anabaena* sp. PCC 7120," *Marine Pollution Bulletin*,45(1-12):163-167.

Sheehan, John; Dunahay, Terri; Benemann, John; Roessler, Paul; (Jul. 1998) "A Look Back at the U.S. Department of Energy's Aquatic Species Program: Biodiesel from Algae," Prepared for U.S. Department of Energy's Office of Fuels Development, Prepared by *National Renewable Energy Laboratory*, NREL/TP-580-24190, 328 pages.

Stemmer et al., (1995) "Single-step assembly of a gene and entire plasmid from large numbers of oligodeoxyribonucleotides," *Gene*, 164(1):49-53.

Tan et al., (Aug. 2005) "Establishment of a Micro-Particle Bombardment Transformation System for *Dunaliella salina*," *The Journal of Microbiology*, 43(4):361-365.

Tang etal., (Aug. 1995) "Insertion Mutagenesis of *Chlamydomonas reinhardtii* by Electroporation and Heterologous DNA," *Biochemistry and Molecular Biology International*, 36(5): 1025-1035.

Tjellström et al., (Feb. 20, 2013) "Disruption of plastid acyl:acyl carrier protein synthetases increases medium chain fatty acid accumulation in seeds of transgenic *Arabidopsis*," *FEBS Letters*,587(7):936-942.

Tyystjärvi et al., (2005) "Mathematical modelling of the light response curve of photoinhibition of Photosystem II," *Photosynthesis Research*, 84(1-3):21-27.

Vázquez-Bermúdez et al., (Jan. 2000) "Uptake of 2-Oxoglutarate in *Synechococcus* Strains Transformed with the *Escherichia coli* kgtP Gene," *Journal of Bacteriology*, 182(1):211-215.

(56) References Cited

OTHER PUBLICATIONS

Vázquez-Bermúdez et al., (2003) "Carbon supply and 2-oxoglutarate elects on expression of nitrate reductase and nitrogen-regulated genes in *Synechococcus* sp. strain PCC 7942," *FEMS Microbiology Letters*, 221(2):155-159.
Voelker, (1996) "Plant Acyl-ACP Thioesterases: Chain-Length Determining Enzymes in Plant Fatty Acid Biosynthesis," *Genetic Engineering*, Edited by: Setlow JK. Plenum Pres, New York, 18:111-133.
Voelker et al., (Dec. 1994) "Alteration of the Specificity and Regulation of Fatty Acid Synthesis of *Escherichia coli* by Expression of a Plant Medium Chain Acyl-Acyl Carrier Protein Thioesterase," *Journal of Bacteriology*, 176(23):7320-7327.
Voelker et al., (1997) "Broad-Range and Binary-Range Acyl-Acyl-Carrier-Protein Thioesterases Suggest an Alternative Mechanism for Medium-Chain Production in Seeds," *Plant Physiol.*, 114:669-677.
Voetz et al., (1994) "Three Different cDNAs Encoding Acyl Carrier Proteins from *Cuphea lanceolata*," *Plant Physiol.*, 106:785-786.
Walker et al., (2005) "Characterisation of the *Dunaliella tertiolecta* RbcS genes and their promoter activity in *Chlamydomonas reinhardtii*," *Plant Cell Rep.* 23(10-11):727-735.
Westphal et al., (Mar. 27, 2001) "Vipp1 deletion mutant of *Synechocystis*: A connection between bacterial phage shock and thylakoid biogenesis?" *Proc. Natl. Acad. Sci. USA*, 98(7):4243-4248.
Wiberg et al., (2000) "The distribution of caprylate, caprate and laurate in lipids from developing and mature seeds of transgenic *Brassica napus* L.," *Planta*, 212:33-40.
Wirth et al., (1989) "Transformation of various species of gram-negative bacteria belonging to 11 different genera by electroporation," *Mol Gen Genet.* 216(1):175-177.
Wolk et al., (Mar. 1984) "Construction of shuttle vectors capable of conjugative transfer from *Escherichia coli* to nitrogen-fixing filamentous cyanobacteria," *Proc. Natl. Acad. Sci. USA*, 81(5):1561-1565.
Wong et al., (1992) "*Arabidopsis thaliana* small subunit leader and transit peptide enhance the expression of *Bacillus thuringiensis* proteins in transgenic plants," *Plant Molecular Biology*, 20:81-93.
Wu et al., (2001) "Identification of *Chlorella* spp. iCORBtes using ribosomal DNA sequences," *Bot. Bull. Acad. Sin.*42:115-121.
Yu et al., (2011) "Modifications of the metabolic pathways of lipid and triacylglycerol production in microalgae," *Microbial Cell Factories*, 10:91 [Retrieved from the Internet Jul. 24, 2012: <URL:http://www.microbialcellfactories.com/content/10/1/91>], 11 pages.
Yuan et al., (Nov. 1995) "Modification of the substrate specificity of an acyl-acyl carrier protein thioesterase by protein engineering," *Proc. Natl. Acad. Sci. USA*, 92:10639-10643.
Yuan et al., (Feb. 16, 1996) "The Catalytic Cysteine and Histidine in the Plant Acyl-Acyl Carrier Protein Thioesterases," *The Journal of Biological Chemistry*, 271(7):3417-3419.
Zurawski et al., (1981) "The structure of the gene for the large subunit of ribulose 1,5-bisphosphate carboxylase from spinach chloroplast DNA," *Nucleic Acids Res.* 9(14):3251-3270.
Zurawski et al., (Dec. 1982) "Nucleotide sequence of the gene for the $M_r$ 32,000 thylakoid membrane protein from *Spinacia oleracea* and *Nicotiana debneyi* predicts a totally conserved primary translation product of $M_r$ 38,950," *Proc. Natl. Acad. Sci. USA*, 79:7699-7703.
U.S. Notice of Allowance, dated Jul. 10, 2017, issued in U.S. Appl. No. 14/167,908.
U.S. Notice of Allowance, dated Aug. 4, 2017 issued in U.S. Appl. No. 14/167,908.
U.S. Notice of Allowance, dated May 15, 2017, issued in U.S. Appl. No. 14/209,931.
U.S. Notice of Allowance, dated Jun. 14, 2017, issued in U.S. Appl. No. 14/209,931.
U.S. Office Action, dated May 25, 2018, issued in U.S. Appl. No. 15/062,045.
U.S. Office Action, dated Jan. 19, 2017, issued in U.S. Appl. No. 14/808,361.
U.S. Notice of Allowance, dated Apr. 28, 2017, issued in U.S. Appl. No 14/808,361.
U.S. Office Action, dated May 31, 2018, issued in U.S. Appl. No. 15/684,941.
U.S. Office Action (Requirement for Restriction/Election), dated Jun. 8, 2017, issued in U.S. Appl. No. 14/858,527.
U.S. Office Action dated Oct. 18, 2017 issued in U.S. Appl. No. 14/858,527.
U.S. Notice of Allowance dated Apr. 6, 2018 issued in U.S. Appl. No. 14/858,527.
U.S. Notice of Allowance dated Jun. 29, 2018 issued in U.S. Appl. No. 14/858,527.
Database Geneseq [Online] Jun. 15, 2007 (Jun. 15, 2007), "Medium chain-specific acyl-(ACP)-thioesterase CITEG1.", retrieved from EBI accession No. GSP:AAW06703 Database accession No. AAW06703.
Brazilian First Office Action dated Mar. 7, 2018 issued in Application No. BR 1120150179207.
Chinese First Office Action dated Jun. 13, 2017 issued in CN 201480018889.4.
Chinese Second Office Action dated Mar. 5, 2018 issued in CN 201480018889.4.
European Second Office Action dated Jan. 4, 2018 issued in EP 14 706 996.7.
Japanese First Office Action dated Mar. 29, 2018 issued in JP 2015-555436.
Mexican Second Office Action dated Jun. 28, 2018 issued in MX/a/2015/009730.
Malaysia Modified Substantive Examination Clear Report dated Sep. 28, 2018 issued in MY PI2015001876.
Australian First Office Action dated Aug. 14, 2017 issued in AU 2014236763.
Australian Second Office Action dated Jun. 12, 2018 issued in AU 2014236763.
Australian Third Office Action dated Aug. 1, 2018 issued in AU 2014236763.
European First Office Action dated Jul. 11, 2017 issued in EP 14769502.7.
European Second Office Action [Examiner's Report] dated Mar. 5, 2018 issued in EP 14769502.7.
European First Office Action dated Jan. 4, 2018 issued in EP 15747911.4.
Mexican First Office Action dated Jan. 26, 2018 issued in MX MX/a/2015/011507.
Mexican Second Office Action dated Jun. 15, 2018 issued in MX MX/a/2015/011507.
Chinese First Office Action dated Apr. 23, 2018 issued in CN 201480020002.5.
PCT International Preliminary Report on Patentability dated Mar. 30, 2017 issued in PCT/US2015/051042.
European First Office Action dated Jun. 8, 2018 issued in EP 15775855.8.
Brandt, et al. (1993) "Gametic Selection at Fatty Acid and Allozyme Marker Loci and Meiosis within Cuphea *viscosissima* x Cuphea *lanceolata* Populations," Crop Science, vol. 33, pp. 1138-1143.
Jing et al., (2011) "Phylogenetic and experimental characterization of an acyl-ACP thioesterase family reveals significant diverstiy in enzymatic specificity and activity," BMC Biochemistry, Aug. 27, 2011, vol. 12.1, No. 44, pp. 1-16.
Leonard et al., (1997) "Cuphea wrightii thioesterases have unexpected broad specificities on saturated fatty acids," Plant Molecular Biology, vol. 34, pp. 669-679.
U.S. Notice of Allowance, dated Nov. 15, 2018, issued in U.S. Appl. No. 15/684,941.

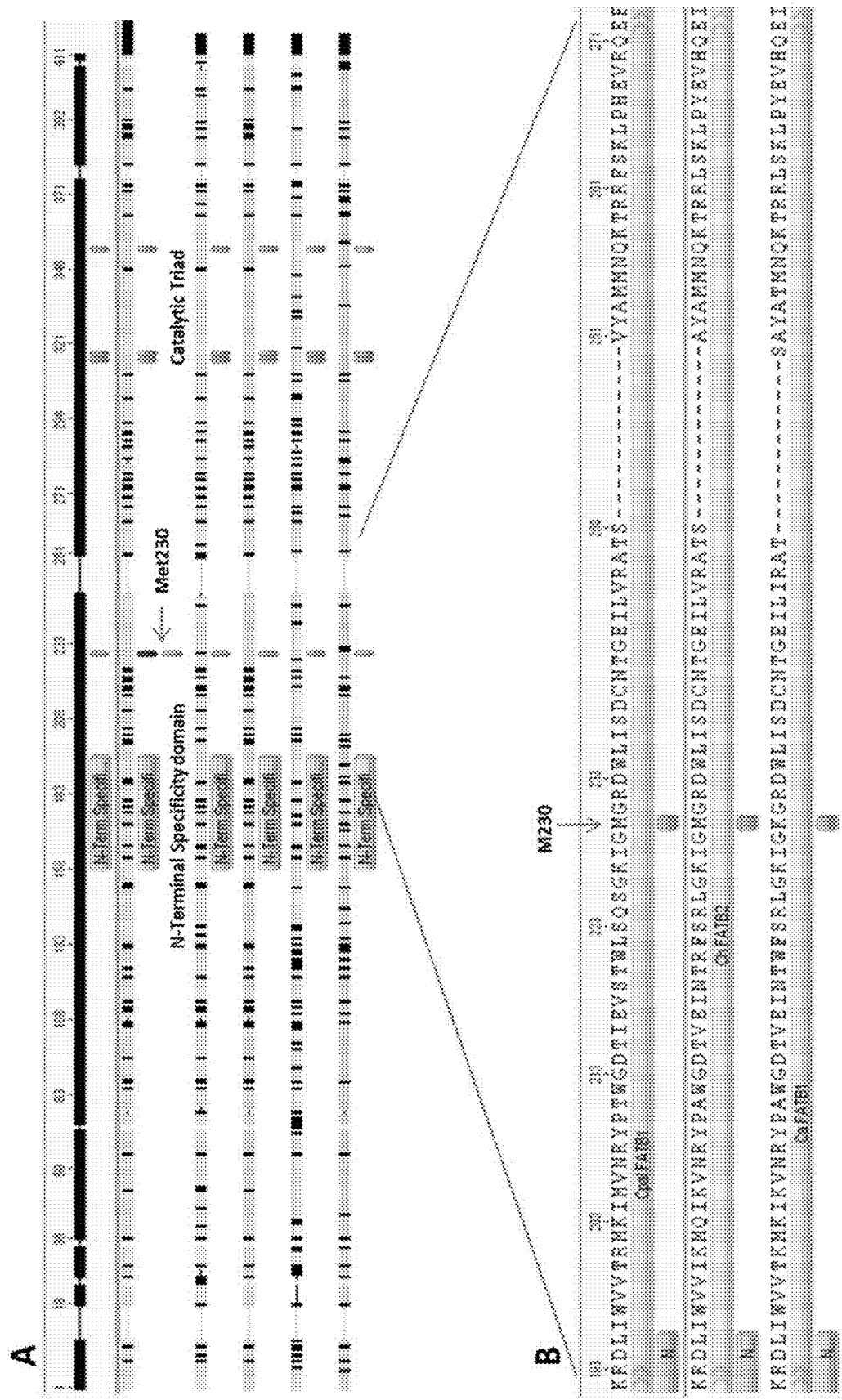
Fig. 2A-B

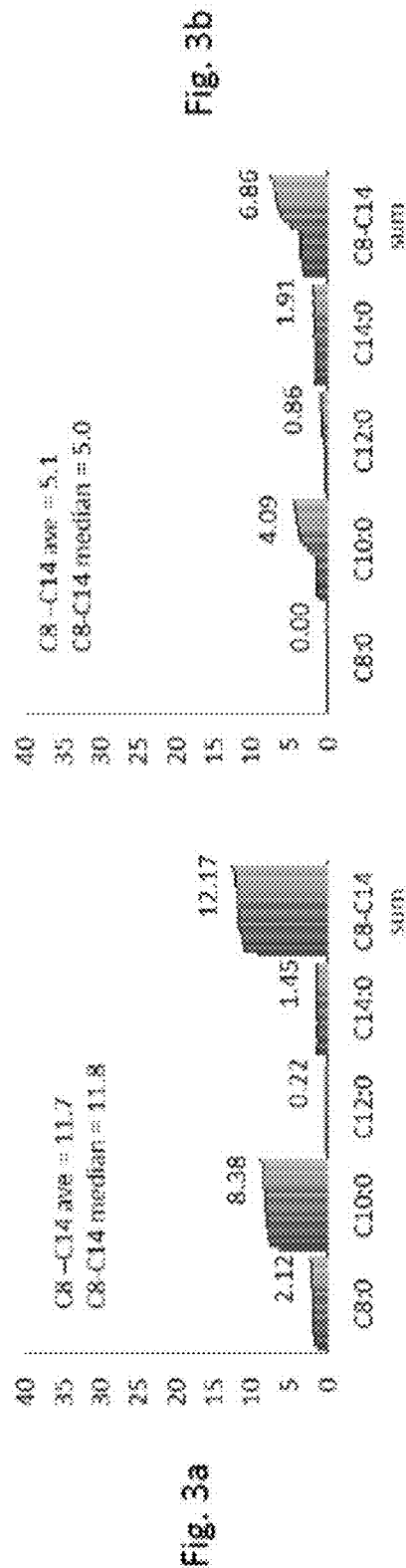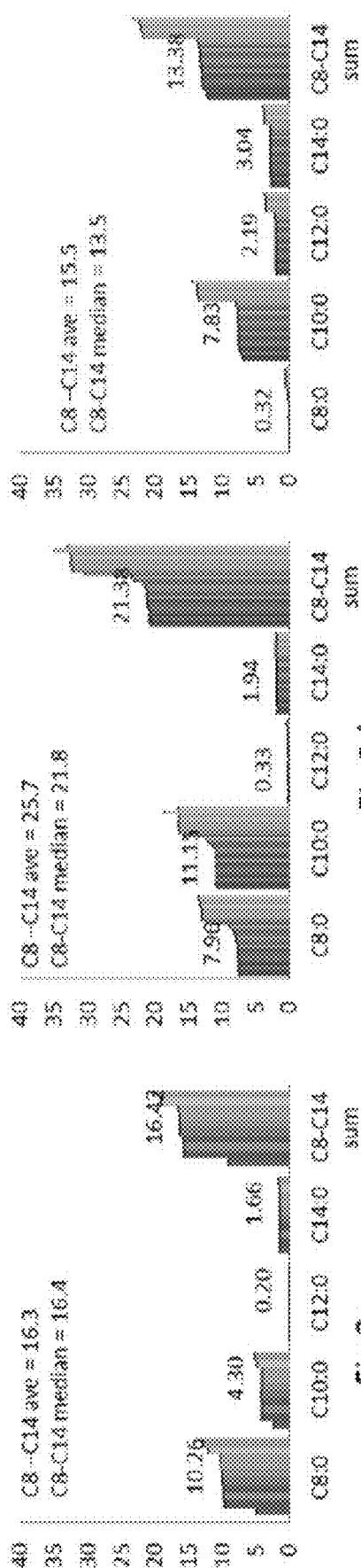

```
                          SEQUENCE LISTING

<160> NUMBER OF SEQ ID NOS: 75

<210> SEQ ID NO 1
<211> LENGTH: 415
<212> TYPE: PRT
<213> ORGANISM: Cuphea hookeriana

<400> SEQUENCE: 1

Met Val Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Asp Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
                100                 105                 110

Asp Arg Lys Ser Lys Arg Pro Asp Met Leu Val Asp Ser Phe Gly Leu
        115                 120                 125
```

Glu Ser Thr Val Gln Asp Gly Leu Val Phe Arg Gln Ser Phe Ser Ile
            130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190

Leu Ile Trp Val Val Ile Lys Met Gln Ile Lys Val Asn Arg Tyr Pro
            195                 200                 205

Ala Trp Gly Asp Thr Val Glu Ile Asn Thr Arg Phe Ser Arg Leu Gly
210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
                260                 265                 270

Pro Leu Phe Val Asp Ser Pro Val Ile Glu Asp Ser Asp Leu Lys Val
            275                 280                 285

His Lys Phe Lys Val Lys Thr Gly Asp Ser Ile Gln Lys Gly Leu Thr
290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
            355                 360                 365

Val Arg Ser Gln Tyr Gln His Leu Leu Arg Leu Glu Asp Gly Thr Ala
370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415

<210> SEQ ID NO 2
<211> LENGTH: 1474
<212> TYPE: DNA
<213> ORGANISM: Cuphea hookeriana

<400> SEQUENCE: 2
ctggatacca ttttccctgc gaaaaaacat ggtggctgct gcagcaagtt ccgcattctt      60
ccctgttcca gccccgggag cctcccctaa acccgggaag ttcggaaatt ggccctcgag     120
cttgagccct ccttcaagcc caagtcaat ccccaatggc ggatttcagg ttaaggcaaa     180
tgacagcgcc catccaaagg ctaacggttc tgcagttagt ctaaagtctg cagcctcaa      240 cactcaggag gacacttcgt cgtccctcc tcctcggact tccttcacc agttgctga       300 ttggagtagg cttctgactg caatcacgac cgtgttcgtg aaatctaaga ggcctgacat     360
gcatgatcgg aaatccaaga ggcctgacat gctggtggac tcgtttgggt tggagagtac     420
tgttcaggat gggctcgtgt tccgacagag ttttcgatt aggtcttatg aaataggcac      480

```
tgatcgaacg gcctctatag agacacttat gaaccacttg caggaaacat ctctcaatca    540
ttgtaagagt accggtattc tccttgacgg cttcggtcgt actcttgaga gtgtaaaag     600 ggacctcatt tgggtggtaa taaaaatgca gatcaaggtg aatcgctatc cagcttgggg    660
cgatactgtc gagatcaata cccggttctc ccggttgggg aaaatcggta tgggtcgcga    720
ttggctaata agtgattgca acacaggaga aattcttgta agagctacga gcgcgtatgc    780
catgatgaat caaagacga gaagactctc aaaacttcca tacgaggttc accaggagat    840
agtgcctctt tttgtcgact ctcctgtcat tgaagacagt gatctgaaag tgcataagtt    900
taaagtgaag actggtgatt ccattcaaaa gggtctaact ccggggtgga atgacttgga    960
tgtcaatcag cacgtaagca acgtgaagta cattgggtgg attctcgaga gtatgccaac   1020
agaagttttg gagacccagg agctatgctc tctcgcccctt gaatataggc gggaatgcgg   1080
aagggacagt gtgctggagt ccgtgaccgc tatggatccc tcaaaagttg gagtccgttc   1140
tcagtaccag caccttctgc ggcttgagga tgggactgct atcgtgaacg gtgcaactga   1200
gtggcggccg aagaatgcag gagctaacgg ggcgatatca acgggaaaga cttcaaatgg   1260
aaactcggtc tcttagaagt gtctcggaac ccttccgaga tgtgcatttc ttttctcctt   1320
ttcattttgt ggtgagctga aagaagagca tgtcgttgca atcagtaaat tgtgtagttc   1380 gttttttcgct ttgcttcgct cctttgtata ataatatggt cagtcgtctt tgtatcattt   1440
catgttttca gtttatttac gccatataat tttt                              1474
```

<210> SEQ ID NO 3
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Leu Ser Pro Ser Phe Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Pro Pro Arg Thr Phe Leu His
                85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn His Leu Gln Glu Thr
                165                 170                 175

Ser Leu Asn His Cys Lys Ser Thr Gly Ile Leu Leu Asp Gly Phe Gly
```

```
                    180                 185                 190
Arg Thr Pro Glu Met Cys Lys Arg Asp Leu Ile Trp Val Val Ile Lys
            195                 200                 205
Met Gln Ile Lys Val Asn Arg Tyr Pro Ala Trp Gly Asp Thr Val Glu
        210                 215                 220
Ile Asn Thr Arg Phe Ser Arg Leu Gly Lys Ile Gly Met Gly Arg Asp
225                 230                 235                 240
Trp Leu Ile Ser Asp Cys Asn Thr Gly Glu Ile Leu Val Arg Ala Thr
                245                 250                 255
Ser Ala Tyr Ala Met Met Asn Gln Lys Thr Arg Arg Leu Ser Lys Leu
            260                 265                 270
Pro Tyr Glu Val His Gln Glu Ile Val Pro Leu Phe Val Asp Ser Pro
        275                 280                 285
Val Ile Glu Asp Ser Asp Leu Lys Val His Lys Phe Lys Val Lys Thr
        290                 295                 300
Gly Asp Ser Ile Gln Lys Gly Leu Thr Pro Gly Trp Asn Asp Leu Asp
305                 310                 315                 320
Val Asn Gln His Val Ser Asn Val Lys Tyr Ile Gly Trp Ile Leu Glu
                325                 330                 335
Ser Met Pro Thr Glu Val Leu Glu Thr Gln Glu Leu Cys Ser Leu Ala
            340                 345                 350
Leu Glu Tyr Arg Arg Glu Cys Gly Arg Asp Ser Val Leu Glu Ser Val
        355                 360                 365
Thr Ala Met Asp Pro Ser Lys Val Gly Val Arg Ser Gln Tyr Gln His
        370                 375                 380
Leu Leu Arg Leu Glu Asp Gly Thr Ala Ile Val Asn Gly Ala Thr Glu
385                 390                 395                 400
Trp Arg Pro Lys Asn Ala Gly Ala Asn Gly Ala Ile Ser Thr Gly Lys
                405                 410                 415
Thr Ser Asn Gly Asn Ser Val Ser Met Asp Tyr Lys Asp His Asp Gly
            420                 425                 430
Asp Tyr Lys Asp His Asp Ile Asp Tyr Lys Asp Asp Asp Lys
        435                 440                 445

<210> SEQ ID NO 4
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Thr Ala Ser Thr Phe Ser Ala Phe Asn Ala Arg Cys Gly Asp
1               5                   10                  15
Leu Arg Arg Ser Ala Gly Ser Gly Pro Arg Arg Pro Ala Arg Pro Leu
            20                  25                  30
Pro Val Arg Gly Arg Ala Ser Ser Leu Ser Pro Ser Phe Lys Pro Lys
        35                  40                  45
Ser Ile Pro Asn Gly Gly Phe Gln Val Lys Ala Asn Asp Ser Ala His
    50                  55                  60
Pro Lys Ala Asn Gly Ser Ala Val Ser Leu Lys Ser Gly Ser Leu Asn
65                  70                  75                  80
Thr Gln Glu Asp Thr Ser Ser Pro Pro Arg Thr Phe Leu His
            85                  90                  95
```

```
Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn His Leu Gln Glu Thr
                165                 170                 175

Ser Leu Asn His Cys Lys Ser Thr Gly Ile Leu Leu Asp Gly Phe Gly
            180                 185                 190

Arg Thr Lys Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350

Leu Glu Tyr Arg Arg Glu Cys Gly Arg Asp Ser Val Leu Glu Ser Val
        355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Asp Lys
        435                 440                 445

<210> SEQ ID NO 5
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Thr Ala Ser Thr Phe Ser Ala Phe Asn Ala Arg Cys Gly Asp
1               5                   10                  15
```

```
Leu Arg Arg Ser Ala Gly Ser Gly Pro Arg Pro Ala Arg Pro Leu
            20                  25                  30

Pro Val Arg Gly Arg Ala Ser Ser Leu Ser Pro Ser Phe Lys Pro Lys
            35                  40                  45

Ser Ile Pro Asn Gly Gly Phe Gln Val Lys Ala Asn Asp Ser Ala His
 50                      55                  60

Pro Lys Ala Asn Gly Ser Ala Val Ser Leu Lys Ser Gly Ser Leu Asn
 65                      70                  75                  80

Thr Gln Glu Asp Thr Ser Ser Pro Pro Arg Thr Phe Leu His
                 85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
            115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn His Leu Gln Glu Thr
                165                 170                 175

Ser Leu Asn His Cys Lys Ser Thr Gly Ile Leu Leu Asp Gly Phe Gly
            180                 185                 190

Arg Thr Ala Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
            275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350

Leu Glu Tyr Arg Arg Glu Cys Gly Arg Asp Ser Val Leu Glu Ser Val
            355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430
```

```
Asp Tyr Lys Asp His Asp Ile Asp Tyr Lys Asp Asp Asp Lys
            435                 440                 445

<210> SEQ ID NO 6
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Leu Ser Pro Ser Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Pro Pro Arg Thr Phe Leu His
                85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn Tyr Leu Gln Glu Thr
                165                 170                 175

Ser Leu Asn His Cys Lys Ser Thr Gly Ile Leu Leu Asp Gly Phe Gly
            180                 185                 190

Arg Thr Leu Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350
```

```
Leu Glu Tyr Arg Arg Glu Cys Gly Arg Asp Ser Val Leu Glu Ser Val
            355                 360                 365

Thr Ala Met Asp Pro Ser Lys Val Gly Val Arg Ser Gln Tyr Gln His
        370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Lys
                435                 440                 445

<210> SEQ ID NO 7
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Leu Ser Pro Ser Phe Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Pro Pro Arg Thr Phe Leu His
            85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn Phe Leu Gln Glu Thr
                165                 170                 175

Ser Leu Asn His Cys Lys Ser Thr Gly Ile Leu Leu Asp Gly Phe Gly
            180                 185                 190

Arg Thr Leu Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
```

```
                260                 265                 270
Pro Tyr Glu Val His Gln Glu Ile Val Pro Leu Phe Val Asp Ser Pro
            275                 280                 285

Val Ile Glu Asp Ser Asp Leu Lys Val His Lys Phe Lys Val Lys Thr
        290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350

Leu Glu Tyr Arg Arg Glu Cys Gly Arg Asp Ser Val Leu Glu Ser Val
        355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Lys
        435                 440                 445

<210> SEQ ID NO 8
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Arg Pro Leu
            20                  25                  30

Pro Val Arg Gly Arg Ala Ser Ser Leu Ser Pro Ser Phe Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Pro Pro Arg Thr Phe Leu His
                85                  90                  95

Gln Leu Pro Asp Trp Ser Arg Leu Leu Thr Ala Ile Thr Thr Val Phe
            100                 105                 110

Val Lys Ser Lys Arg Pro Asp Met His Asp Arg Lys Ser Lys Arg Pro
        115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn His Leu Gln Glu Thr
                165                 170                 175
```

Ser Leu Asn His Cys Lys Ser Thr Gly Ile Leu Leu Asp Gly Phe Gly
            180                 185                 190

Arg Thr Leu Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350

Leu Glu Tyr Arg Arg Glu Cys Gly Arg Asp Ser Val Leu Glu Ser Val
        355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Asp Lys
        435                 440                 445

<210> SEQ ID NO 9
<211> LENGTH: 6075
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
ccctcaactg cgacgctggg aaccttctcc gggcaggcga tgtgcgtggg tttgcctcct    60
tggcacggct ctacaccgtc gagtacgcca tgaggcggtg atggctgtgt cggttgccac   120
ttcgtccaga gacggcaagt cgtccatcct ctgcgtgtgt ggcgcgacgc tgcagcagtc   180
cctctgcagc agatgagcgt gactttggcc atttcacgca ctcgagtgta cacaatccat   240
ttttcttaaa gcaaatgact gctgattgac cagatactgt aacgctgatt cgctccaga    300 tcgcacagat agcgaccatg ttgctgcgtc tgaaaatctg gattccgaat cgaccctgg    360 cgctccatcc atgcaacaga tggcgacact tgttacaatt cctgtcaccc atcggcatgg   420
agcaggtcca cttagattcc cgatcaccca cgcacatctc gctaatagtc attcgttcgt   480
gtcttcgatc aatctcaagt gagtgtgcat ggatcttggt tgacgatgcg gtatgggttt   540

```
gcgccgctgg ctgcagggtc tgcccaaggc aagctaaccc agctcctctc cccgacaata    600
ctctcgcagg caaagccggt cacttgcctt ccagattgcc aataaactca attatggcct    660
ctgtcatgcc atccatgggt ctgatgaatg gtcacgctcg tgtcctgacc gttccccagc    720
ctctggcgtc ccctgccccg cccaccagcc cacgccgcgc ggcagtcgct gccaaggctg    780
tctcggaggt acccttcctt gcgctatgac acttccagca aaggtaggg cgggctgcga    840 gacggcttcc cggcgctgca tgcaacaccg atgatgcttc gacccccga agctccttcg    900 gggctgcatg ggcgctccga tgccgctcca gggcgagcgc tgtttaaata gccaggcccc    960
cgattgcaaa gacattatag cgagctacca aagccatatt caaacaccta gatcactacc   1020
acttctacac aggccactcg agcttgtgat cgcactccgc taaggggcg cctcttcctc   1080 ttcgtttcag tcacaacccg caaactctag aatatcaatg atcgagcagg acggcctcca   1140
cgccggctcc cccgccgcct gggtggagcg cctgttcggc tacgactggg cccagcagac   1200
catcggctgc tccgacgccg ccgtgttccg cctgtccgcc cagggccgcc ccgtgctgtt   1260
cgtgaagacc gacctgtccg gcgccctgaa cgagctgcag gacgaggccg cccgcctgtc   1320
ctggctggcc accaccggcg tgccctgcgc cgccgtgctg gacgtggtga ccgaggccgg   1380
ccgcgactgg ctgctgctgg gcgaggtgcc cggccaggac ctgctgtcct cccacctggc   1440
ccccgccgag aaggtgtcca tcatggccga cgccatgcgc cgcctgcaca ccctggaccc   1500
cgccacctgc cccttcgacc accaggccaa gcaccgcatc gagcgcgccc gcacccgcat   1560
ggaggccggc ctggtggacc aggacgacct ggacgaggag caccagggcc tggcccccgc   1620
cgagctgttc gcccgcctga aggcccgcat gcccgacggc gaggacctgg tggtgaccca   1680
cggcgacgcc tgcctgccca acatcatggt ggagaacggc cgcttctccg gcttcatcga   1740
ctgcggccgc ctgggcgtgg ccgaccgcta ccaggacatc gccctggcca cccgcgacat   1800
cgccgaggag ctgggcggcg agtgggccga ccgcttcctg gtgctgtacg gcatcgccgc   1860
ccccgactcc cagcgcatcg ccttctaccg cctgctggac gagttcttct gacaattgac   1920
gcccgcgcgg cgcacctgac ctgttctctc gagggcgcct gttctgcctt gcgaaacaag   1980
cccctggagc atgcgtgcat gatcgtctct ggcgccccgc cgcgcggttt gtcgccctcg   2040
cgggcgccgc ggccgcgggg gcgcattgaa attgttgcaa accccacctg acagattgag   2100
ggcccaggca ggaaggcgtt gagatggagg tacaggagtc aagtaactga aagttttat    2160 gataactaac aacaaagggt cgtttctggc cagcgaatga caagaacaag attccacatt   2220
tccgtgtaga ggcttgccat cgaatgtgag cgggcgggcc gcggacccga caaaccctt    2280 acgacgtggt aagaaaaacg tggcgggcac tgtccctgta gcctgaagac cagcaggaga   2340
cgatcggaag catcacagca caggatcccg cgtctcgaac agagcgcgca gaggaacgct   2400
gaaggtctcg cctctgtcgc acctcagcgc ggcatacacc acaataacca cctgacgaat   2460
gcgcttggtt cttcgtccat tagcgaagcg tccggttcac acacgtgcca cgttggcgag   2520
gtggcaggtg acaatgatcg gtggagctga tggtcgaaac gttcacagcc tagggatatc   2580
atagcgactg ctaccccccg accatgtgcc gaggcagaaa ttatatacaa gaagcagatc   2640
gcaattaggc acatcgcttt gcattatcca cacactattc atcgctgctg cggcaaggct   2700
gcagagtgta tttttgtggc ccaggagctg agtccgaagt cgacgcgacg agcggcgcag   2760
gatccgaccc ctagacgagc actgtcattt tccaagcacg cagctaaatg cgctgagacc   2820
gggtctaaat catccgaaaa gtgtcaaaat ggccgattgg gttcgcctag acaatgcgc    2880
```

```
tgcggattcg ctcgagtccg ctgccggcca aaaggcggtg gtacaggaag gcgcacgggg    2940
ccaaccctgc gaagccgggg gcccgaacgc cgaccgccgg ccttcgatct cgggtgtccc    3000
cctcgtcaat ttcctctctc gggtgcagcc acgaaagtcg tgacgcaggt cacgaaatcc    3060
ggttacgaaa aacgcaggtc ttcgcaaaaa cgtgagggtt tcgcgtctcg ccctagctat    3120
tcgtatcgcc gggtcagacc cacgtgcaga aaagcccttg aataacccgg gaccgtggtt    3180
accgcgccgc ctgcaccagg gggcttatat aagcccacac cacacctgtc tcaccacgca    3240
tttctccaac tcgcgacttt tcggaagaaa ttgttatcca cctagtatag actgccacct    3300
gcaggacctt gtgtcttgca gtttgtattg gtcccggccg tcgagcacga cagatctggg    3360
ctagggttgg cctggccgct cggcactccc ctttagccgc gcgcatccgc gttccagagg    3420
tgcgattcgg tgtgtggagc attgtcatgc gcttgtgggg gtcgttccgt gcgcggcggg    3480
tccgccatgg gcgccgacct gggccctagg gttttgttttc gggccaagcg agccctctc    3540 acctcgtcgc cccccccgcat tccctctctc ttgcagccac tagtaacaat ggccaccgca    3600
tccactttct cggcgttcaa tgcccgctgc ggcgacctgc gtcgtcggc gggctccggg    3660 ccccggcgcc cagcgaggcc cctccccgtg cgcgggcgcg cctccagcct gagcccctcc    3720
ttcaagccca agtccatccc caacggcggc ttccaggtga aggccaacga cagcgcccac    3780
cccaaggcca acggctccgc cgtgagcctg aagagcggca gcctgaacac ccaggaggac    3840
acctcctcca gcccccccc ccgcaccttc ctgcaccagc tgcccgactg gagccgcctg    3900
ctgaccgcca tcaccaccgt gttcgtgaag tccaagcgcc ccgacatgca cgaccgcaag    3960
tccaagcgcc ccgacatgct ggtggacagc ttcggcctgg agtccaccgt gcaggacggc    4020
ctggtgttcc gccagtcctt ctccatccgc tcctacgaga tcggcaccga ccgcaccgcc    4080
agcatcgaga ccctgatgaa ccacctgcag gagacctccc tgaaccactg caagagcacc    4140
ggcatcctgc tggacggctt cggccgcacc ctggagatgt gcaagcgcga cctgatctgg    4200
gtggtgatca agatgcagat caaggtgaac cgctaccccg cctggggcga caccgtggag    4260
atcaacaccc gcttcagccg cctgggcaag atcggcatgg gccgcgactg gctgatctcc    4320
gactgcaaca ccggcgagat cctggtgcgc gccaccagcg cctacgccat gatgaaccag    4380
aagacccgcc gcctgtccaa gctgccctac gaggtgcacc aggagatcgt gcccctgttc    4440
gtggacagcc ccgtgatcga ggactccgac ctgaaggtgc acaagttcaa ggtgaagacc    4500
ggcgacagca tccagaaggg cctgaccccc ggctggaacg acctggacgt gaaccagcac    4560
gtgtccaacg tgaagtacat cggctggatc ctggagagca tgcccaccga ggtgctggag    4620
acccaggagc tgtgctccct ggccctggag taccgccgcg agtgcggccg cgactccgtg    4680
ctggagagcg tgaccgccat ggaccccagc aaggtgggcg tgcgctccca gtaccagcac    4740
ctgctgcgcc tggaggacgg caccgccatc gtgaacggcg ccaccgagtg gcgcccaag    4800 aacgccggcg ccaacggcgc catctccacc ggcaagacca gcaacggcaa ctccgtgtcc    4860
atggactaca aggaccacga cggcgactac aaggaccacg acatcgacta caaggacgac    4920
gacgacaagt gactcgaggc agcagcagct cggatagtat cgacacactc tggacgctgg    4980
tcgtgtgatg gactgttgcc gccacacttg ctgccttgac ctgtgaatat ccctgccgct    5040
tttatcaaac agcctcagtg tgtttgatct tgtgtgtacg cgcttttgcg agttgctagc    5100
tgcttgtgct atttgcgaat accacccca gcatcccctt ccctcgtttc atatcgcttg    5160
catcccaacc gcaacttatt tacgctgtcc tgctatccct cagcgctgct cctgctcctg    5220
ctcactgccc ctcgcacagc cttggtttgg gctccgcctg tattctcctg gtactgcaac    5280
```

```
ctgtaaacca gcactgcaat gctgatgcac gggaagtagt gggatgggaa cacaaatgga    5340
aagctgtata gggataacag ggtaatgagc tccagcgcca tgccacgccc tttgatggct    5400
tcaagtacga ttacggtgtt ggattgtgtg tttgttgcgt agtgtgcatg gtttagaata    5460
atacacttga tttcttgctc acggcaatct cggcttgtcc gcaggttcaa ccccatttcg    5520
gagtctcagg tcagccgcgc aatgaccagc cgctacttca aggacttgca cgacaacgcc    5580
gaggtgagct atgtttagga cttgattgga aattgtcgtc gacgcatatt cgcgctccgc    5640
gacagcaccc aagcaaaatg tcaagtgcgt tccgatttgc gtccgcaggt cgatgttgtg    5700
atcgtcggcg ccggatccgc cggtctgtcc tgcgcttacg agctgaccaa gcaccctgac    5760
gtccgggtac gcgagctgag attcgattag acataaattg aagattaaac ccgtagaaaa    5820
atttgatggt cgcgaaactg tgctcgattg caagaaattg atcgtcctcc actccgcagg    5880
tcgccatcat cgagcagggc gttgctcccg gcggcggcgc ctggctgggg ggacagctgt    5940
tctcggccat gtgtgtacgt agaaggatga atttcagctg gttttcgttg cacagctgtt    6000
tgtgcatgat ttgtttcaga ctattgttga atgtttttag atttcttagg atgcatgatt    6060
tgtctgcatg cgact                                                     6075
```

<210> SEQ ID NO 10
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Ser Ser Leu Ser Pro Ser Leu Lys Pro
        35                  40                  45

Lys Ser Ile Pro Asn Gly Gly Phe Gln Val Lys Ala Asn Ala Ser Ala
    50                  55                  60

His Pro Lys Ala Asn Gly Ser Ala Val Thr Leu Lys Ser Gly Ser Leu
65                  70                  75                  80

Asn Thr Gln Glu Asp Thr Leu Ser Ser Pro Pro Arg Ala Phe
                85                  90                  95

Phe Asn Gln Leu Pro Asp Trp Ser Met Leu Leu Thr Ala Ile Thr Thr
            100                 105                 110

Val Phe Val Ala Pro Glu Lys Arg Trp Thr Met Phe Asp Arg Lys Ser
        115                 120                 125

Lys Arg Pro Asn Met Leu Met Asp Ser Phe Gly Leu Glu Arg Val Val
    130                 135                 140

Gln Asp Gly Leu Val Phe Arg Gln Ser Phe Ser Ile Arg Ser Tyr Glu
145                 150                 155                 160

Ile Cys Ala Asp Arg Thr Ala Ser Ile Glu Thr Val Met Asn His Val
                165                 170                 175

Gln Glu Thr Ser Leu Asn Gln Cys Lys Ser Ile Gly Leu Leu Asp Asp
            180                 185                 190

Gly Phe Gly Arg Ser Pro Glu Met Cys Lys Arg Asp Leu Ile Trp Val
        195                 200                 205

Val Thr Arg Met Lys Ile Met Val Asn Arg Tyr Pro Thr Trp Gly Asp
210                 215                 220

Thr Ile Glu Val Ser Thr Trp Leu Ser Gln Ser Gly Lys Ile Gly Met
225                 230                 235                 240

Gly Arg Asp Trp Leu Ile Ser Asp Cys Asn Thr Gly Glu Ile Leu Val
            245                 250                 255

Arg Ala Thr Ser Val Tyr Ala Met Met Asn Gln Lys Thr Arg Arg Phe
        260                 265                 270

Ser Lys Leu Pro His Glu Val Arg Gln Glu Phe Ala Pro His Phe Leu
    275                 280                 285

Asp Ser Pro Pro Ala Ile Glu Asp Asn Asp Gly Lys Leu Gln Lys Phe
290                 295                 300

Asp Val Lys Thr Gly Asp Ser Ile Arg Lys Gly Leu Thr Pro Gly Trp
305                 310                 315                 320

Tyr Asp Leu Asp Val Asn Gln His Val Ser Asn Val Lys Tyr Ile Gly
            325                 330                 335

Trp Ile Leu Glu Ser Met Pro Thr Glu Val Leu Glu Thr Gln Glu Leu
        340                 345                 350

Cys Ser Leu Thr Leu Glu Tyr Arg Arg Glu Cys Gly Arg Asp Ser Val
    355                 360                 365

Leu Glu Ser Val Thr Ser Met Asp Pro Ser Lys Val Gly Asp Arg Phe
370                 375                 380

Gln Tyr Arg His Leu Leu Arg Leu Glu Asp Gly Ala Asp Ile Met Lys
385                 390                 395                 400

Gly Arg Thr Glu Trp Arg Pro Lys Asn Ala Gly Thr Asn Gly Ala Ile
            405                 410                 415

Ser Thr Gly Lys Thr Met Asp Tyr Lys Asp His Asp Gly Asp Tyr Lys
        420                 425                 430

Asp His Asp Ile Asp Tyr Lys Asp Asp Asp Lys
    435                 440

<210> SEQ ID NO 11
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Pro Ala Arg Pro Leu
            20                  25                  30

Pro Val Arg Gly Arg Ala Ser Ser Leu Ser Pro Ser Lys Pro Lys
        35                  40                  45

Ser Ile Pro Asn Gly Gly Phe Gln Val Lys Ala Asn Asp Ser Ala His
    50                  55                  60

Pro Lys Ala Asn Gly Ser Ala Val Ser Leu Lys Ser Gly Ser Leu Asn
65                  70                  75                  80

Thr Gln Glu Asp Thr Ser Ser Pro Pro Arg Thr Phe Leu His
            85                  90                  95

Gln Leu Pro Asp Trp Ser Arg Leu Leu Thr Ala Ile Thr Thr Val Phe
        100                 105                 110

Val Lys Ser Lys Arg Pro Asp Met His Asp Arg Lys Ser Lys Arg Pro
    115                 120                 125

Asp Met Leu Val Asp Ser Phe Gly Leu Glu Ser Thr Val Gln Asp Gly
    130                 135                 140

Leu Val Phe Arg Gln Ser Phe Ser Ile Arg Ser Tyr Glu Ile Gly Thr
145                 150                 155                 160

Asp Arg Thr Ala Ser Ile Glu Thr Leu Met Asn His Leu Gln Glu Thr
                165                 170                 175

Ser Leu Asn His Cys Lys Ser Thr Gly Ile Leu Leu Asp Gly Phe Gly
            180                 185                 190

Arg Thr Leu Glu Met Cys Lys Arg Asp Leu Ile Trp Val Val Ile Lys
        195                 200                 205

Met Gln Ile Lys Val Asn Arg Tyr Pro Ala Trp Gly Asp Thr Val Glu
    210                 215                 220

Ile Asn Thr Arg Phe Ser Arg Leu Gly Lys Ile Gly Met Gly Arg Asp
225                 230                 235                 240

Trp Leu Ile Ser Asp Cys Asn Thr Gly Glu Ile Leu Val Arg Ala Thr
                245                 250                 255

Ser Ala Tyr Ala Met Met Asn Gln Lys Thr Arg Arg Leu Ser Lys Leu
            260                 265                 270

Pro Tyr Glu Val His Gln Glu Ile Val Pro Leu Phe Val Asp Ser Pro
        275                 280                 285

Val Ile Glu Asp Ser Asp Leu Lys Val His Lys Phe Lys Val Lys Thr
    290                 295                 300

Gly Asp Ser Ile Gln Lys Gly Leu Thr Pro Gly Trp Asn Asp Leu Asp
305                 310                 315                 320

Val Asn Gln His Val Ser Asn Val Lys Tyr Ile Gly Trp Ile Leu Glu
                325                 330                 335

Ser Met Pro Thr Glu Val Leu Glu Thr Gln Glu Leu Cys Ser Leu Ala
            340                 345                 350

Leu Glu Tyr Arg Arg Glu Cys Gly Arg Asp Ser Val Leu Glu Ser Val
        355                 360                 365

Thr Ala Met Asp Pro Ser Lys Val Gly Val Arg Ser Gln Tyr Gln His
    370                 375                 380

Leu Leu Arg Leu Glu Asp Gly Thr Ala Ile Val Asn Gly Ala Thr Glu
385                 390                 395                 400

Trp Arg Pro Lys Asn Ala Gly Ala Asn Gly Ala Ile Ser Thr Gly Lys
                405                 410                 415

Thr Ser Asn Gly Asn Ser Val Ser Met Asp Tyr Lys Asp His Asp Gly
            420                 425                 430

Asp Tyr Lys Asp His Asp Ile Asp Tyr Lys Asp Asp Asp Lys
        435                 440                 445

<210> SEQ ID NO 12
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ser Arg Ala His Pro Lys Ala Asn Gly

```
                35                  40                  45
Ser Ala Val Ser Leu Lys Ser Gly Ser Leu Asn Thr Gln Glu Asp Thr
 50                  55                  60
Ser Ser Ser Pro Pro Arg Thr Phe Leu His Gln Leu Pro Asp Trp
 65                  70                  75                  80
Ser Arg Leu Leu Thr Ala Ile Thr Thr Val Phe Val Lys Ser Lys Arg
                 85                  90                  95
Pro Asp Met His Asp Arg Lys Ser Lys Arg Pro Asp Met Leu Met Asp
                100                 105                 110
Ser Phe Gly Leu Glu Ser Ile Val Gln Glu Gly Leu Glu Phe Arg Gln
            115                 120                 125
Ser Phe Ser Ile Arg Ser Tyr Glu Ile Gly Thr Asp Arg Thr Ala Ser
            130                 135                 140
Ile Glu Thr Leu Met Asn Tyr Leu Gln Glu Thr Ser Leu Asn His Cys
145                 150                 155                 160
Lys Ser Thr Gly Ile Leu Leu Asp Gly Phe Gly Arg Thr Pro Glu Met
                165                 170                 175
Cys Lys Arg Asp Leu Ile Trp Val Val Thr Lys Met Lys Ile Lys Val
                180                 185                 190
Asn Arg Tyr Pro Ala Trp Gly Asp Thr Val Glu Ile Asn Thr Trp Phe
                195                 200                 205
Ser Arg Leu Gly Lys Ile Gly Lys Gly Arg Asp Trp Leu Ile Ser Asp
210                 215                 220
Cys Asn Thr Gly Glu Ile Leu Ile Arg Ala Thr Ser Ala Tyr Ala Thr
225                 230                 235                 240
Met Asn Gln Lys Thr Arg Arg Leu Ser Lys Leu Pro Tyr Glu Val His
                245                 250                 255
Gln Glu Ile Ala Pro Leu Phe Val Asp Ser Pro Val Ile Glu Asp
            260                 265                 270
Asn Asp Leu Lys Leu His Lys Phe Glu Val Lys Thr Gly Asp Ser Ile
            275                 280                 285
His Lys Gly Leu Thr Pro Gly Trp Asn Asp Leu Asp Val Asn Gln His
        290                 295                 300
Val Ser Asn Val Lys Tyr Ile Gly Trp Ile Leu Glu Ser Met Pro Thr
305                 310                 315                 320
Glu Val Leu Glu Thr Gln Glu Leu Cys Ser Leu Ala Leu Glu Tyr Arg
                325                 330                 335
Arg Glu Cys Gly Arg Asp Ser Val Leu Glu Ser Val Thr Ala Met Asp
                340                 345                 350
Pro Thr Lys Val Gly Gly Arg Ser Gln Tyr Gln His Leu Leu Arg Leu
                355                 360                 365
Glu Asp Gly Thr Asp Ile Val Lys Cys Arg Thr Glu Trp Arg Pro Lys
            370                 375                 380
Asn Pro Gly Ala Asn Gly Ala Ile Ser Thr Gly Lys Thr Ser Asn Gly
385                 390                 395                 400
Asn Ser Val Ser Met Asp Tyr Lys Asp His Asp Gly Asp Tyr Lys Asp
                405                 410                 415
His Asp Ile Asp Tyr Lys Asp Asp Asp Lys
            420                 425

<210> SEQ ID NO 13
<211> LENGTH: 411
<212> TYPE: PRT
<213> ORGANISM: Cuphea palustris
```

<400> SEQUENCE: 13

```
Met Val Ala Ala Ala Ser Ser Ala Cys Phe Pro Val Pro Ser Pro
1               5                   10                  15

Gly Ala Ser Pro Lys Pro Gly Lys Leu Gly Asn Trp Ser Ser Leu
            20                  25                  30

Ser Pro Ser Leu Lys Pro Lys Ser Ile Pro Asn Gly Gly Phe Gln Val
        35                  40                  45

Lys Ala Asn Ala Ser Ala His Pro Lys Ala Asn Gly Ser Ala Val Thr
50                  55                  60

Leu Lys Ser Gly Ser Leu Asn Thr Gln Glu Asp Thr Leu Ser Ser Ser
65                  70                  75                  80

Pro Pro Pro Arg Ala Phe Phe Asn Gln Leu Pro Asp Trp Ser Met Leu
                85                  90                  95

Leu Thr Ala Ile Thr Thr Val Phe Val Ala Pro Glu Lys Arg Trp Thr
                100                 105                 110

Met Phe Asp Arg Lys Ser Lys Arg Pro Asn Met Leu Met Asp Ser Phe
            115                 120                 125

Gly Leu Glu Arg Val Val Gln Asp Gly Leu Val Phe Arg Gln Ser Phe
130                 135                 140

Ser Ile Arg Ser Tyr Glu Ile Cys Ala Asp Arg Thr Ala Ser Ile Glu
145                 150                 155                 160

Thr Val Met Asn His Val Gln Glu Thr Ser Leu Asn Gln Cys Lys Ser
                165                 170                 175

Ile Gly Leu Leu Asp Asp Gly Phe Gly Arg Ser Pro Glu Met Cys Lys
            180                 185                 190

Arg Asp Leu Ile Trp Val Val Thr Arg Met Lys Ile Met Val Asn Arg
            195                 200                 205

Tyr Pro Thr Trp Gly Asp Thr Ile Glu Val Ser Thr Trp Leu Ser Gln
210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Val Tyr Ala Met Met Asn
                245                 250                 255

Gln Lys Thr Arg Arg Phe Ser Lys Leu Pro His Glu Val Arg Gln Glu
            260                 265                 270

Phe Ala Pro His Phe Leu Asp Ser Pro Ala Ile Glu Asp Asn Asp
            275                 280                 285

Gly Lys Leu Gln Lys Phe Asp Val Lys Thr Gly Asp Ser Ile Arg Lys
            290                 295                 300

Gly Leu Thr Pro Gly Trp Tyr Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Asp Ser Val Leu Glu Ser Val Thr Ser Met Asp Pro Ser
            355                 360                 365

Lys Val Gly Asp Arg Phe Gln Tyr Arg His Leu Leu Arg Leu Glu Asp
            370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr
```

<210> SEQ ID NO 14
<211> LENGTH: 416
<212> TYPE: PRT
<213> ORGANISM: Cuphea avigera

<400> SEQUENCE: 14

Met Val Ala Ala Ala Ser Ala Phe Phe Ser Val Pro Val Pro
1               5                   10                  15

Gly Thr Ser Pro Lys Pro Gly Lys Phe Arg Ile Trp Pro Ser Ser Leu
                20                  25                  30

Ser Pro Ser Phe Lys Pro Lys Pro Ile Pro Asn Gly Gly Leu Gln Val
            35                  40                  45

Lys Ala Asn Ser Arg Ala His Pro Lys Ala Asn Gly Ser Ala Val Ser
50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
                100                 105                 110

Asp Arg Lys Ser Lys Arg Pro Asp Met Leu Met Asp Ser Phe Gly Leu
            115                 120                 125

Glu Ser Ile Val Gln Glu Gly Leu Glu Phe Arg Gln Ser Phe Ser Ile
130                 135                 140

Arg Ser Tyr Glu Ile Gly Thr Asp Arg Thr Ala Ser Ile Glu Thr Leu
145                 150                 155                 160

Met Asn Tyr Leu Gln Glu Thr Ser Leu Asn His Cys Lys Ser Thr Gly
                165                 170                 175

Ile Leu Leu Asp Gly Phe Gly Arg Thr Pro Glu Met Cys Lys Arg Asp
            180                 185                 190

Leu Ile Trp Val Val Thr Lys Met Lys Ile Lys Val Asn Arg Tyr Pro
            195                 200                 205

Ala Trp Gly Asp Thr Val Glu Ile Asn Thr Trp Phe Ser Arg Leu Gly
210                 215                 220

Lys Ile Gly Lys Gly Arg Asp Trp Leu Ile Ser Asp Cys Asn Thr Gly
225                 230                 235                 240

Glu Ile Leu Ile Arg Ala Thr Ser Ala Tyr Ala Thr Met Asn Gln Lys
                245                 250                 255

Thr Arg Arg Leu Ser Lys Leu Pro Tyr Glu Val His Gln Glu Ile Ala
            260                 265                 270

Pro Leu Phe Val Asp Ser Pro Val Ile Glu Asp Asn Asp Leu Lys
            275                 280                 285

Leu His Lys Phe Glu Val Lys Thr Gly Asp Ser Ile His Lys Gly Leu
290                 295                 300

Thr Pro Gly Trp Asn Asp Leu Asp Val Asn Gln His Val Ser Asn Val
305                 310                 315                 320

Lys Tyr Ile Gly Trp Ile Leu Glu Ser Met Pro Thr Glu Val Leu Glu
                325                 330                 335

Thr Gln Glu Leu Cys Ser Leu Ala Leu Glu Tyr Arg Arg Glu Cys Gly
            340                 345                 350

Arg Asp Ser Val Leu Glu Ser Val Thr Ala Met Asp Pro Thr Lys Val
            355                 360                 365

-continued

```
Gly Gly Arg Ser Gln Tyr Gln His Leu Leu Arg Leu Glu Asp Gly Thr
        370                 375                 380

Asp Ile Val Lys Cys Arg Thr Glu Trp Arg Pro Lys Asn Pro Gly Ala
385                 390                 395                 400

Asn Gly Ala Ile Ser Thr Gly Lys Thr Ser Asn Gly Asn Ser Val Ser
                405                 410                 415

<210> SEQ ID NO 15
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ile Pro Pro Arg Ile Ile Val Val Ser Ser
        35                  40                  45

Ser Ser Ser Lys Val Asn Pro Leu Lys Thr Glu Ala Val Val Ser Ser
    50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Leu Leu Gln Glu Val Gly
            100                 105                 110

Cys Asn His Ala Gln Ser Val Gly Tyr Ser Thr Gly Gly Phe Ser Thr
        115                 120                 125

Thr Pro Thr Met Arg Lys Leu Arg Leu Ile Trp Val Thr Ala Arg Met
    130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Thr Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
        195                 200                 205

Val Asp Val Arg Asp Glu Tyr Leu Val His Cys Pro Arg Glu Leu Arg
    210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
        275                 280                 285

Gln Thr Ile Thr Leu Asp Tyr Arg Arg Glu Cys Gln His Asp Asp Val
    290                 295                 300

Val Asp Ser Leu Thr Ser Pro Glu Pro Ser Glu Asp Ala Glu Ala Val
305                 310                 315                 320
```

```
Phe Asn His Asn Gly Thr Asn Gly Ser Ala Asn Val Ser Ala Asn Asp
            325                 330                 335

His Gly Cys Arg Asn Phe Leu His Leu Leu Arg Leu Ser Gly Asn Gly
        340                 345                 350

Leu Glu Ile Asn Arg Gly Arg Thr Glu Trp Arg Lys Lys Pro Thr Arg
            355                 360                 365

Met Asp Tyr Lys Asp His Asp Gly Asp Tyr Lys Asp His Asp Ile Asp
    370                 375                 380

Tyr Lys Asp Asp Asp Asp Lys
385                 390
```

<210> SEQ ID NO 16
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Pro Ala Arg Pro Leu
            20                  25                  30

Pro Val Arg Gly Arg Ala Ile Pro Arg Ile Ile Val Ser Ser
        35                  40                  45

Ser Ser Ser Lys Val Asn Pro Leu Lys Thr Glu Ala Val Val Ser Ser
50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Leu Leu Gln Glu Val Gly
            100                 105                 110

Cys Asn His Ala Gln Ser Val Gly Tyr Ser Thr Gly Gly Phe Ala Thr
        115                 120                 125

Thr Pro Thr Met Arg Lys Leu Arg Leu Ile Trp Val Thr Ala Arg Met
130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Thr Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
        195                 200                 205

Ala Asp Val Arg Asp Glu Tyr Leu Val His Cys Pro Arg Glu Leu Arg
    210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
```

```
                     275                 280                 285
Gln Thr Ile Thr Leu Asp Tyr Arg Arg Glu Cys Gln His Asp Asp Val
            290                 295                 300
Val Asp Ser Leu Thr Ser Pro Glu Pro Ser Glu Asp Ala Glu Ala Val
305                 310                 315                 320
Phe Asn His Asn Gly Thr Asn Gly Ser Ala Asn Val Ser Ala Asn Asp
                325                 330                 335
His Gly Cys Arg Asn Phe Leu His Leu Leu Arg Leu Ser Gly Asn Gly
            340                 345                 350
Leu Glu Ile Asn Arg Gly Arg Thr Glu Trp Arg Lys Lys Pro Thr Arg
                355                 360                 365
Met Asp Tyr Lys Asp His Asp Gly Asp Tyr Lys Asp His Asp Ile Asp
370                 375                 380
Tyr Lys Asp Asp Asp Asp Lys
385                 390

<210> SEQ ID NO 17
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Thr Ala Ser Thr Phe Ser Ala Phe Asn Ala Arg Cys Gly Asp
1               5                   10                  15
Leu Arg Arg Ser Ala Gly Ser Gly Pro Arg Arg Pro Ala Arg Pro Leu
            20                  25                  30
Pro Val Arg Gly Arg Ala Ile Pro Pro Arg Ile Ile Val Val Ser Ser
        35                  40                  45
Ser Ser Ser Lys Val Asn Pro Leu Lys Thr Glu Ala Val Val Ser Ser
    50                  55                  60
Gly Leu Ala Asp Arg Leu Arg Leu Gly Ser Leu Thr Glu Asp Gly Leu
65                  70                  75                  80
Ser Tyr Lys Glu Lys Phe Ile Val Arg Cys Tyr Glu Val Gly Ile Asn
                85                  90                  95
Lys Thr Ala Thr Val Glu Thr Ile Ala Asn Leu Leu Gln Glu Val Gly
            100                 105                 110
Cys Asn His Ala Gln Ser Val Gly Tyr Ser Thr Gly Gly Phe Val Thr
        115                 120                 125
Thr Pro Thr Met Arg Lys Leu Arg Leu Ile Trp Val Thr Ala Arg Met
    130                 135                 140
His Ile Glu Ile Tyr Lys Tyr Pro Ala Trp Ser Asp Val Val Glu Ile
145                 150                 155                 160
Glu Ser Trp Gly Gln Gly Glu Gly Lys Ile Gly Thr Arg Arg Asp Trp
                165                 170                 175
Ile Leu Arg Asp Tyr Ala Thr Gly Gln Val Ile Gly Arg Ala Thr Ser
            180                 185                 190
Lys Trp Val Met Met Asn Gln Asp Thr Arg Arg Leu Gln Lys Val Asp
        195                 200                 205
Ala Asp Val Arg Asp Glu Tyr Leu Val His Cys Pro Arg Glu Leu Arg
    210                 215                 220
Leu Ala Phe Pro Glu Glu Asn Asn Ser Ser Leu Lys Lys Ile Ser Lys
225                 230                 235                 240
```

```
Leu Glu Asp Pro Ser Gln Tyr Ser Lys Leu Gly Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
        275                 280                 285

Gln Thr Ile Thr Leu Asp Tyr Arg Arg Glu Cys Gln His Asp Asp Val
    290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Leu Arg Leu Ser Gly Asn Gly
            340                 345                 350

Leu Glu Ile Asn Arg Gly Arg Thr Glu Trp Arg Lys Lys Pro Thr Arg
        355                 360                 365

Met Asp Tyr Lys Asp His Asp Gly Asp Tyr Lys Asp His Asp Ile Asp
    370                 375                 380

Tyr Lys Asp Asp Asp Asp Lys
385                 390
```

<210> SEQ ID NO 18
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ile Pro Pro Arg Ile Ile Val Val Ser Ser
        35                  40                  45

Ser Ser Ser Lys Val Asn Pro Leu Lys Thr Glu Ala Val Val Ser Ser
    50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Leu Leu Gln Glu Val Ala
            100                 105                 110

Cys Asn His Ala Gln Ser Val Gly Tyr Ser Thr Gly Gly Phe Ser Thr
        115                 120                 125

Thr Pro Thr Met Arg Lys Leu Arg Leu Ile Trp Val Thr Ala Arg Met
    130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Thr Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
        195                 200                 205
```

Val Asp Val Arg Asp Glu Tyr Leu Val His Cys Pro Arg Glu Leu Arg
            210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
            245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
            275                 280                 285

Gln Thr Ile Thr Leu Asp Tyr Arg Arg Glu Cys Gln His Asp Asp Val
290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
            325                 330                 335

His Gly Cys Arg Asn Phe Leu His Leu Leu Arg Leu Ser Gly Asn Gly
            340                 345                 350

Leu Glu Ile Asn Arg Gly Arg Thr Glu Trp Arg Lys Lys Pro Thr Arg
            355                 360                 365

Met Asp Tyr Lys Asp His Asp Gly Asp Tyr Lys Asp His Asp Ile Asp
            370                 375                 380

Tyr Lys Asp Asp Asp Asp Lys
385                 390

<210> SEQ ID NO 19
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ile Pro Pro Arg Ile Ile Val Val Ser Ser
            35                  40                  45

Ser Ser Ser Lys Val Asn Pro Leu Lys Thr Glu Ala Val Val Ser Ser
50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
            85                  90                  95

Lys Thr Ala Thr Val Glu Thr Ile Ala Asn Leu Leu Gln Glu Val Thr
            100                 105                 110

Cys Asn His Ala Gln Ser Val Gly Tyr Ser Thr Gly Gly Phe Ser Thr
            115                 120                 125

Thr Pro Thr Met Arg Lys Leu Arg Leu Ile Trp Val Thr Ala Arg Met
            130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Thr Arg Arg Asp Trp

```
                165                 170                 175
Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
            195                 200                 205

Val Asp Val Arg Asp Glu Tyr Leu Val His Cys Pro Arg Glu Leu Arg
210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
                260                 265                 270

Trp Val Leu Glu Ser Met Pro Gln Glu Ile Ile Asp Thr His Glu Leu
                275                 280                 285

Gln Thr Ile Thr Leu Asp Tyr Arg Arg Glu Cys Gln His Asp Asp Val
            290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Leu Arg Leu Ser Gly Asn Gly
                340                 345                 350

Leu Glu Ile Asn Arg Gly Arg Thr Glu Trp Arg Lys Lys Pro Thr Arg
            355                 360                 365

Met Asp Tyr Lys Asp His Asp Gly Asp Tyr Lys Asp His Asp Ile Asp
        370                 375                 380

Tyr Lys Asp Asp Asp Asp Lys
385                 390

<210> SEQ ID NO 20
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ile Pro Pro Arg Ile Ile Val Val Ser Ser
        35                  40                  45

Ser Ser Ser Lys Val Asn Pro Leu Lys Thr Glu Ala Val Val Ser Ser
    50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Leu Leu Gln Glu Val Val
            100                 105                 110

Cys Asn His Ala Gln Ser Val Gly Tyr Ser Thr Gly Gly Phe Ser Thr
        115                 120                 125
```

```
Thr Pro Thr Met Arg Lys Leu Arg Leu Ile Trp Val Thr Ala Arg Met
    130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Thr Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
        195                 200                 205

Val Asp Val Arg Asp Glu Tyr Leu Val His Cys Pro Arg Glu Leu Arg
    210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
        275                 280                 285

Gln Thr Ile Thr Leu Asp Tyr Arg Arg Glu Cys Gln His Asp Asp Val
    290                 295                 300

Val Asp Ser Leu Thr Ser Pro Glu Pro Ser Glu Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Arg Leu Ser Gly Asn Gly
            340                 345                 350

Leu Glu Ile Asn Arg Gly Arg Thr Glu Trp Arg Lys Lys Pro Thr Arg
        355                 360                 365

Met Asp Tyr Lys Asp His Asp Gly Asp Tyr Lys Asp His Asp Ile Asp
    370                 375                 380

Tyr Lys Asp Asp Asp Asp Lys
385                 390
```

<210> SEQ ID NO 21
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ile Pro Pro Arg Ile Ile Val Val Ser Ser
        35                  40                  45

Ser Ser Ser Lys Val Asn Pro Leu Lys Thr Glu Ala Val Ser Ser
    50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95
```

Lys Thr Ala Thr Val Glu Thr Ile Ala Asn Leu Leu Gln Glu Val Gly
                100                 105                 110

Cys Asn His Ala Gln Ser Val Gly Tyr Ser Thr Ala Gly Phe Ser Thr
            115                 120                 125

Thr Pro Thr Met Arg Lys Leu Arg Leu Ile Trp Val Thr Ala Arg Met
    130                 135                 140

His Ile Glu Ile Tyr Lys Tyr Pro Ala Trp Ser Asp Val Val Glu Ile
145                 150                 155                 160

Glu Ser Trp Gly Gln Gly Gly Lys Ile Gly Thr Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
    195                 200                 205

Val Asp Val Arg Asp Glu Tyr Leu Val His Cys Pro Arg Glu Leu Arg
210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
    275                 280                 285

Gln Thr Ile Thr Leu Asp Tyr Arg Arg Glu Cys Gln His Asp Asp Val
290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Leu Arg Leu Ser Gly Asn Gly
            340                 345                 350

Leu Glu Ile Asn Arg Gly Arg Thr Glu Trp Arg Lys Lys Pro Thr Arg
    355                 360                 365

Met Asp Tyr Lys Asp His Asp Gly Asp Tyr Lys Asp His Asp Ile Asp
370                 375                 380

Tyr Lys Asp Asp Asp Asp Lys
385                 390

<210> SEQ ID NO 22
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
                20                  25                  30

Pro Val Arg Gly Arg Ala Ile Pro Pro Arg Ile Ile Val Val Ser Ser
            35                  40                  45

Ser Ser Ser Lys Val Asn Pro Leu Lys Thr Glu Ala Val Val Ser Ser

```
                    50                  55                  60
Gly Leu Ala Asp Arg Leu Arg Leu Gly Ser Leu Thr Glu Asp Gly Leu
 65                  70                  75                  80

Ser Tyr Lys Glu Lys Phe Ile Val Arg Cys Tyr Glu Val Gly Ile Asn
                 85                  90                  95

Lys Thr Ala Thr Val Glu Thr Ile Ala Asn Phe Leu Gln Glu Val Gly
            100                 105                 110

Cys Asn His Ala Gln Ser Val Gly Tyr Ser Thr Gly Gly Phe Ser Thr
            115                 120                 125

Thr Pro Thr Met Arg Lys Leu Arg Leu Ile Trp Val Thr Ala Arg Met
        130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Thr Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
        195                 200                 205

Val Asp Val Arg Asp Glu Tyr Leu Val His Cys Pro Arg Glu Leu Arg
210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
        275                 280                 285

Gln Thr Ile Thr Leu Asp Tyr Arg Arg Glu Cys Gln His Asp Asp Val
        290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Leu Arg Leu Ser Gly Asn Gly
            340                 345                 350

Leu Glu Ile Asn Arg Gly Arg Thr Glu Trp Arg Lys Lys Pro Thr Arg
        355                 360                 365

Met Asp Tyr Lys Asp His Asp Gly Asp Tyr Lys Asp His Asp Ile Asp
370                 375                 380

Tyr Lys Asp Asp Asp Asp Lys
385                 390

<210> SEQ ID NO 23
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Thr Ala Ser Thr Phe Ser Ala Phe Asn Ala Arg Cys Gly Asp
 1                   5                  10                  15
```

Leu Arg Arg Ser Ala Gly Ser Gly Pro Arg Arg Pro Ala Arg Pro Leu
                20                  25                  30

Pro Val Arg Gly Arg Ala Ile Pro Pro Arg Ile Ile Val Val Ser Ser
            35                  40                  45

Ser Ser Ser Lys Val Asn Pro Leu Lys Thr Glu Ala Val Val Ser Ser
50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Lys Leu Gln Glu Val Gly
            100                 105                 110

Cys Asn His Ala Gln Ser Val Gly Tyr Ser Thr Gly Gly Phe Ser Thr
            115                 120                 125

Thr Pro Thr Met Arg Lys Leu Arg Leu Ile Trp Val Thr Ala Arg Met
            130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Thr Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
            195                 200                 205

Val Asp Val Arg Asp Glu Tyr Leu Val His Cys Pro Arg Glu Leu Arg
210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
            275                 280                 285

Gln Thr Ile Thr Leu Asp Tyr Arg Arg Glu Cys Gln His Asp Asp Val
290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Leu Arg Leu Ser Gly Asn Gly
            340                 345                 350

Leu Glu Ile Asn Arg Gly Arg Thr Glu Trp Arg Lys Lys Pro Thr Arg
            355                 360                 365

Met Asp Tyr Lys Asp His Asp Gly Asp Tyr Lys Asp His Asp Ile Asp
370                 375                 380

Tyr Lys Asp Asp Asp Asp Lys
385                 390

<210> SEQ ID NO 24
<211> LENGTH: 391
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Pro Ala Arg Pro Leu
            20                  25                  30

Pro Val Arg Gly Arg Ala Ile Pro Pro Arg Ile Ile Val Val Ser Ser
            35                  40                  45

Ser Ser Ser Lys Val Asn Pro Leu Lys Thr Glu Ala Val Val Ser Ser
        50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Ser Leu Gln Glu Val Gly
            100                 105                 110

Cys Asn His Ala Gln Ser Val Gly Tyr Ser Thr Gly Gly Phe Ser Thr
        115                 120                 125

Thr Pro Thr Met Arg Lys Leu Arg Leu Ile Trp Val Thr Ala Arg Met
130                 135                 140

His Ile Glu Ile Tyr Lys Tyr Pro Ala Trp Ser Asp Val Val Glu Ile
145                 150                 155                 160

Glu Ser Trp Gly Gln Gly Gly Lys Ile Gly Thr Arg Arg Asp Trp
                165                 170                 175

Ile Leu Arg Asp Tyr Ala Thr Gly Gln Val Ile Gly Arg Ala Thr Ser
                180                 185                 190

Lys Trp Val Met Met Asn Gln Asp Thr Arg Arg Leu Gln Lys Val Asp
            195                 200                 205

Val Asp Val Arg Asp Glu Tyr Leu Val His Cys Pro Arg Glu Leu Arg
210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
        275                 280                 285

Gln Thr Ile Thr Leu Asp Tyr Arg Arg Glu Cys Gln His Asp Asp Val
290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Arg Leu Ser Gly Asn Gly
            340                 345                 350

Leu Glu Ile Asn Arg Gly Arg Thr Glu Trp Arg Lys Lys Pro Thr Arg
        355                 360                 365

Met Asp Tyr Lys Asp His Asp Gly Asp Tyr Lys Asp His Asp Ile Asp
370                 375                 380

Tyr Lys Asp Asp Asp Asp Lys
385                 390
```

<210> SEQ ID NO 25
<211> LENGTH: 391
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Pro Ala Arg Pro Leu
            20                  25                  30

Pro Val Arg Gly Arg Ala Ile Pro Pro Arg Ile Ile Val Val Ser Ser
        35                  40                  45

Ser Ser Ser Lys Val Asn Pro Leu Lys Thr Glu Ala Val Val Ser Ser
50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Leu Leu Gln Glu Val Gly
            100                 105                 110

Cys Asn His Ala Gln Ser Val Gly Tyr Ser Thr Val Gly Phe Ser Thr
        115                 120                 125

Thr Pro Thr Met Arg Lys Leu Arg Leu Ile Trp Val Thr Ala Arg Met
130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Thr Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
        195                 200                 205

Val Asp Val Arg Asp Glu Tyr Leu Val His Cys Pro Arg Glu Leu Arg
210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
        275                 280                 285

Gln Thr Ile Thr Leu Asp Tyr Arg Arg Glu Cys Gln His Asp Asp Val
290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Arg Leu Ser Gly Asn Gly
            340                 345                 350

Leu Glu Ile Asn Arg Gly Arg Thr Glu Trp Arg Lys Lys Pro Thr Arg
        355                 360                 365

```
Met Asp Tyr Lys Asp His Asp Gly Asp Tyr Lys Asp His Asp Ile Asp
        370                 375                 380

Tyr Lys Asp Asp Asp Lys
385                 390

<210> SEQ ID NO 26
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ile Pro Pro Arg Ile Ile Val Val Ser Ser
        35                  40                  45

Ser Ser Ser Lys Val Asn Pro Leu Lys Thr Glu Ala Val Val Ser Ser
50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Leu Leu Gln Glu Val Gly
            100                 105                 110

Cys Asn His Ala Gln Ser Val Gly Tyr Ser Thr Gly Gly Phe Ser Thr
        115                 120                 125

Thr Pro Thr Met Arg Lys Leu Arg Leu Ile Trp Val Thr Ala Arg Met
130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Phe Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
        195                 200                 205

Val Asp Val Arg Asp Glu Tyr Leu Val His Cys Pro Arg Glu Leu Arg
210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
        275                 280                 285

Gln Thr Ile Thr Leu Asp Tyr Arg Arg Glu Cys Gln His Asp Asp Val
290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
```

```
                        325                 330                 335
His Gly Cys Arg Asn Phe Leu His Leu Leu Arg Leu Ser Gly Asn Gly
                340                 345                 350

Leu Glu Ile Asn Arg Gly Arg Thr Glu Trp Arg Lys Pro Thr Arg
            355                 360                 365

Met Asp Tyr Lys Asp His Asp Gly Asp Tyr Lys Asp His Asp Ile Asp
        370                 375                 380

Tyr Lys Asp Asp Asp Lys
385                 390

<210> SEQ ID NO 27
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ile Pro Pro Arg Ile Ile Val Val Ser Ser
        35                  40                  45

Ser Ser Ser Lys Val Asn Pro Leu Lys Thr Glu Ala Val Val Ser Ser
    50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Leu Leu Gln Glu Val Gly
            100                 105                 110

Cys Asn His Ala Gln Ser Val Gly Tyr Ser Thr Gly Gly Phe Ser Thr
        115                 120                 125

Thr Pro Thr Met Arg Lys Leu Arg Leu Ile Trp Val Thr Ala Arg Met
    130                 135                 140

His Ile Glu Ile Tyr Lys Tyr Pro Ala Trp Ser Asp Val Val Glu Ile
145                 150                 155                 160

Glu Ser Trp Gly Gln Gly Gly Lys Ile Gly Ala Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
        195                 200                 205

Val Asp Val Arg Asp Glu Tyr Leu Val His Cys Pro Arg Glu Leu Arg
    210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
        275                 280                 285
```

```
Gln Thr Ile Thr Leu Asp Tyr Arg Arg Glu Cys Gln His Asp Asp Val
            290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Leu Arg Leu Ser Gly Asn Gly
            340                 345                 350

Leu Glu Ile Asn Arg Gly Arg Thr Glu Trp Arg Lys Lys Pro Thr Arg
            355                 360                 365

Met Asp Tyr Lys Asp His Asp Gly Asp Tyr Lys Asp His Asp Ile Asp
370                 375                 380

Tyr Lys Asp Asp Asp Lys
385                 390

<210> SEQ ID NO 28
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Pro Ala Arg Pro Leu
            20                  25                  30

Pro Val Arg Gly Arg Ala Ile Pro Pro Arg Ile Ile Val Val Ser Ser
            35                  40                  45

Ser Ser Ser Lys Val Asn Pro Leu Lys Thr Glu Ala Val Val Ser Ser
        50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Leu Leu Gln Glu Val Gly
            100                 105                 110

Cys Asn His Ala Gln Ser Val Gly Tyr Ser Thr Gly Gly Phe Ser Thr
        115                 120                 125

Thr Pro Thr Met Arg Lys Leu Arg Leu Ile Trp Val Thr Ala Arg Met
130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Lys Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
        195                 200                 205

Val Asp Val Arg Asp Glu Tyr Leu Val His Cys Pro Arg Glu Leu Arg
210                 215                 220

Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255
```

```
Ala Asp Leu Asp Met Asn Gln His Val Asn Asn Val Thr Tyr Ile Gly
            260                 265                 270

Trp Val Leu Glu Ser Met Pro Gln Glu Ile Ile Asp Thr His Glu Leu
            275                 280                 285

Gln Thr Ile Thr Leu Asp Tyr Arg Arg Glu Cys Gln His Asp Asp Val
            290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Leu Arg Leu Ser Gly Asn Gly
            340                 345                 350

Leu Glu Ile Asn Arg Gly Arg Thr Glu Trp Arg Lys Lys Pro Thr Arg
            355                 360                 365

Met Asp Tyr Lys Asp His Asp Gly Asp Tyr Lys Asp His Asp Ile Asp
            370                 375                 380

Tyr Lys Asp Asp Asp Asp Lys
385                 390

<210> SEQ ID NO 29
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ile Pro Pro Arg Ile Ile Val Val Ser Ser
            35                  40                  45

Ser Ser Ser Lys Val Asn Pro Leu Lys Thr Glu Ala Val Val Ser Ser
        50                  55                  60

Gly Leu Ala Asp Arg Leu Arg Leu Gly Ser Leu Thr Glu Asp Gly Leu
65                  70                  75                  80

Ser Tyr Lys Glu Lys Phe Ile Val Arg Cys Tyr Glu Val Gly Ile Asn
                85                  90                  95

Lys Thr Ala Thr Val Glu Thr Ile Ala Asn Leu Leu Gln Glu Val Gly
            100                 105                 110

Cys Asn His Ala Gln Ser Val Gly Tyr Ser Thr Gly Gly Phe Ser Thr
            115                 120                 125

Thr Pro Thr Met Arg Lys Leu Arg Leu Ile Trp Val Thr Ala Arg Met
            130                 135                 140

His Ile Glu Ile Tyr Lys Tyr Pro Ala Trp Ser Asp Val Val Glu Ile
145                 150                 155                 160

Glu Ser Trp Gly Gln Gly Glu Gly Lys Ile Gly Val Arg Arg Asp Trp
                165                 170                 175

Ile Leu Arg Asp Tyr Ala Thr Gly Gln Val Ile Gly Arg Ala Thr Ser
            180                 185                 190

Lys Trp Val Met Met Asn Gln Asp Thr Arg Arg Leu Gln Lys Val Asp
            195                 200                 205

Val Asp Val Arg Asp Glu Tyr Leu Val His Cys Pro Arg Glu Leu Arg
```

```
                210                 215                 220
Leu Ala Phe Pro Glu Glu Asn Asn Ser Ser Leu Lys Lys Ile Ser Lys
225                 230                 235                 240

Leu Glu Asp Pro Ser Gln Tyr Ser Lys Leu Gly Leu Val Pro Arg Arg
                245                 250                 255

Ala Asp Leu Asp Met Asn Gln His Val Asn Asn Val Thr Tyr Ile Gly
                260                 265                 270

Trp Val Leu Glu Ser Met Pro Gln Glu Ile Ile Asp Thr His Glu Leu
            275                 280                 285

Gln Thr Ile Thr Leu Asp Tyr Arg Arg Glu Cys Gln His Asp Asp Val
        290                 295                 300

Val Asp Ser Leu Thr Ser Pro Glu Pro Ser Glu Asp Ala Glu Ala Val
305                 310                 315                 320

Phe Asn His Asn Gly Thr Asn Gly Ser Ala Asn Val Ser Ala Asn Asp
                325                 330                 335

His Gly Cys Arg Asn Phe Leu His Leu Leu Arg Leu Ser Gly Asn Gly
                340                 345                 350

Leu Glu Ile Asn Arg Gly Arg Thr Glu Trp Arg Lys Lys Pro Thr Arg
            355                 360                 365

Met Asp Tyr Lys Asp His Asp Gly Asp Tyr Lys Asp His Asp Ile Asp
        370                 375                 380

Tyr Lys Asp Asp Asp Asp Lys
385                 390

<210> SEQ ID NO 30
<211> LENGTH: 5451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
ccctcaactg cgacgctggg aaccttctcc gggcaggcga tgtgcgtggg tttgcctcct      60
tggcacggct ctacaccgtc gagtacgcca tgaggcggtg atggctgtgt cggttgccac     120
ttcgtccaga gacggcaagt cgtccatcct ctgcgtgtgt ggcgcgacgc tgcagcagtc     180
cctctgcagc agatgagcgt gactttggcc atttcacgca ctcgagtgta cacaatccat     240
ttttcttaaa gcaaatgact gctgattgac cagatactgt aacgctgatt cgctccaga     300 tcgcacagat agcgaccatg ttgctgcgtc tgaaaatctg gattccgaat cgaccctgg     360 cgctccatcc atgcaacaga tggcgacact tgttacaatt cctgtcaccc atcggcatgg     420
agcaggtcca cttagattcc cgatcaccca cgcacatctc gctaatagtc attcgttcgt     480
gtcttcgatc aatctcaagt gagtgtgcat ggatcttggt tgacgatgcg gtatgggttt     540
gcgccgctgg ctgcagggtc tgcccaaggc aagctaaccc agctcctctc ccgacaata     600 ctctcgcagg caaagccggt cacttgcctt ccagattgcc ataaactca attatggcct     660 ctgtcatgcc atccatgggt ctgatgaatg gtcacgctcg tgtcctgacc gttccccagc     720
ctctggcgtc cctgccccg cccaccagcc cacgccgcgc ggcagtcgct gccaaggctg     780
tctcggaggt accctttctt gcgctatgac acttccagca aaaggtaggg cgggctgcga     840
gacggcttcc cggcgctgca tgcaacaccg atgatgcttc gaccccccga agctccttcg     900
gggctgcatg ggcgctccga tgccgctcca gggcgagcgc tgtttaaata gccaggcccc     960
cgattgcaaa gacattatag cgagctacca aagccatatt caaacaccta gatcactacc    1020
```

```
acttctacac aggccactcg agcttgtgat cgcactccgc taaggggcg cctcttcctc      1080
ttcgtttcag tcacaacccg caaactctag aatatcaatg atcgagcagg acggcctcca    1140
cgccggctcc cccgccgcct gggtggagcg cctgttcggc tacgactggg cccagcagac    1200
catcggctgc tccgacgccg ccgtgttccg cctgtccgcc cagggccgcc ccgtgctgtt    1260
cgtgaagacc gacctgtccg gcgccctgaa cgagctgcag gacgaggccg cccgcctgtc    1320
ctggctggcc accaccggcg tgccctgcgc cgccgtgctg gacgtggtga ccgaggccgg    1380
ccgcgactgg ctgctgctgg gcgaggtgcc cggccaggac ctgctgtcct cccacctggc    1440
ccccgccgag aaggtgtcca tcatggccga cgccatgcgc cgcctgcaca ccctggaccc    1500
cgccacctgc cccttcgacc accaggccaa gcaccgcatc gagcgcgccc gcacccgcat    1560
ggaggccggc ctggtggacc aggacgacct ggacgaggag caccagggcc tggccccgc    1620
cgagctgttc gcccgcctga aggcccgcat gcccgacggc gaggacctgg tggtgaccca    1680
cggcgacgcg tgcctgccca acatcatggt ggagaacggc cgcttctccg gcttcatcga    1740
ctgcggccgc ctgggcgtgg ccgaccgcta ccaggacatc gccctggcca ccgcgacat    1800
cgccgaggag ctgggcggcg agtgggccga ccgcttcctg gtgctgtacg gcatcgccgc    1860
ccccgactcc cagcgcatcg ccttctaccg cctgctggac gagttcttct gacaattgac    1920
gcccgcgcgg cgcacctgac ctgttctctc gagggcgcct gttctgcctt gcgaaacaag    1980
cccctggagc atgcgtgcat gatcgtctct ggcgccccgc cgcgcggttt gtcgccctcg    2040
cgggcgccgc ggccgcgggg gcgcattgaa attgttgcaa accccacctg acagattgag    2100
ggcccaggca ggaaggcgtt gagatggagg tacaggagtc aagtaactga aagtttttat    2160
gataactaac aacaaagggt cgtttctggc cagcgaatga caagaacaag attccacatt    2220
tccgtgtaga ggcttgccat cgaatgtgag cgggcgggcc gcggacccga caaaacccctt   2280
acgacgtggt aagaaaaacg tggcgggcac tgtccctgta gcctgaagac cagcaggaga   2340
cgatcggaag catcacagca caggatcccg cgtctcgaac agagcgcgca gaggaacgct    2400
gaaggtctcg cctctgtcgc acctcagcgc ggcatacacc acaataacca cctgacgaat    2460
gcgcttggtt cttcgtccat tagcgaagcg tccggttcac acacgtgcca cgttggcgag    2520
gtggcaggtg acaatgatcg gtggagctga tggtcgaaac gttcacagcc tagggatatc    2580
gtgaaaactc gctcgaccgc ccgcgtcccg caggcagcga tgacgtgtgc gtgacctggg    2640
tgtttcgtcg aaaggccagc aaccccaaat cgcaggcgat ccggagattg ggatctgatc    2700
cgagcttgga ccagatcccc cacgatgcgg cacgggaact gcatcgactc ggcgcggaac    2760
ccagctttcg taaatgccag attggtgtcc gataccttga tttgccatca gcgaaacaag    2820
acttcagcag cgagcgtatt tggcgggcgt gctaccaggg ttgcatacat tgcccatttc    2880
tgtctggacc gctttaccgg cgcagagggt gagttgatgg ggttggcagg catcgaaacg    2940
cgcgtgcatg tgtgtgtgt ctgttttcgg ctgcacaatt tcaatagtcg gatgggcgac    3000
ggtagaattg ggtgttgcgc tcgcgtgcat gcctcgcccc gtcgggtgtc atgaccggga    3060
ctggaatccc ccctcgcgac cctcctgcta acgctcccga ctctcccgcc cgcgcgcagg    3120
atagactcta gttcaaccaa tcgacaacta gtatggccac cgcatccact ttctcggcgt    3180
tcaatgcccg ctgcggcgac ctgcgtcgct cggcgggctc cgggcccgg cgcccagcga     3240
ggcccctccc cgtgcgcggg cgcgccatcc cccccgcat catcgtggtg tcctcctcct    3300
cctccaaggt gaacccctg aagaccgagg ccgtggtgtc ctccggcctg gccgaccgcc    3360
```

-continued

| | |
|---|---|
| tgcgcctggg ctccctgacc gaggacggcc tgtcctacaa ggagaagttc atcgtgcgct | 3420 |
| gctacgaggt gggcatcaac aagaccgcca ccgtggagac catcgccaac ctgctgcagg | 3480 |
| aggtgggctg caaccacgcc cagtccgtgg gctactccac cggcggcttc tccaccaccc | 3540 |
| ccaccatgcg caagctgcgc ctgatctggg tgaccgcccg catgcacatc gagatctaca | 3600 |
| agtaccccgc ctggtccgac gtggtggaga tcgagtcctg gggccagggc gagggcaaga | 3660 |
| tcggcacccg ccgcgactgg atcctgcgcg actacgccac cggccaggtg atcggccgcg | 3720 |
| ccacctccaa gtgggtgatg atgaaccagg acacccgccg cctgcagaag gtggacgtgg | 3780 |
| acgtgcgcga cgagtacctg gtgcactgcc ccgcgagct cgcgcctggcc ttccccgagg | 3840 |
| agaacaactc ctccctgaag aagatctcca agctggagga cccctcccag tactccaagc | 3900 |
| tgggcctggt gccccgccgc gccgacctgg acatgaacca gcacgtgaac aacgtgacct | 3960 |
| acatcggctg ggtgctggag tccatgcccc aggagatcat cgacacccac gagctgcaga | 4020 |
| ccatcaccct ggactaccgc cgcgagtgcc agcacgacga cgtggtggac tccctgacct | 4080 |
| cccccgagcc ctccgaggac gccgaggccg tgttcaacca caacggcacc aacggctccg | 4140 |
| ccaacgtgtc cgccaacgac cacggctgcc gcaacttcct gcacctgctg cgcctgtccg | 4200 |
| gcaacggcct ggagatcaac cgcggccgca ccgagtggcg caagaagccc acccgcatgg | 4260 |
| actacaagga ccacgacggc gactacaagg accacgacat cgactacaag gacgacgacg | 4320 |
| acaagtgaat cgatgcagca gcagctcgga tagtatcgac acactctgga cgctggtcgt | 4380 |
| gtgatggact gttgccgcca cacttgctgc cttgacctgt gaatatccct gccgcttta | 4440 |
| tcaaacagcc tcagtgtgtt tgatcttgtg tgtacgcgct tttgcgagtt gctagctgct | 4500 |
| tgtgctattt gcgaatacca ccccagcat ccccttccct cgtttcatat cgcttgcatc | 4560 |
| ccaaccgcaa cttatctacg ctgtcctgct atccctcagc gctgctcctg ctcctgctca | 4620 |
| ctgcccctcg cacagccttg gtttgggctc cgcctgtatt ctcctggtac tgcaacctgt | 4680 |
| aaaccagcac tgcaatgctg atgcacggga agtagtggga tgggaacaca atgggaaagc | 4740 |
| ttgagctcca gcgccatgcc acgccctttg atggcttcaa gtacgattac ggtgttggat | 4800 |
| tgtgtgtttg ttgcgtagtg tgcatggttt agaataatac acttgatttc ttgctcacgg | 4860 |
| caatctcggc ttgtccgcag gttcaacccc atttcggagt ctcaggtcag ccgcgcaatg | 4920 |
| accagccgct acttcaagga cttgcacgac aacgccgagg tgagctatgt ttaggacttg | 4980 |
| attggaaatt gtcgtcgacg catattgcg ctccgcgaca gcacccaagc aaaatgtcaa | 5040 |
| gtgcgttccg atttgcgtcc gcaggtcgat gttgtgatcg tcggcgccgg atccgccggt | 5100 |
| ctgtcctgcg cttacgagct gaccaagcac cctgacgtcc gggtacgcga gctgagattc | 5160 |
| gattagacat aaattgaaga ttaaacccgt agaaaatttt gatggtcgcg aaactgtgct | 5220 |
| cgattgcaag aaattgatcg tcctccactc cgcaggtcgc catcatcgag cagggcgttg | 5280 |
| ctcccggcgg cggcgcctgg ctgggggac agctgttctc ggccatgtgt gtacgtagaa | 5340 |
| ggatgaattt cagctggttt tcgttgcaca gctgtttgtg catgatttgt ttcagactat | 5400 |
| tgttgaatgt ttttagattt cttaggatgc atgatttgtc tgcatgcgac t | 5451 |

<210> SEQ ID NO 31
<211> LENGTH: 1176
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 31

```
atggccaccg catccacttt ctcggcgttc aatgcccgct gcggcgacct gcgtcgctcg      60
gcgggctccg ggccccggcg cccagcgagg cccctccccg tgcgcgggcg cgccatcccc     120
ccccgcatca tcgtggtgtc ctcctcctcc tccaaggtga accccctgaa gaccgaggcc     180
gtggtgtcct ccggcctggc cgaccgcctg cgcctgggct ccctgaccga ggacggcctg     240
tcctacaagg agaagttcat cgtgcgctgc tacgaggtgg gcatcaacaa gaccgccacc     300
gtggagacca tcgccaacct gctgcaggag gtgggctgca accacgccca gtccgtgggc     360
tactccaccg gcggcttcgc caccaccccc accatgcgca agctgcgcct gatctgggtg     420
accgcccgca tgcacatcga gatctacaag taccccgcct ggtccgacgt ggtggagatc     480
gagtcctggg gccagggcga gggcaagatc ggcacccgcc gcgactggat cctgcgcgac     540
tacgccaccg gccaggtgat cggccgcgcc acctccaagt gggtgatgat gaaccaggac     600
acccgccgcc tgcagaaggt ggacgcggac gtgcgcgacg agtacctggt gcactgcccc     660
cgcgagctgc gcctggcctt ccccgaggag aacaactcct ccctgaagaa gatctccaag     720
ctggaggacc cctcccagta ctccaagctg ggcctggtgc ccgccgcgc cgacctggac      780
atgaaccagc acgtgaacaa cgtgacctac atcggctggg tgctggagtc catgcccag    840
gagatcatcg acacccacga gctgcagacc atcaccctgg actaccgccg cgagtgccag     900
cacgacgacg tggtggactc cctgacctcc cccgagccct ccgaggacgc cgaggccgtg     960
ttcaaccaca acggcaccaa cggctccgcc aacgtgtccg ccaacgacca cggctgccgc    1020
aacttcctgc acctgctgcg cctgtccggc aacggcctgg agatcaaccg cggccgcacc    1080
gagtggcgca agaagcccac ccgcatggac tacaaggacc acgacggcga ctacaaggac    1140
cacgacatcg actacaagga cgacgacgac aagtga                              1176
```

<210> SEQ ID NO 32
<211> LENGTH: 1176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
atggccaccg catccacttt ctcggcgttc aatgcccgct gcggcgacct gcgtcgctcg      60
gcgggctccg ggccccggcg cccagcgagg cccctccccg tgcgcgggcg cgccatcccc     120
ccccgcatca tcgtggtgtc ctcctcctcc tccaaggtga accccctgaa gaccgaggcc     180
gtggtgtcct ccggcctggc cgaccgcctg cgcctgggct ccctgaccga ggacggcctg     240
tcctacaagg agaagttcat cgtgcgctgc tacgaggtgg gcatcaacaa gaccgccacc     300
gtggagacca tcgccaacct gctgcaggag gtgggctgca accacgccca gtccgtgggc     360
tactccaccg gcggcttcgt caccaccccc accatgcgca agctgcgcct gatctgggtg     420
accgcccgca tgcacatcga gatctacaag taccccgcct ggtccgacgt ggtggagatc     480
gagtcctggg gccagggcga gggcaagatc ggcacccgcc gcgactggat cctgcgcgac     540
tacgccaccg gccaggtgat cggccgcgcc acctccaagt gggtgatgat gaaccaggac     600
acccgccgcc tgcagaaggt ggacgcggac gtgcgcgacg agtacctggt gcactgcccc     660
cgcgagctgc gcctggcctt ccccgaggag aacaactcct ccctgaagaa gatctccaag     720
ctggaggacc cctcccagta ctccaagctg ggcctggtgc ccgccgcgc cgacctggac      780
```

```
atgaaccagc acgtgaacaa cgtgacctac atcggctggg tgctggagtc catgccccag      840
gagatcatcg acacccacga gctgcagacc atcaccctgg actaccgccg cgagtgccag      900
cacgacgacg tggtggactc cctgacctcc cccgagccct ccgaggacgc cgaggccgtg      960
ttcaaccaca acggcaccaa cggctccgcc aacgtgtccg ccaacgacca cggctgccgc     1020
aacttcctgc acctgctgcg cctgtccggc aacggcctgg agatcaaccg cggccgcacc     1080
gagtggcgca agaagcccac ccgcatggac tacaaggacc acgacggcga ctacaaggac     1140
cacgacatcg actacaagga cgacgacgac aagtga                              1176
```

<210> SEQ ID NO 33
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
atggccaccg catccacttt ctcggcgttc aatgcccgct gcggcgacct gcgtcgctcg       60
gcgggctccg ggccccggcg cccagcgagg cccctccccg tgcgcgggcg cgccatcccc      120
ccccgcatca tcgtggtgtc ctcctcctcc tccaaggtga accccctgaa gaccgaggcc      180
gtggtgtcct ccggcctggc cgaccgcctg cgcctgggct ccctgaccga ggacggcctg      240
tcctacaagg agaagttcat cgtgcgctgc tacgaggtgg gcatcaacaa gaccgccacc      300
gtggagacca tcgccaacct gctgcaggag gtggcgtgca accacgccca gtccgtgggc      360
tactccaccg gcggcttctc caccaccccc accatgcgca agctgcgcct gatctgggtg      420
accgcccgca tgcacatcga gatctacaag taccccgcct ggtccgacgt ggtggagatc      480
gagtcctggg gccagggcga gggcaagatc ggcacccgcc gcgactggat cctgcgcgac      540
tacgccaccg gccaggtgat cggccgcgcc acctccaagt gggtgatgat gaaccaggac      600
acccgccgcc tgcagaaggt ggacgtggac gtgcgcgacg agtacctggt gcactgcccc      660
cgcgagctgc gcctggcctt ccccgaggag aacaactcct ccctgaagaa gatctccaag      720
ctggaggacc cctcccagta ctccaagctg ggcctggtgc ccgccgcgc cgacctggac      780 atgaaccagc acgtgaacaa cgtgacctac atcggctggg tgctggagtc catgccccag      840
gagatcatcg acacccacga gctgcagacc atcaccctgg actaccgccg cgagtgccag      900
cacgacgacg tggtggactc cctgacctcc cccgagccct ccgaggacgc cgaggccgtg      960
ttcaaccaca acggcaccaa cggctccgcc aacgtgtccg ccaacgacca cggctgccgc     1020
aacttcctgc acctgctgcg cctgtccggc aacggcctgg agatcaaccg cggccgcacc     1080
gagtggcgca agaagcccac ccgcatggac tacaaggacc acgacggcga ctacaaggac     1140
cacgacatcg actacaagga cgacgacgac aagtga                              1176
```

<210> SEQ ID NO 34
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
atggccaccg catccacttt ctcggcgttc aatgcccgct gcggcgacct gcgtcgctcg       60
gcgggctccg ggccccggcg cccagcgagg cccctccccg tgcgcgggcg cgccatcccc      120
```

```
cccgcatca tcgtggtgtc ctcctcctcc tccaaggtga accccctgaa gaccgaggcc    180
gtggtgtcct ccggcctggc cgaccgcctg cgcctgggct ccctgaccga ggacggcctg    240
tcctacaagg agaagttcat cgtgcgctgc tacgaggtgg gcatcaacaa gaccgccacc    300
gtggagacca tcgccaacct gctgcaggag gtgacgtgca accacgccca gtccgtgggc    360
tactccaccg gcggcttctc caccaccccc accatgcgca agctgcgcct gatctgggtg    420
accgcccgca tgcacatcga gatctacaag taccccgcct ggtccgacgt ggtggagatc    480
gagtcctggg gccagggcga gggcaagatc ggcacccgcc gcgactggat cctgcgcgac    540
tacgccaccg gccaggtgat cggccgcgcc acctccaagt gggtgatgat gaaccaggac    600
acccgccgcc tgcagaaggt ggacgtggac gtgcgcgacg agtacctggt gcactgcccc    660
cgcgagctgc gcctggcctt ccccgaggag aacaactcct ccctgaagaa gatctccaag    720
ctggaggacc cctcccagta ctccaagctg gcctggtgc cccgccgcgc cgacctggac    780
atgaaccagc acgtgaacaa cgtgacctac atcggctggg tgctggagtc catgcccag    840 gagatcatcg acacccacga gctgcagacc atcaccctgg actaccgccg cgagtgccag    900
cacgacgacg tggtggactc cctgacctcc cccgagccct ccgaggacgc cgaggccgtg    960
ttcaaccaca acggcaccaa cggctccgcc aacgtgtccg ccaacgacca cggctgccgc   1020
aacttcctgc acctgctgcg cctgtccggc aacggcctgg agatcaaccg cggccgcacc   1080
gagtggcgca agaagcccac ccgcatggac tacaaggacc acgacggcga ctacaaggac   1140
cacgacatcg actacaagga cgacgacgac aagtga                            1176
```

<210> SEQ ID NO 35
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
atggccaccg catccacttt ctcggcgttc aatgcccgct gcggcgacct gcgtcgctcg     60
gcgggctccg ggccccggcg cccagcgagg cccctccccg tgcgcgggcg cgccatcccc    120 cccgcatca tcgtggtgtc ctcctcctcc tccaaggtga accccctgaa gaccgaggcc    180
gtggtgtcct ccggcctggc cgaccgcctg cgcctgggct ccctgaccga ggacggcctg    240
tcctacaagg agaagttcat cgtgcgctgc tacgaggtgg gcatcaacaa gaccgccacc    300
gtggagacca tcgccaacct gctgcaggag gtggtgtgca accacgccca gtccgtgggc    360
tactccaccg gcggcttctc caccaccccc accatgcgca agctgcgcct gatctgggtg    420
accgcccgca tgcacatcga gatctacaag taccccgcct ggtccgacgt ggtggagatc    480
gagtcctggg gccagggcga gggcaagatc ggcacccgcc gcgactggat cctgcgcgac    540
tacgccaccg gccaggtgat cggccgcgcc acctccaagt gggtgatgat gaaccaggac    600
acccgccgcc tgcagaaggt ggacgtggac gtgcgcgacg agtacctggt gcactgcccc    660
cgcgagctgc gcctggcctt ccccgaggag aacaactcct ccctgaagaa gatctccaag    720
ctggaggacc cctcccagta ctccaagctg gcctggtgc cccgccgcgc cgacctggac    780
atgaaccagc acgtgaacaa cgtgacctac atcggctggg tgctggagtc catgcccag    840 gagatcatcg acacccacga gctgcagacc atcaccctgg actaccgccg cgagtgccag    900
cacgacgacg tggtggactc cctgacctcc cccgagccct ccgaggacgc cgaggccgtg    960
```

```
ttcaaccaca acggcaccaa cggctccgcc aacgtgtccg ccaacgacca cggctgccgc   1020
aacttcctgc acctgctgcg cctgtccggc aacggcctgg agatcaaccg cggccgcacc   1080
gagtggcgca agaagcccac ccgcatggac tacaaggacc acgacggcga ctacaaggac   1140
cacgacatcg actacaagga cgacgacgac aagtga                             1176
```

<210> SEQ ID NO 36
<211> LENGTH: 1176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
atggccaccg catccacttt ctcggcgttc aatgcccgct gcggcgacct gcgtcgctcg    60
gcgggctccg ggccccggcg cccagcgagg cccctccccg tgcgcgggcg cgccatcccc   120
ccccgcatca tcgtggtgtc ctcctcctcc tccaaggtga accccctgaa gaccgaggcc   180
gtggtgtcct ccggcctggc cgaccgcctg cgcctgggct ccctgaccga ggacggcctg   240
tcctacaagg agaagttcat cgtgcgctgc tacgaggtgg gcatcaacaa gaccgccacc   300
gtggagacca tcgccaacct gctgcaggag gtgggctgca accacgccca gtccgtgggc   360
tactccaccg ccggcttctc caccaccccc accatgcgca agctgcgcct gatctgggtg   420
accgcccgca tgcacatcga gatctacaag taccccgcct ggtccgacgt ggtggagatc   480
gagtcctggg ccagggcgag gggcaagatc ggcacccgcc gcgactggat cctgcgcgac   540
tacgccaccg gccaggtgat cggccgcgcc acctccaagt gggtgatgat gaaccaggac   600
acccgccgcc tgcagaaggt ggacgtggac gtgcgcgacg agtacctggt gcactgcccc   660
cgcgagctgc gcctggcctt ccccgaggag aacaactcct ccctgaagaa gatctccaag   720
ctggaggacc cctcccagta ctccaagctg ggcctggtgc ccgccgcgc cgacctggac   780 atgaaccagc acgtgaacaa cgtgacctac atcggctggg tgctggagtc catgccccag   840
gagatcatcg acacccacga gctgcagacc atcaccctgg actaccgccg cgagtgccag   900
cacgacgacg tggtggactc cctgacctcc cccgagccct ccgaggacgc cgaggccgtg   960
ttcaaccaca acggcaccaa cggctccgcc aacgtgtccg ccaacgacca cggctgccgc  1020
aacttcctgc acctgctgcg cctgtccggc aacggcctgg agatcaaccg cggccgcacc  1080
gagtggcgca agaagcccac ccgcatggac tacaaggacc acgacggcga ctacaaggac  1140
cacgacatcg actacaagga cgacgacgac aagtga                            1176
```

<210> SEQ ID NO 37
<211> LENGTH: 1176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
atggccaccg catccacttt ctcggcgttc aatgcccgct gcggcgacct gcgtcgctcg    60
gcgggctccg ggccccggcg cccagcgagg cccctccccg tgcgcgggcg cgccatcccc   120
ccccgcatca tcgtggtgtc ctcctcctcc tccaaggtga accccctgaa gaccgaggcc   180
gtggtgtcct ccggcctggc cgaccgcctg cgcctgggct ccctgaccga ggacggcctg   240
```

| | |
|---|---:|
| tcctacaagg agaagttcat cgtgcgctgc tacgaggtgg gcatcaacaa gaccgccacc | 300 |
| gtggagacca tcgccaactt cctgcaggag gtgggctgca accacgccca gtccgtgggc | 360 |
| tactccaccg gcggcttctc caccacccc accatgcgca agctgcgcct gatctgggtg | 420 |
| accgcccgca tgcacatcga gatctacaag taccccgcct ggtccgacgt ggtggagatc | 480 |
| gagtcctggg gccagggcga gggcaagatc ggcacccgcc gcgactggat cctgcgcgac | 540 |
| tacgccaccg gccaggtgat cggccgcgcc acctccaagt gggtgatgat gaaccaggac | 600 |
| acccgccgcc tgcagaaggt ggacgtggac gtgcgcgacg agtacctggt gcactgcccc | 660 |
| cgcgagctgc gcctggcctt ccccgaggag aacaactcct ccctgaagaa gatctccaag | 720 |
| ctggaggacc cctcccagta ctccaagctg ggcctggtgc ccgccgcgc cgacctggac | 780 |
| atgaaccagc acgtgaacaa cgtgacctac atcggctggg tgctggagtc catgccccag | 840 |
| gagatcatcg acacccacga gctgcagacc atcaccctgg actaccgccg cgagtgccag | 900 |
| cacgacgacg tggtggactc cctgacctcc cccgagccct ccgaggacgc cgaggccgtg | 960 |
| ttcaaccaca acggcaccaa cggctccgcc aacgtgtccg ccaacgacca cggctgccgc | 1020 |
| aacttcctgc acctgctgcg cctgtccggc aacggcctgg agatcaaccg cggccgcacc | 1080 |
| gagtggcgca agaagcccac ccgcatggac tacaaggacc acgacggcga ctacaaggac | 1140 |
| cacgacatcg actacaagga cgacgacgac aagtga | 1176 |

<210> SEQ ID NO 38
<211> LENGTH: 1176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

| | |
|---|---:|
| atggccaccg catccacttt ctcggcgttc aatgcccgct gcggcgacct gcgtcgctcg | 60 |
| gcgggctccg ggccccggcg cccagcgagg cccctccccg tgcgcgggcg cgccatcccc | 120 |
| ccccgcatca tcgtggtgtc ctcctcctcc tccaaggtga accccctgaa gaccgaggcc | 180 |
| gtggtgtcct ccggcctggc cgaccgcctg cgcctgggct ccctgaccga ggacggcctg | 240 |
| tcctacaagg agaagttcat cgtgcgctgc tacgaggtgg gcatcaacaa gaccgccacc | 300 |
| gtggagacca tcgccaacaa gctgcaggag gtgggctgca accacgccca gtccgtgggc | 360 |
| tactccaccg gcggcttctc caccacccc accatgcgca agctgcgcct gatctgggtg | 420 |
| accgcccgca tgcacatcga gatctacaag taccccgcct ggtccgacgt ggtggagatc | 480 |
| gagtcctggg gccagggcga gggcaagatc ggcacccgcc gcgactggat cctgcgcgac | 540 |
| tacgccaccg gccaggtgat cggccgcgcc acctccaagt gggtgatgat gaaccaggac | 600 |
| acccgccgcc tgcagaaggt ggacgtggac gtgcgcgacg agtacctggt gcactgcccc | 660 |
| cgcgagctgc gcctggcctt ccccgaggag aacaactcct ccctgaagaa gatctccaag | 720 |
| ctggaggacc cctcccagta ctccaagctg ggcctggtgc ccgccgcgc cgacctggac | 780 |
| atgaaccagc acgtgaacaa cgtgacctac atcggctggg tgctggagtc catgccccag | 840 |
| gagatcatcg acacccacga gctgcagacc atcaccctgg actaccgccg cgagtgccag | 900 |
| cacgacgacg tggtggactc cctgacctcc cccgagccct ccgaggacgc cgaggccgtg | 960 |
| ttcaaccaca acggcaccaa cggctccgcc aacgtgtccg ccaacgacca cggctgccgc | 1020 |
| aacttcctgc acctgctgcg cctgtccggc aacggcctgg agatcaaccg cggccgcacc | 1080 |

-continued

| | |
|---|---|
| gagtggcgca agaagcccac ccgcatggac tacaaggacc acgacggcga ctacaaggac | 1140 |
| cacgacatcg actacaagga cgacgacgac aagtga | 1176 |

<210> SEQ ID NO 39
<211> LENGTH: 1176
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39

| | |
|---|---|
| atggccaccg catccacttt ctcggcgttc aatgcccgct gcggcgacct gcgtcgctcg | 60 |
| gcgggctccg ggccccggcg cccagcgagg cccctccccg tgcgcgggcg cgccatcccc | 120 |
| ccccgcatca tcgtggtgtc ctcctcctcc tccaaggtga accccctgaa gaccgaggcc | 180 |
| gtggtgtcct ccggcctggc cgaccgcctg cgcctgggct ccctgaccga ggacggcctg | 240 |
| tcctacaagg agaagttcat cgtgcgctgc tacgaggtgg gcatcaacaa gaccgccacc | 300 |
| gtggagacca tcgccaactc gctgcaggag gtgggctgca accacgccca gtccgtgggc | 360 |
| tactccaccg gcggcttctc caccaccccc accatgcgca agctgcgcct gatctgggtg | 420 |
| accgcccgca tgcacatcga gatctacaag taccccgcct ggtccgacgt ggtggagatc | 480 |
| gagtcctggg gccagggcga gggcaagatc ggcacccgcc gcgactggat cctgcgcgac | 540 |
| tacgccaccg gccaggtgat cggccgcgcc acctccaagt gggtgatgat gaaccaggac | 600 |
| acccgccgcc tgcagaaggt ggacgtggac gtgcgcgacg agtacctggt gcactgcccc | 660 |
| cgcgagctgc gcctggcctt ccccgaggag aacaactcct ccctgaagaa gatctccaag | 720 |
| ctggaggacc cctcccagta ctccaagctg ggcctggtgc ccgccgcgc cgacctggac | 780 |
| atgaaccagc acgtgaacaa cgtgacctac atcggctggg tgctggagtc catgcccag | 840 |
| gagatcatcg acacccacga gctgcagacc atcaccctgg actaccgccg cgagtgccag | 900 |
| cacgacgacg tggtggactc cctgacctcc cccgagccct ccgaggacgc cgaggccgtg | 960 |
| ttcaaccaca acggcaccaa cggctccgcc aacgtgtccg ccaacgacca cggctgccgc | 1020 |
| aacttcctgc acctgctgcg cctgtccggc aacggcctgg agatcaaccg cggccgcacc | 1080 |
| gagtggcgca agaagcccac ccgcatggac tacaaggacc acgacggcga ctacaaggac | 1140 |
| cacgacatcg actacaagga cgacgacgac aagtga | 1176 |

<210> SEQ ID NO 40
<211> LENGTH: 1176
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40

| | |
|---|---|
| atggccaccg catccacttt ctcggcgttc aatgcccgct gcggcgacct gcgtcgctcg | 60 |
| gcgggctccg ggccccggcg cccagcgagg cccctccccg tgcgcgggcg cgccatcccc | 120 |
| ccccgcatca tcgtggtgtc ctcctcctcc tccaaggtga accccctgaa gaccgaggcc | 180 |
| gtggtgtcct ccggcctggc cgaccgcctg cgcctgggct ccctgaccga ggacggcctg | 240 |
| tcctacaagg agaagttcat cgtgcgctgc tacgaggtgg gcatcaacaa gaccgccacc | 300 |
| gtggagacca tcgccaacct gctgcaggag gtgggctgca accacgccca gtccgtgggc | 360 |
| tactccaccg tcggcttctc caccaccccc accatgcgca agctgcgcct gatctgggtg | 420 |

```
accgcccgca tgcacatcga gatctacaag taccccgcct ggtccgacgt ggtggagatc    480
gagtcctggg gccagggcga gggcaagatc ggcacccgcc gcgactggat cctgcgcgac    540
tacgccaccg gccaggtgat cggccgcgcc acctccaagt gggtgatgat gaaccaggac    600
acccgccgcc tgcagaaggt ggacgtggac gtgcgcgacg agtacctggt gcactgcccc    660
cgcgagctgc gcctggcctt ccccgaggag aacaactcct ccctgaagaa gatctccaag    720
ctggaggacc cctcccagta ctccaagctg gcctggtgc cccgccgcgc cgacctggac     780
atgaaccagc acgtgaacaa cgtgacctac atcggctggg tgctggagtc catgccccag    840
gagatcatcg acacccacga gctgcagacc atcaccctgg actaccgccg cgagtgccag    900
cacgacgacg tggtggactc cctgacctcc cccgagccct ccgaggacgc cgaggccgtg    960
ttcaaccaca acggcaccaa cggctccgcc aacgtgtccg ccaacgacca cggctgccgc   1020
aacttcctgc acctgctgcg cctgtccggc aacggcctgg agatcaaccg cggccgcacc   1080
gagtggcgca agaagcccac ccgcatggac tacaaggacc acgacggcga ctacaaggac   1140
cacgacatcg actacaagga cgacgacgac aagtga                             1176
```

<210> SEQ ID NO 41
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
atggccaccg catccacttt ctcggcgttc aatgcccgct gcggcgacct gcgtcgctcg     60
gcgggctccg ggccccggcg cccagcgagg cccctcccg tgcgcgggcg cgccatcccc     120
ccccgcatca tcgtggtgtc ctcctcctcc tccaaggtga accccctgaa gaccgaggcc    180
gtggtgtcct ccggcctggc cgaccgcctg cgcctgggct ccctgaccga ggacggcctg    240
tcctacaagg agaagttcat cgtgcgctgc tacgaggtgg gcatcaacaa gaccgccacc    300
gtggagacca tcgccaacct gctgcaggag gtgggctgca accacgccca gtccgtgggc    360
tactccaccg gcggcttctc caccaccccc accatgcgca agctgcgcct gatctgggtg    420
accgcccgca tgcacatcga gatctacaag taccccgcct ggtccgacgt ggtggagatc    480
gagtcctggg gccagggcga gggcaagatc ggcttccgcc gcgactggat cctgcgcgac    540
tacgccaccg gccaggtgat cggccgcgcc acctccaagt gggtgatgat gaaccaggac    600
acccgccgcc tgcagaaggt ggacgtggac gtgcgcgacg agtacctggt gcactgcccc    660
cgcgagctgc gcctggcctt ccccgaggag aacaactcct ccctgaagaa gatctccaag    720
ctggaggacc cctcccagta ctccaagctg gcctggtgc cccgccgcgc cgacctggac     780
atgaaccagc acgtgaacaa cgtgacctac atcggctggg tgctggagtc catgccccag    840
gagatcatcg acacccacga gctgcagacc atcaccctgg actaccgccg cgagtgccag    900
cacgacgacg tggtggactc cctgacctcc cccgagccct ccgaggacgc cgaggccgtg    960
ttcaaccaca acggcaccaa cggctccgcc aacgtgtccg ccaacgacca cggctgccgc   1020
aacttcctgc acctgctgcg cctgtccggc aacggcctgg agatcaaccg cggccgcacc   1080
gagtggcgca agaagcccac ccgcatggac tacaaggacc acgacggcga ctacaaggac   1140
cacgacatcg actacaagga cgacgacgac aagtga                             1176
```

<210> SEQ ID NO 42
<211> LENGTH: 1176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
atggccaccg catccacttt ctcggcgttc aatgcccgct gcggcgacct gcgtcgctcg      60
gcgggctccg ggccccggcg cccagcgagg cccctccccg tgcgcgggcg cgccatcccc     120
ccccgcatca tcgtggtgtc ctcctcctcc tccaaggtga acccctgaa gaccgaggcc      180
gtggtgtcct ccggcctggc cgaccgcctg cgcctgggct ccctgaccga ggacggcctg     240
tcctacaagg agaagttcat cgtgcgctgc tacgaggtgg gcatcaacaa gaccgccacc     300
gtggagacca tcgccaacct gctgcaggag gtgggctgca ccacgcccca gtccgtgggc     360
tactccaccg gcggcttctc caccaccccc accatgcgca agctgcgcct gatctgggtg     420
accgcccgca tgcacatcga gatctacaag taccccgcct ggtccgacgt ggtggagatc     480
gagtcctggg ccagggcga gggcaagatc ggcgcgcgcc gcgactggat cctgcgcgac     540
tacgccaccg ccaggtgat cggccgcgcc acctccaagt gggtgatgat gaaccaggac      600
acccgccgcc tgcagaaggt ggacgtggac gtgcgcgacg agtacctggt gcactgcccc     660
cgcgagctgc gcctggcctt ccccgaggag aacaactcct ccctgaagaa gatctccaag     720
ctggaggacc cctcccagta ctccaagctg ggcctggtgc ccgccgcgc cgacctggac      780
atgaaccagc acgtgaacaa cgtgacctac atcggctggg tgctggagtc catgcccag      840
gagatcatcg acacccacga gctgcagacc atcaccctgg actaccgccg cgagtgccag     900
cacgacgacg tggtggactc cctgacctcc cccgagccct ccgaggacgc cgaggccgtg     960
ttcaaccaca acggcaccaa cggctccgcc aacgtgtccg ccaacgacca cggctgccgc    1020
aacttcctgc acctgctgcg cctgtccggc aacggcctgg agatcaaccg cggccgcacc    1080
gagtggcgca agaagcccac ccgcatggac tacaaggacc acgacggcga ctacaaggac    1140
cacgacatcg actacaagga cgacgacgac aagtga                              1176
```

<210> SEQ ID NO 43
<211> LENGTH: 1176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
atggccaccg catccacttt ctcggcgttc aatgcccgct gcggcgacct gcgtcgctcg      60
gcgggctccg ggccccggcg cccagcgagg cccctccccg tgcgcgggcg cgccatcccc     120
ccccgcatca tcgtggtgtc ctcctcctcc tccaaggtga acccctgaa gaccgaggcc      180
gtggtgtcct ccggcctggc cgaccgcctg cgcctgggct ccctgaccga ggacggcctg     240
tcctacaagg agaagttcat cgtgcgctgc tacgaggtgg gcatcaacaa gaccgccacc     300
gtggagacca tcgccaacct gctgcaggag gtgggctgca ccacgcccca gtccgtgggc     360
tactccaccg gcggcttctc caccaccccc accatgcgca agctgcgcct gatctgggtg     420
accgcccgca tgcacatcga gatctacaag taccccgcct ggtccgacgt ggtggagatc     480
gagtcctggg ccagggcga gggcaagatc ggcaagcgcc gcgactggat cctgcgcgac     540
```

```
tacgccaccg gccaggtgat cggccgcgcc acctccaagt gggtgatgat gaaccaggac      600
acccgccgcc tgcagaaggt ggacgtggac gtgcgcgacg agtacctggt gcactgcccc      660
cgcgagctgc gcctggcctt ccccgaggag aacaactcct ccctgaagaa gatctccaag      720
ctggaggacc cctcccagta ctccaagctg ggcctggtgc ccgccgcgc cgacctggac       780 atgaaccagc acgtgaacaa cgtgacctac atcggctggg tgctggagtc catgccccag      840
gagatcatcg acacccacga gctgcagacc atcaccctgg actaccgccg cgagtgccag      900
cacgacgacg tggtggactc cctgacctcc cccgagccct ccgaggacgc cgaggccgtg      960
ttcaaccaca acggcaccaa cggctccgcc aacgtgtccg ccaacgacca cggctgccgc     1020
aacttcctgc acctgctgcg cctgtccggc aacggcctgg agatcaaccg cggccgcacc     1080
gagtggcgca agaagcccac ccgcatggac tacaaggacc acgacggcga ctacaaggac     1140
cacgacatcg actacaagga cgacgacgac aagtga                              1176
```

<210> SEQ ID NO 44
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
atggccaccg catccacttt ctcggcgttc aatgcccgct gcggcgacct gcgtcgctcg       60
gcgggctccg ggccccggcg cccagcgagg cccctcccg tgcgcgggcg cgccatcccc       120
ccccgcatca tcgtggtgtc ctcctcctcc tccaaggtga acccctgaa gaccgaggcc       180 gtggtgtcct ccggcctggc cgaccgcctg cgcctgggct ccctgaccga ggacggcctg      240
tcctacaagg agaagttcat cgtgcgctgc tacgaggtgg gcatcaacaa gaccgccacc      300
gtggagacca tcgccaacct gctgcaggag gtgggctgca accacgccca gtccgtgggc      360
tactccaccg gcggcttctc caccacccc accatgcgca agctgcgcct gatctgggtg       420
accgcccgca tgcacatcga gatctacaag taccccgcct ggtccgacgt ggtggagatc      480
gagtcctggg ccagggcga gggcaagatc ggcgtgcgcc gcgactggat cctgcgcgac       540
tacgccaccg gccaggtgat cggccgcgcc acctccaagt gggtgatgat gaaccaggac      600
acccgccgcc tgcagaaggt ggacgtggac gtgcgcgacg agtacctggt gcactgcccc      660
cgcgagctgc gcctggcctt ccccgaggag aacaactcct ccctgaagaa gatctccaag      720
ctggaggacc cctcccagta ctccaagctg ggcctggtgc ccgccgcgc cgacctggac       780 atgaaccagc acgtgaacaa cgtgacctac atcggctggg tgctggagtc catgccccag      840
gagatcatcg acacccacga gctgcagacc atcaccctgg actaccgccg cgagtgccag      900
cacgacgacg tggtggactc cctgacctcc cccgagccct ccgaggacgc cgaggccgtg      960
ttcaaccaca acggcaccaa cggctccgcc aacgtgtccg ccaacgacca cggctgccgc     1020
aacttcctgc acctgctgcg cctgtccggc aacggcctgg agatcaaccg cggccgcacc     1080
gagtggcgca agaagcccac ccgcatggac tacaaggacc acgacggcga ctacaaggac     1140
cacgacatcg actacaagga cgacgacgac aagtga                              1176
```

<210> SEQ ID NO 45
<211> LENGTH: 330
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 45

Ile Pro Pro Arg Ile Ile Val Ser Ser Ser Ser Lys Val Asn
1               5                   10                  15

Pro Leu Lys Thr Glu Ala Val Val Ser Ser Gly Leu Ala Asp Arg Leu
            20                  25                  30

Arg Leu Gly Ser Leu Thr Glu Asp Gly Leu Ser Tyr Lys Glu Lys Phe
        35                  40                  45

Ile Val Arg Cys Tyr Glu Val Gly Ile Asn Lys Thr Ala Thr Val Glu
    50                  55                  60

Thr Ile Ala Asn Leu Leu Gln Glu Val Gly Cys Asn His Ala Gln Ser
65                  70                  75                  80

Val Gly Tyr Ser Thr Gly Gly Phe Ser Thr Thr Pro Thr Met Arg Lys
                85                  90                  95

Leu Arg Leu Ile Trp Val Thr Ala Arg Met His Ile Glu Ile Tyr Lys
            100                 105                 110

Tyr Pro Ala Trp Ser Asp Val Val Glu Ile Glu Ser Trp Gly Gln Gly
        115                 120                 125

Glu Gly Lys Ile Gly Thr Arg Arg Asp Trp Ile Leu Arg Asp Tyr Ala
    130                 135                 140

Thr Gly Gln Val Ile Gly Arg Ala Thr Ser Lys Trp Val Met Met Asn
145                 150                 155                 160

Gln Asp Thr Arg Arg Leu Gln Lys Val Asp Val Asp Val Arg Asp Glu
                165                 170                 175

Tyr Leu Val His Cys Pro Arg Glu Leu Arg Leu Ala Phe Pro Glu Glu
            180                 185                 190

Asn Asn Ser Ser Leu Lys Lys Ile Ser Lys Leu Glu Asp Pro Ser Gln
        195                 200                 205

Tyr Ser Lys Leu Gly Leu Val Pro Arg Arg Ala Asp Leu Asp Met Asn
    210                 215                 220

Gln His Val Asn Asn Val Thr Tyr Ile Gly Trp Val Leu Glu Ser Met
225                 230                 235                 240

Pro Gln Glu Ile Ile Asp Thr His Glu Leu Gln Thr Ile Thr Leu Asp
                245                 250                 255

Tyr Arg Arg Glu Cys Gln His Asp Asp Val Val Asp Ser Leu Thr Ser
            260                 265                 270

Pro Glu Pro Ser Glu Asp Ala Glu Ala Val Phe Asn His Asn Gly Thr
        275                 280                 285

Asn Gly Ser Ala Asn Val Ser Ala Asn Asp His Gly Cys Arg Asn Phe
    290                 295                 300

Leu His Leu Leu Arg Leu Ser Gly Asn Gly Leu Glu Ile Asn Arg Gly
305                 310                 315                 320

Arg Thr Glu Trp Arg Lys Lys Pro Thr Arg
                325                 330

<210> SEQ ID NO 46
<211> LENGTH: 8510
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

-continued

| | |
|---|---|
| gctcttccca actcagataa taccaatacc cctccttctc ctcctcatcc attcagtacc | 60 |
| cccccccttc tcttcccaaa gcagcaagcg cgtggcttac agaagaacaa tcggcttccg | 120 |
| ccaaagtcgc cgagcactgc ccgacggcgg cgcgcccagc agcccgcttg gccacacagg | 180 |
| caacgaatac attcaatagg gggcctcgca gaatggaagg agcggtaaag ggtacaggag | 240 |
| cactgcgcac aaggggcctg tgcaggagtg actgactggg cgggcagacg gcgcaccgcg | 300 |
| ggcgcaggca agcagggaag attgaagcgg cagggaggag gatgctgatt gagggggggca | 360 |
| tcgcagtctc tcttggaccc gggataagga agcaaatatt cggccggttg ggttgtgtgt | 420 |
| gtgcacgttt tcttcttcag agtcgtgggt gtgcttccag ggaggatata agcagcagga | 480 |
| tcgaatcccg cgaccagcgt ttccccatcc agccaaccac cctgtcggta cccttcttg | 540 |
| cgctatgaca cttccagcaa aaggtagggc gggctgcgag acggcttccc ggcgctgcat | 600 |
| gcaacaccga tgatgcttcg accccccgaa gctccttcgg ggctgcatgg gcgctccgat | 660 |
| gccgctccag ggcgagcgct gtttaaatag ccaggccccc gattgcaaag acattatagc | 720 |
| gagctaccaa agccatattc aaacacctag atcactacca cttctacaca ggccactcga | 780 |
| gcttgtgatc gcactccgct aagggggcgc ctcttcctct tcgtttcagt cacaacccgc | 840 |
| aaactctaga atatcaatgc tgctgcaggc cttcctgttc ctgctggccg gcttcgccgc | 900 |
| caagatcagc gcctccatga cgaacgagac gtccgaccgc cccctggtgc acttcacccc | 960 |
| caacaagggc tggatgaacg accccaacgg cctgtggtac gacgagaagg acgccaagtg | 1020 |
| gcacctgtac ttccagtaca acccgaacga caccgtctgg gggacgccct tgttctgggg | 1080 |
| ccacgccacg tccgacgacc tgaccaactg ggaggaccag cccatcgcca tcgcccgaa | 1140 |
| gcgcaacgac tccggcgcct tctccggctc catggtggtg gactacaaca cacctccgg | 1200 |
| cttcttcaac gacaccatcg acccgcgcca gcgctgcgtg gccatctgga cctacaacac | 1260 |
| cccggagtcc gaggagcagt acatctccta cagcctggac ggcggctaca ccttcaccga | 1320 |
| gtaccagaag aaccccgtgc tggccgccaa ctccacccag ttccgcgacc cgaaggtctt | 1380 |
| ctggtacgag ccctcccaga gtggatcat gaccgcggcc aagtcccagg actacaagat | 1440 |
| cgagatctac tcctccgacg acctgaagtc ctggaagctg gagtccgcgt tcgccaacga | 1500 |
| gggcttcctc ggctaccagt acgagtgccc cggcctgatc gaggtcccca ccgagcagga | 1560 |
| ccccagcaag tcctactggg tgatgttcat ctccatcaac cccggcgccc cggcggcgg | 1620 |
| ctccttcaac cagtacttcg tcggcagctt caacggcacc cacttcgagg ccttcgacaa | 1680 |
| ccagtcccgc gtggtggact tcggcaagga ctactacgcc ctgcagacct tcttcaacac | 1740 |
| cgacccgacc tacgggagcg ccctgggcat cgcgtgggcc tccaactggg agtactccgc | 1800 |
| cttcgtgccc accaaccccct ggcgctcctc catgtccctc gtgcgcaagt tctccctcaa | 1860 |
| caccgagtac caggccaacc cggagacgga gctgatcaac ctgaaggccg agccgatcct | 1920 |
| gaacatcagc aacgccggcc cctggagccg gttcgccacc aacaccacgt tgacgaaggc | 1980 |
| caacagctac aacgtcgacc tgtccaacag caccggcacc ctggagttcg agctggtgta | 2040 |
| cgccgtcaac accacccaga cgatctccaa gtccgtgttc gcggacctct ccctctggtt | 2100 |
| caagggcctg gaggaccccg aggagtacct ccgcatgggc ttcgaggtgt ccgcgtcctc | 2160 |
| cttcttcctg gaccgcggga acagcaaggt gaagttcgtg aaggagaacc cctacttcac | 2220 |
| caaccgcatg agcgtgaaca accagcccct caagagcgag aacgacctgt cctactacaa | 2280 |
| ggtgtacggc ttgctggacc agaacatcct ggagctgtac ttcaacgacg gcgacgtcgt | 2340 |
| gtccaccaac acctacttca tgaccaccgg gaacgccctg ggctccgtga acatgacgac | 2400 |

-continued

```
gggggtggac aacctgttct acatcgacaa gttccaggtg cgcgaggtca agtgacaatt    2460
gacgcccgcg cggcgcacct gacctgttct ctcgagggcg cctgttctgc cttgcgaaac    2520
aagcccctgg agcatgcgtg catgatcgtc tctggcgccc cgccgcgcgg tttgtcgccc    2580
tcgcgggcgc cgcggccgcg ggggcgcatt gaaattgttg caaacccac ctgacagatt    2640 gagggcccag gcaggaaggc gttgagatgg aggtacagga gtcaagtaac tgaaagtttt    2700
tatgataact aacaacaaag ggtcgtttct ggccagcgaa tgacaagaac aagattccac    2760
atttccgtgt agaggcttgc catcgaatgt gagcgggcgg ccgcggaccc gacaaaacc    2820 cttacgacgt ggtaagaaaa acgtggcggg cactgtccct gtagcctgaa gaccagcagg    2880
agacgatcgg aagcatcaca gcacaggatc ccgcgtctcg aacagagcgc gcagaggaac    2940
gctgaaggtc tcgcctctgt cgcacctcag gcgggcatac accacaataa ccacctgacg    3000
aatgcgcttg gttcttcgtc cattagcgaa gcgtccggtt cacacacgtg ccacgttggc    3060
gaggtggcag gtgacaatga tcggtggagc tgatggtcga aacgttcaca gcctaggtac    3120
gccgctcagc ctacacgtct tctccgatac ctttccctca ttgcatttta tgccagactg    3180
ggtcccagcc tgggtgggtg ctcccgctcg attgctcgtg tcggaggcgg ggcacccccg    3240
ctctctctat ttatcactgc ctctccccga ccaaccctga cgactgtaac cctgccagaa    3300
acaattcagc ctcatcaaac cgagttgtgc acaagggcga ctaatttttt agtcgggaaa    3360
caacccgctt ccagaagcat ccggacgggg gtagcgaggc tgtgtcgagc gccgtgggga    3420
tctggccggt gaggtgcccg aaatccgtgt acagctcagc ggctgggatc atcgaccccc    3480
gggatcatcg accccgtggg ccgggccccc ggaccctata actaaaagcc gacgccagtg    3540
caaaaccaca aacatttact ccttaatcct ccctcctcct tcatacacac ccacaagtaa    3600
tcaactcacc catatggcca tcgccgccgc cgccgtgatc gtgcccctgg gcctgctgtt    3660
cttcatctcc ggcctggtgg tgaacctgat ccaggccctg tgcttcgtgc tgatccgccc    3720
cctgtccaag aacacctacc gcaagatcaa ccgcgtggtg gccgagctgc tgtggctgga    3780
gctgatctgg ctggtggact ggtgggccgg cgtgaagatc aaggtgttca tggaccccga    3840
gtccttcaac ctgatgggca aggagcacgc cctggtggtg gccaaccacc gctccgacat    3900
cgactggctg gtgggctggc tgctggccca gcgctccggc tgcctgggct ccgccctggc    3960
cgtgatgaag aagtcctcca agttcctgcc cgtgatcggc tggtccatgt ggttctccga    4020
gtacctgttc ctggagcgct cctgggccaa ggacgagaac accctgaagg ccggcctgca    4080
gcgcctgaag gacttccccc gccccttctg gctggccttc ttcgtggagg caccccgctt    4140
cacccaggcc aagttcctgg ccgcccagga gtacgccgcc tcccagggcc tgcccatccc    4200
ccgcaacgtg ctgatccccc gcaccaaggg cttcgtgtcc gccgtgtccc acatgcgctc    4260
cttcgtgccc gccatctacg acatgaccgt ggccatcccc aagtcctccc cctccccac    4320 catgctgcgc ctgttcaagg gccagccctc cgtggtgcac gtgcacatca gcgctgcct    4380 gatgaaggag ctgcccgaga ccgacgaggc cgtggcccag tggtgcaagg acatgttcgt    4440
ggagaaggac aagctgctgg acaagcacat cgccgaggac accttctccg accagcccat    4500
gcaggacctg ggccgcccca tcaagtccct gctggtggtg gcctcctggg cctgcctgat    4560
ggcctacggc gccctgaagt tcctgcagtg ctcctccctg ctgtcctcct ggaagggcat    4620
cgccttcttc ctggtgggcc tggccatcgt gaccatcctg atgcacatcc tgatcctgtt    4680
ctcccagtcc gagcgctcca ccccgccaa ggtggccccc ggcaagccca agaacgacgg    4740
```

```
cgagacctcc gaggcccgcc gcgacaagca gcagtgaatg catatgtgga gatgtagggt    4800
ggtcgactcg ttggaggtgg gtgttttttt ttatcgagtg cgcggcgcgg caaacgggtc    4860
cctttttatc gaggtgttcc caacgccgca ccgccctctt aaaacaaccc ccaccaccac    4920
ttgtcgacct tctcgtttgt tatccgccac ggcgccccgg aggggcgtcg tctggccgcg    4980
cgggcagctg tatcgccgcg ctcgctccaa tggtgtgtaa tcttggaaag ataataatcg    5040
atggatgagg aggagagcgt gggagatcag agcaaggaat atacagttgg cacgaagcag    5100
cagcgtacta agctgtagcg tgttaagaaa gaaaaactcg ctgttaggct gtattaatca    5160
aggagcgtat caataattac cgaccctata cctttatctc caacccaatc gcggcttaag    5220
gatctaagta agattcgaag cgctcgaccg tgccggacgg actgcagccc catgtcgtag    5280
tgaccgccaa tgtaagtggg ctggcgtttc cctgtacgtg agtcaacgtc actgcacgcg    5340
caccacccct ctcgaccggca ggaccaggca tcgcgagata cagcgcgagc cagacacgga    5400
gtgccgagct atgcgcacgc tccaactaga tatcatgtgg atgatgagca tgaattcctg    5460
gctcgggcct cgtgctggca ctccctccca tgccgacaac ctttctgctg tcaccacgac    5520
ccacgatgca acgcgacacg acccggtggg actgatcggt tcactgcacc tgcatgcaat    5580
tgtcacaagc gcatactcca atcgtatccg tttgatttct gtgaaaactc gctcgaccgc    5640
ccgcgtcccg caggcagcga tgacgtgtgc gtgacctggg tgtttcgtcg aaaggccagc    5700
aaccccaaat cgcaggcgat ccggagattg ggatctgatc cgagcttgga ccagatcccc    5760
cacgatgcgg cacgggaact gcatcgactc ggcgcggaac ccagctttcg taaatgccag    5820
attggtgtcc gataccttga tttgccatca gcgaaacaag acttcagcag cgagcgtatt    5880
tggcgggcgt gctaccaggg ttgcatacat tgcccatttc tgtctggacc gctttaccgg    5940
cgcagagggt gagttgatgg ggttggcagg catcgaaacg cgcgtgcatg gtgtgtgtgt    6000
ctgtttttcgg ctgcacaatt tcaatagtcg gatgggcgac ggtagaattg ggtgttgcgc    6060
tcgcgtgcat gcctcgcccc gtcgggtgtc atgaccggga ctggaatccc ccctcgcgac    6120
cctcctgcta acgctcccga ctctcccgcc cgcgcgcagg atagactcta gttcaaccaa    6180
tcgacaacta gtatggccac cgcatccact ttctcggcgt tcaatgcccg ctgcggcgac    6240
ctgcgtcgct cggcgggctc cgggcccggc gcccagcga ggcccctccc cgtgcgcggg    6300
cgcgccatcc cccccgcat catcgtggtg tcctcctcct cctccaaggt gaacccctg    6360
aagaccgagg ccgtggtgtc ctccggcctg gccgaccgcc tgcgcctggg ctccctgacc    6420
gaggacggcc tgtcctacaa ggagaagttc atcgtgcgct gctacgaggt gggcatcaac    6480
aagaccgcca ccgtggagac catcgccaac ctgctgcagg aggtggcgtg caaccacgcc    6540
cagtccgtgg gctactccac cgccggcttc tccaccaccc ccaccatgcg caagctgcgc    6600
ctgatctggg tgaccgcccg catgcacatc gagatctaca agtaccccgc ctggtccgac    6660
gtggtggaga tcgagtcctg ggcccagggc gagggcaaga tcggcacccg ccgcgactgg    6720
atcctgcgcg actacgccac cggccaggtg atcggccgcg ccacctccaa gtgggtgatg    6780
atgaaccagg acacccgccg cctgcagaag gtggacgtgg acgtgcgcga cgagtacctg    6840
gtgcactgcc ccgcgagct cgcgctggcc ttccccgagg agaacaactc ctccctgaag    6900
aagatctcca agctggagga cccctcccag tactccaagc tgggcctggt gccccgccgc    6960
gccgacctgg acatgaacca gcacgtgaac aacgtgacct acatcggctg ggtgctggag    7020
tccatgcccc aggagatcat cgacacccac gagctgcaga ccatcaccct ggactaccgc    7080
cgcgagtgcc agcacgacga cgtggtggac tccctgacct ccccgagcc ctccgaggac    7140
```

```
gccgaggccg tgttcaacca caacggcacc aacggctccg ccaacgtgtc cgccaacgac      7200
cacggctgcc gcaacttcct gcacctgctg cgcctgtccg gcaacggcct ggagatcaac      7260
cgcggccgca ccgagtggcg caagaagccc acccgcatgg actacaagga ccacgacggc      7320
gactacaagg accacgacat cgactacaag gacgacgacg acaagtgaat cgatggagcg      7380
acgagtgtgc gtgcggggct ggcgggagtg ggacgccctc ctcgctcctc tctgttctga      7440
acggaacaat cggccacccc gcgctacgcg ccacgcatcg agcaacgaag aaacccccc      7500 gatgataggt tgcggtggct gccgggatat agatccggcc gcacatcaaa gggcccctcc      7560
gccagagaag aagctccttt cccagcgac tccttctgct gccaaaacac ttctctgtcc      7620
acagcaacac caaaggatga acagatcaac ttgcgtctcc gcgtagcttc ctcggctagc      7680
gtgcttgcaa caggtccctg cactattatc ttcctgcttt cctctgaatt atgcggcagg      7740
cgagcgctcg ctctggcgag cgctccttcg cgccgccctc gctgatcgag tgtacagtca      7800
atgaatggtg agctcttgtt ttccagaagg agttgctcct tgagcctttc attctcagcc      7860
tcgataacct ccaaagccgc tctaattgtg gagggggttc gaaccgaatg ctgcgtgaac      7920
gggaaggagg aggagaaaga gtgagcaggg agggattcag aaatgagaaa tgagaggtga      7980
aggaacgcat ccctatgccc ttgcaatgga cagtgtttct ggccaccgcc accaagactt      8040
cgtgtcctct gatcatcatg cgattgatta cgttgaatgc gacggccggt cagccccgga      8100
cctccacgca ccggtgctcc tccaggaaga tgcgcttgtc ctccgccatc ttgcagggct      8160
caagctgctc ccaaaactct tgggcgggtt ccggacggac ggctaccgcg ggtgcggccc      8220
tgaccgccac tgttcggaag cagcggcgct gcatgggcag cggccgctgc ggtgcgccac      8280
ggaccgcatg atccaccgga aaagcgcacg cgctggagcg cgcagaggac acagagaag      8340 cggaagagac gccagtactg gcaagcaggc tggtcggtgc catggcgcgc tactaccctc      8400
gctatgactc gggtcctcgg ccggctggcg gtgctgacaa ttcgtttagt ggagcagcga      8460
ctccattcag ctaccagtcg aactcagtgg cacagtgact cccgctcttc              8510
```

<210> SEQ ID NO 47
<211> LENGTH: 1188
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 47

```
actagtatgg ccaccgcatc cactttctcg gcgttcaatg cccgctgcgg cgacctgcgt        60
cgctcggcgg gctccgggcc ccggcgccca gcgaggcccc tccccgtgcg cgggcgcgcc       120 atccccccccc gcatcatcgt ggtgtcctcc tcctcctcca aggtgaaccc cctgaagacc       180
gaggccgtgg tgtcctccgg cctggccgac cgcctgcgcc tgggctccct gaccgaggac       240
ggcctgtcct acaaggagaa gttcatcgtg cgctgctacg aggtgggcat caacaagacc       300
gccaccgtgg agaccatcgc caacctgctg caggaggtgg gctgcaacca cgcccagtcc       360
gtgggctact ccaccgccgg cttctccacc accccccacca tgcgcaagct gcgcctgatc       420
tgggtgaccg cccgcatgca catcgagatc tacaagtacc ccgcctggtc cgacgtggtg       480
gagatcgagt cctggggcca gggcgagggc aagatcggca cccgccgcga ctggatcctg       540
cgcgactacg ccaccggcca ggtgatcggc cgcgccacct ccaagtgggt gatgatgaac       600
caggacaccc gccgcctgca gaaggtggac gtggacgtgc gcgacgagta cctggtgcac       660
```

```
tgcccccgcg agctgcgcct ggccttcccc gaggagaaca actcctccct gaagaagatc    720
tccaagctgg aggacccctc ccagtactcc aagctgggcc tggtgccccg ccgcgccgac    780
ctggacatga accagcacgt gaacaacgtg acctacatcg gctgggtgct ggagtccatg    840
ccccaggaga tcatcgacac ccacgagctg cagaccatca ccctggacta ccgccgcgag    900
tgccagcacg acgacgtggt ggactccctg acctcccccg agccctccga ggacgccgag    960
gccgtgttca accacaacgg caccaacggc tccgccaacg tgtccgccaa cgaccacggc   1020
tgccgcaact tcctgcacct gctgcgcctg tccggcaacg gcctggagat caaccgcggc   1080
cgcaccgagt ggcgcaagaa gcccaccgcc atggactaca aggaccacga cggcgactac   1140
aaggaccacg acatcgacta caaggacgac gacgacaagt gaatcgat               1188
```

<210> SEQ ID NO 48
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
actagtatgg ccaccgcatc cactttctcg gcgttcaatg cccgctgcgg cgacctgcgt     60
cgctcggcgg gctccgggcc ccggcgccca gcgaggcccc tccccgtgcg cgggcgcgcc    120 atccccccc gcatcatcgt ggtgtcctcc tcctcctcca aggtgaaccc cctgaagacc    180
gaggccgtgg tgtcctccgg cctggccgac cgcctgcgcc tgggctccct gaccgaggac    240
ggcctgtcct acaaggagaa gttcatcgtg cgctgctacg aggtgggcat caacaagacc    300
gccaccgtgg agaccatcgc caacctgctg caggaggtgg cgtgcaacca cgcccagtcc    360
gtgggctact ccaccggcgg cttcgccacc acccccacca tgcgcaagct gcgcctgatc    420
tgggtgaccg cccgcatgca catcgagatc tacaagtacc ccgcctggtc cgacgtggtg    480
gagatcgagt cctggggcca gggcgagggc aagatcggca cccgccgcga ctggatcctg    540
cgcgactacg ccaccggcca ggtgatcggc cgcgccacct ccaagtgggt gatgatgaac    600
caggacaccc gccgcctgca gaaggtggac gtggacgtgc gcgacgagta cctggtgcac    660
tgcccccgcg agctgcgcct ggccttcccc gaggagaaca actcctccct gaagaagatc    720
tccaagctgg aggaccctc ccagtactcc aagctgggcc tggtgccccg ccgcgccgac    780
ctggacatga accagcacgt gaacaacgtg acctacatcg gctgggtgct ggagtccatg    840
ccccaggaga tcatcgacac ccacgagctg cagaccatca ccctggacta ccgccgcgag    900
tgccagcacg acgacgtggt ggactccctg acctcccccg agccctccga ggacgccgag    960
gccgtgttca accacaacgg caccaacggc tccgccaacg tgtccgccaa cgaccacggc   1020
tgccgcaact tcctgcacct gctgcgcctg tccggcaacg gcctggagat caaccgcggc   1080
cgcaccgagt ggcgcaagaa gcccaccgcc atggactaca aggaccacga cggcgactac   1140
aaggaccacg acatcgacta caaggacgac gacgacaagt gaatcgat               1188
```

<210> SEQ ID NO 49
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 49
actagtatgg ccaccgcatc cactttctcg gcgttcaatg cccgctgcgg cgacctgcgt      60
cgctcggcgg gctccgggcc ccggcgccca gcgaggcccc tccccgtgcg cgggcgcgcc     120
atcccccccc gcatcatcgt ggtgtcctcc tcctcctcca aggtgaaccc cctgaagacc     180
gaggccgtgg tgtcctccgg cctggccgac cgcctgcgcc tgggctccct gaccgaggac     240
ggcctgtcct acaaggagaa gttcatcgtg cgctgctacg aggtgggcat caacaagacc     300
gccaccgtgg agaccatcgc caacctgctg caggaggtgg cgtgcaacca cgcccagtcc     360
gtgggctact ccaccggcgg cttctccacc accccacca tgcgcaagct gcgcctgatc      420
tgggtgaccg cccgcatgca catcgagatc tacaagtacc ccgcctggtc cgacgtggtg     480
gagatcgagt cctggggcca gggcgagggc aagatcggca cccgccgcga ctggatcctg     540
cgcgactacg ccaccggcca ggtgatcggc cgcgccacct ccaagtgggt gatgatgaac     600
caggacaccc gccgcctgca gaaggtggac gcggacgtgc gcgacgagta cctggtgcac     660 tgccccgcg agctgcgcct ggccttcccc gaggagaaca actcctccct gaagaagatc      720
tccaagctgg aggacccctc ccagtactcc aagctgggcc tggtgccccg ccgcgccgac     780
ctggacatga accagcacgt gaacaacgtg acctacatcg gctgggtgct ggagtccatg     840
ccccaggaga tcatcgacac ccacgagctg cagaccatca ccctggacta ccgccgcgag     900
tgccagcacg acgacgtggt ggactccctg acctcccccg agccctccga ggacgccgag     960
gccgtgttca accacaacgg caccaacggc tccgccaacg tgtccgccaa cgaccacggc    1020
tgccgcaact tcctgcacct gctgcgcctg tccggcaacg gcctggagat caaccgcggc    1080
cgcaccgagt ggcgcaagaa gcccacccgc atggactaca aggaccacga cggcgactac    1140
aaggaccacg acatcgacta caaggacgac gacgacaagt gaatcgat               1188

<210> SEQ ID NO 50
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
actagtatgg ccaccgcatc cactttctcg gcgttcaatg cccgctgcgg cgacctgcgt      60
cgctcggcgg gctccgggcc ccggcgccca gcgaggcccc tccccgtgcg cgggcgcgcc     120
atcccccccc gcatcatcgt ggtgtcctcc tcctcctcca aggtgaaccc cctgaagacc     180
gaggccgtgg tgtcctccgg cctggccgac cgcctgcgcc tgggctccct gaccgaggac     240
ggcctgtcct acaaggagaa gttcatcgtg cgctgctacg aggtgggcat caacaagacc     300
gccaccgtgg agaccatcgc caacctgctg caggaggtgg gctgcaacca cgcccagtcc     360
gtgggctact ccaccgccgg cttcgccacc accccacca tgcgcaagct gcgcctgatc      420
tgggtgaccg cccgcatgca catcgagatc tacaagtacc ccgcctggtc cgacgtggtg     480
gagatcgagt cctggggcca gggcgagggc aagatcggca cccgccgcga ctggatcctg     540
cgcgactacg ccaccggcca ggtgatcggc cgcgccacct ccaagtgggt gatgatgaac     600
caggacaccc gccgcctgca gaaggtggac gtggacgtgc gcgacgagta cctggtgcac     660 tgccccgcg agctgcgcct ggccttcccc gaggagaaca actcctccct gaagaagatc      720
tccaagctgg aggacccctc ccagtactcc aagctgggcc tggtgccccg ccgcgccgac     780
```

```
ctggacatga accagcacgt gaacaacgtg acctacatcg gctgggtgct ggagtccatg      840
ccccaggaga tcatcgacac ccacgagctg cagaccatca ccctggacta ccgccgcgag      900
tgccagcacg acgacgtggt ggactccctg acctcccccg agccctccga ggacgccgag      960
gccgtgttca accacaacgg caccaacggc tccgccaacg tgtccgccaa cgaccacggc     1020
tgccgcaact tcctgcacct gctgcgcctg tccggcaacg gcctggagat caaccgcggc     1080
cgcaccgagt ggcgcaagaa gcccacccgc atggactaca aggaccacga cggcgactac     1140
aaggaccacg acatcgacta caaggacgac gacgacaagt gaatcgat                  1188
```

<210> SEQ ID NO 51
<211> LENGTH: 1188
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 51

```
actagtatgg ccaccgcatc cactttctcg gcgttcaatg cccgctgcgg cgacctgcgt       60
cgctcggcgg gctccgggcc ccggcgccca gcgaggcccc tccccgtgcg cgggcgcgcc      120 atccccccccc gcatcatcgt ggtgtcctcc tcctcctcca aggtgaaccc cctgaagacc     180
gaggccgtgt tgtcctccgg cctggccgac cgcctgcgcc tgggctccct gaccgaggac     240
ggcctgtcct acaaggagaa gttcatcgtg cgctgctacg aggtgggcat caacaagacc     300
gccaccgtgg agaccatcgc caacctgctg caggaggtgg gctgcaacca cgcccagtcc     360
gtgggctact ccaccgccgg cttctccacc accccccacca tgcgcaagct cgcgcctgatc    420 tgggtgaccg cccgcatgca catcgagatc tacaagtacc ccgcctggtc cgacgtggtg    480
gagatcgagt cctggggcca gggcgagggc aagatcggca cccgccgcga ctggatcctg    540
cgcgactacg ccaccggcca ggtgatcggc cgcgccacct ccaagtgggt gatgatgaac    600
caggacaccc gccgcctgca gaaggtggac gcggacgtgc gcgacgagta cctggtgcac    660 tgccccccgcg agctgcgcct ggccttcccc gaggagaaca actcctccct gaagaagatc    720
tccaagctgg aggacccctc ccagtactcc aagctgggcc tggtgccccg ccgcgccgac    780
ctggacatga accagcacgt gaacaacgtg acctacatcg gctgggtgct ggagtccatg    840
ccccaggaga tcatcgacac ccacgagctg cagaccatca ccctggacta ccgccgcgag    900
tgccagcacg acgacgtggt ggactccctg acctcccccg agccctccga ggacgccgag    960
gccgtgttca accacaacgg caccaacggc tccgccaacg tgtccgccaa cgaccacggc   1020
tgccgcaact tcctgcacct gctgcgcctg tccggcaacg gcctggagat caaccgcggc   1080
cgcaccgagt ggcgcaagaa gcccacccgc atggactaca aggaccacga cggcgactac   1140
aaggaccacg acatcgacta caaggacgac gacgacaagt gaatcgat                1188
```

<210> SEQ ID NO 52
<211> LENGTH: 1188
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 52

```
actagtatgg ccaccgcatc cactttctcg gcgttcaatg cccgctgcgg cgacctgcgt       60
cgctcggcgg gctccgggcc ccggcgccca gcgaggcccc tccccgtgcg cgggcgcgcc      120
```

```
atccccccc  gcatcatcgt  ggtgtcctcc  tcctcctcca  aggtgaaccc  cctgaagacc    180
gaggccgtgg  tgtcctccgg  cctggccgac  cgcctgcgcc  tgggctccct  gaccgaggac    240
ggcctgtcct  acaaggagaa  gttcatcgtg  cgctgctacg  aggtgggcat  caacaagacc    300
gccaccgtgg  agaccatcgc  caacctgctg  caggaggtgg  cgtgcaacca  cgcccagtcc    360
gtgggctact  ccaccgccgg  cttcgccacc  accccacca   tgcgcaagct  gcgcctgatc    420
tgggtgaccg  cccgcatgca  catcgagatc  tacaagtacc  ccgcctggtc  cgacgtggtg    480
gagatcgagt  cctggggcca  gggcgagggc  aagatcggca  cccgccgcga  ctggatcctg    540
cgcgactacg  ccaccggcca  ggtgatcggc  cgcgccacct  ccaagtgggt  gatgatgaac    600
caggacaccc  gccgcctgca  gaaggtggac  gtggacgtgc  gcgacgagta  cctggtgcac    660
tgccccgcg   agctgcgcct  ggccttcccc  gaggagaaca  actcctccct  gaagaagatc    720
tccaagctgg  aggaccctc   ccagtactcc  aagctgggcc  tggtgccccg  ccgcgccgac    780
ctggacatga  ccagcacgt   gaacaacgtg  acctacatcg  gctgggtgct  ggagtccatg    840
ccccaggaga  tcatcgacac  ccacgagctg  cagaccatca  ccctggacta  ccgccgcgag    900
tgccagcacg  acgacgtggt  ggactccctg  acctcccccg  agccctccga  ggacgccgag    960
gccgtgttca  accacaacgg  caccaacggc  tccgccaacg  tgtccgccaa  cgaccacggc    1020
tgccgcaact  tcctgcacct  gctgcgcctg  tccggcaacg  gctggagat   caaccgcggc    1080
cgcaccgagt  ggcgcaagaa  gcccaccgc   atggactaca  aggaccacga  cggcgactac    1140
aaggaccacg  acatcgacta  caaggacgac  gacgacaagt  gaatcgat                  1188
```

<210> SEQ ID NO 53
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
actagtatgg  ccaccgcatc  cactttctcg  gcgttcaatg  cccgctgcgg  cgacctgcgt     60
cgctcggcgg  gctccgggcc  ccggcgccca  gcgaggcccc  tccccgtgcg  cgggcgcgcc    120
atccccccc  gcatcatcgt  ggtgtcctcc  tcctcctcca  aggtgaaccc  cctgaagacc    180
gaggccgtgg  tgtcctccgg  cctggccgac  cgcctgcgcc  tgggctccct  gaccgaggac    240
ggcctgtcct  acaaggagaa  gttcatcgtg  cgctgctacg  aggtgggcat  caacaagacc    300
gccaccgtgg  agaccatcgc  caacctgctg  caggaggtgg  cgtgcaacca  cgcccagtcc    360
gtgggctact  ccaccgccgg  cttctccacc  accccacca   tgcgcaagct  gcgcctgatc    420
tgggtgaccg  cccgcatgca  catcgagatc  tacaagtacc  ccgcctggtc  cgacgtggtg    480
gagatcgagt  cctggggcca  gggcgagggc  aagatcggca  cccgccgcga  ctggatcctg    540
cgcgactacg  ccaccggcca  ggtgatcggc  cgcgccacct  ccaagtgggt  gatgatgaac    600
caggacaccc  gccgcctgca  gaaggtggac  gcggacgtgc  gcgacgagta  cctggtgcac    660
tgccccgcg   agctgcgcct  ggccttcccc  gaggagaaca  actcctccct  gaagaagatc    720
tccaagctgg  aggaccctc   ccagtactcc  aagctgggcc  tggtgccccg  ccgcgccgac    780
ctggacatga  ccagcacgt   gaacaacgtg  acctacatcg  gctgggtgct  ggagtccatg    840
ccccaggaga  tcatcgacac  ccacgagctg  cagaccatca  ccctggacta  ccgccgcgag    900
tgccagcacg  acgacgtggt  ggactccctg  acctcccccg  agccctccga  ggacgccgag    960
```

```
gccgtgttca accacaacgg caccaacggc tccgccaacg tgtccgccaa cgaccacggc    1020
tgccgcaact tcctgcacct gctgcgcctg tccggcaacg gcctggagat caaccgcggc    1080
cgcaccgagt ggcgcaagaa gcccaccgc atggactaca aggaccacga cggcgactac     1140
aaggaccacg acatcgacta caaggacgac gacgacaagt gaatcgat                 1188
```

<210> SEQ ID NO 54
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
actagtatgg ccaccgcatc cactttctcg gcgttcaatg cccgctgcgg cgacctgcgt    60
cgctcggcgg gctccgggcc ccggcgccca gcgaggcccc tccccgtgcg cgggcgcgcc    120 atccccccc gcatcatcgt ggtgtcctcc tcctcctcca aggtgaaccc cctgaagacc     180
gaggccgtgg tgtcctccgg cctggccgac cgcctgcgcc tgggctccct gaccgaggac    240
ggcctgtcct acaaggagaa gttcatcgtg cgctgctacg aggtgggcat caacaagacc    300
gccaccgtgg agaccatcgc caacctgctg caggaggtgg cgtgcaacca cgcccagtcc    360
gtgggctact ccaccggcgg cttcgccacc acccccacca tgcgcaagct cgcctgatc    420 tgggtgaccg cccgcatgca catcgagatc tacaagtacc ccgcctggtc cgacgtggtg    480
gagatcgagt cctggggcca gggcgagggc aagatcggca cccgccgcga ctggatcctg    540
cgcgactacg ccaccggcca ggtgatcggc cgcgccacct ccaagtgggt gatgatgaac    600
caggacaccc gccgctgca gaaggtggac gcggacgtgc gcgacgagta cctggtgcac    660 tgccccccgcg agctgcgcct ggccttcccc gaggagaaca actcctccct gaagaagatc    720
tccaagctgg aggaccctc ccagtactcc aagctgggcc tggtgccccg ccgcgccgac     780
ctggacatga ccagcacgt gaacaacgtg acctacatcg gctgggtgct ggagtccatg     840
ccccaggaga tcatcgacac ccacgagctg cagaccatca ccctggacta ccgccgcgag    900
tgccagcacg acgacgtggt ggactccctg acctccccg agccctccga ggacgccgag    960
gccgtgttca ccacaacgg caccaacggc tccgccaacg tgtccgccaa cgaccacggc    1020
tgccgcaact tcctgcacct gctgcgcctg tccggcaacg gcctggagat caaccgcggc    1080
cgcaccgagt ggcgcaagaa gcccaccgc atggactaca aggaccacga cggcgactac     1140
aaggaccacg acatcgacta caaggacgac gacgacaagt gaatcgat                 1188
```

<210> SEQ ID NO 55
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
actagtatgg ccaccgcatc cactttctcg gcgttcaatg cccgctgcgg cgacctgcgt    60
cgctcggcgg gctccgggcc ccggcgccca gcgaggcccc tccccgtgcg cgggcgcgcc    120 atccccccc gcatcatcgt ggtgtcctcc tcctcctcca aggtgaaccc cctgaagacc     180
gaggccgtgg tgtcctccgg cctggccgac cgcctgcgcc tgggctccct gaccgaggac    240
```

| | |
|---|---|
| ggcctgtcct acaaggagaa gttcatcgtg cgctgctacg aggtgggcat caacaagacc | 300 |
| gccaccgtgg agaccatcgc caacctgctg caggaggtgg gctgcaacca cgcccagtcc | 360 |
| gtgggctact ccaccgccgg cttcgccacc accccacca tgcgcaagct gcgcctgatc | 420 |
| tgggtgaccg cccgcatgca catcgagatc tacaagtacc ccgcctggtc cgacgtggtg | 480 |
| gagatcgagt cctggggcca gggcgagggc aagatcggca cccgccgcga ctggatcctg | 540 |
| cgcgactacg ccaccggcca ggtgatcggc cgcgccacct ccaagtgggt gatgatgaac | 600 |
| caggacaccc gccgcctgca gaaggtggac gcggacgtgc gcgacgagta cctggtgcac | 660 |
| tgccccgcg agctgcgcct ggccttcccc gaggagaaca actcctccct gaagaagatc | 720 |
| tccaagctgg aggacccctc ccagtactcc aagctgggcc tggtgccccg ccgcgccgac | 780 |
| ctggacatga ccagcacgt gaacaacgtg acctacatcg ctgggtgct ggagtccatg | 840 |
| ccccaggaga tcatcgacac ccacgagctg cagaccatca ccctggacta ccgccgcgag | 900 |
| tgccagcacg acgacgtggt ggactccctg acctcccccg agccctccga ggacgccgag | 960 |
| gccgtgttca accacaacgg caccaacggc tccgccaacg tgtccgccaa cgaccacggc | 1020 |
| tgccgcaact tcctgcacct gctgcgcctg tccggcaacg gcctggagat caaccgcggc | 1080 |
| cgcaccgagt ggcgcaagaa gcccaccgc atggactaca aggaccacga cggcgactac | 1140 |
| aaggaccacg acatcgacta caaggacgac gacgacaagt gaatcgat | 1188 |

<210> SEQ ID NO 56
<211> LENGTH: 1188
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

| | |
|---|---|
| actagtatgg ccaccgcatc cactttctcg gcgttcaatg cccgctgcgg cgacctgcgt | 60 |
| cgctcggcgg gctccgggcc ccggcgccca gcgaggcccc tccccgtgcg cgggcgcgcc | 120 |
| atccccccc gcatcatcgt ggtgtcctcc tcctcctcca aggtgaaccc cctgaagacc | 180 |
| gaggccgtgg tgtcctccgg cctggccgac cgcctgcgcc tgggctccct gaccgaggac | 240 |
| ggcctgtcct acaaggagaa gttcatcgtg cgctgctacg aggtgggcat caacaagacc | 300 |
| gccaccgtgg agaccatcgc caacctgctg caggaggtgg cgtgcaacca cgcccagtcc | 360 |
| gtgggctact ccaccgccgg cttcgccacc accccacca tgcgcaagct gcgcctgatc | 420 |
| tgggtgaccg cccgcatgca catcgagatc tacaagtacc ccgcctggtc cgacgtggtg | 480 |
| gagatcgagt cctggggcca gggcgagggc aagatcggca cccgccgcga ctggatcctg | 540 |
| cgcgactacg ccaccggcca ggtgatcggc cgcgccacct ccaagtgggt gatgatgaac | 600 |
| caggacaccc gccgcctgca gaaggtggac gcggacgtgc gcgacgagta cctggtgcac | 660 |
| tgccccgcg agctgcgcct ggccttcccc gaggagaaca actcctccct gaagaagatc | 720 |
| tccaagctgg aggacccctc ccagtactcc aagctgggcc tggtgccccg ccgcgccgac | 780 |
| ctggacatga ccagcacgt gaacaacgtg acctacatcg ctgggtgct ggagtccatg | 840 |
| ccccaggaga tcatcgacac ccacgagctg cagaccatca ccctggacta ccgccgcgag | 900 |
| tgccagcacg acgacgtggt ggactccctg acctcccccg agccctccga ggacgccgag | 960 |
| gccgtgttca accacaacgg caccaacggc tccgccaacg tgtccgccaa cgaccacggc | 1020 |
| tgccgcaact tcctgcacct gctgcgcctg tccggcaacg gcctggagat caaccgcggc | 1080 |

```
cgcaccgagt ggcgcaagaa gcccacccgc atggactaca aggaccacga cggcgactac    1140
aaggaccacg acatcgacta caaggacgac gacgacaagt gaatcgat                 1188
```

<210> SEQ ID NO 57
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
gaattcgcct gctcaagcgg gcgctcaaca tgcagagcgt cagcgagacg ggctgtggcg     60
atcgcgagac ggacgaggcc gcctctgccc tgtttgaact gagcgtcagc gctggctaag    120
gggagggaga ctcatcccca ggctcgcgcc agggctctga tcccgtctcg ggcggtgatc    180
ggcgcgcatg actacgaccc aacgacgtac gagactgatg tcggtcccga cgaggagcgc    240
cgcgaggcac tcccgggcca ccgaccatgt ttacaccgac cgaaagcact cgctcgtatc    300
cattccgtgc gcccgcacat gcatcatctt ttggtaccga cttcggtctt gttttacccc    360
tacgacctgc cttccaaggt gtgagcaact cgcccggaca tgaccgaggg tgatcatccg    420
gatccccagg ccccagcagc ccctgccaga atggctcgcg ctttccagcc tgcaggcccg    480
tctcccaggt cgacgcaacc tacatgacca ccccaatctg tcccagaccc caaacaccct    540
ccttccctgc ttctctgtga tcgctgatca gcaacaacta gt                      582
```

<210> SEQ ID NO 58
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala
        35

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Gly Pro Arg Arg Pro Ala Arg Pro Leu Pro Val Arg
1               5                   10

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Ser Gly Pro Arg Arg Pro Ala Arg Pro Leu Pro Val Arg Ala Ala Ile
1               5                   10                  15

Ala Ser Glu Val Pro Val Ala Thr Thr Ser Pro Arg
            20                  25
```

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Arg Pro Ala Arg Pro Leu Pro Val Arg Gly Arg Ala
1               5                   10
```

<210> SEQ ID NO 62
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Arg Pro Ala Arg Pro Leu Pro Val Arg Ala Ala Ile Ala Ser Glu Val
1               5                   10                  15

Pro Val Ala Thr Thr Ser Pro Arg
            20
```

<210> SEQ ID NO 63
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Arg Cys Gly Asp Leu Arg Arg Ser Ala Gly Ser Gly Pro Arg Arg Pro
1               5                   10                  15

Ala Arg Pro Leu Pro Val Arg Gly Arg Ala
            20                  25
```

<210> SEQ ID NO 64
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Arg Cys Gly Asp Leu Arg Arg Ser Ala Gly Ser Gly Pro Arg Arg Pro
1               5                   10                  15

Ala Arg Pro Leu Pro Val Arg Ala Ala Ile Ala Ser Glu Val Pro Val
            20                  25                  30

Ala Thr Thr Ser Pro Arg
            35
```

<210> SEQ ID NO 65
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 65

Pro Ala Arg Pro Leu Pro Val Arg
1               5

<210> SEQ ID NO 66
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Ala Arg Pro Leu Pro Val Arg Ala Ala Ile Ala Ser Glu Val Pro
1               5                   10                  15

Val Ala Thr Thr Ser Pro Arg
            20

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Arg Pro Ala Arg Pro Leu Pro Val Arg
1               5                   10

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Arg Pro Ala Arg Pro Leu Pro Val Arg Ala Ala Ile Ala Ser Glu
1               5                   10                  15

Val Pro Val Ala Thr Thr Ser Pro Arg
            20                  25

<210> SEQ ID NO 69
<211> LENGTH: 72
<212> TYPE: DNA
<213> ORGANISM: Cuphea hookeriana
<220> FEATURE:
<221> NAME/KEY: CDS
<222> LOCATION: (1)..(72)

<400> SEQUENCE: 69 cac ctg cag gag acc tcc ctg aac cac tgc aag agc acc ggc atc ctg      48
His Leu Gln Glu Thr Ser Leu Asn His Cys Lys Ser Thr Gly Ile Leu
1               5                   10                  15 ctg gac ggc ttc ggc cgc acc ctg                                      72
Leu Asp Gly Phe Gly Arg Thr Leu
            20

<210> SEQ ID NO 70
```

```
<211> LENGTH: 24
<212> TYPE: PRT
<213> ORGANISM: Cuphea hookeriana

<400> SEQUENCE: 70

His Leu Gln Glu Thr Ser Leu Asn His Cys Lys Ser Thr Gly Ile Leu
1               5                   10                  15

Leu Asp Gly Phe Gly Arg Thr Leu
            20

<210> SEQ ID NO 71
<211> LENGTH: 72
<212> TYPE: DNA
<213> ORGANISM: Cuphea avigera
<220> FEATURE:
<221> NAME/KEY: CDS
<222> LOCATION: (1)..(72)

<400> SEQUENCE: 71 tac ctg cag gag acc tcc ctg aac cac tgc aag tcc acc ggc atc ctg      48
Tyr Leu Gln Glu Thr Ser Leu Asn His Cys Lys Ser Thr Gly Ile Leu
1               5                   10                  15 ctg gac ggc ttc ggc cgc acc ccc                                      72
Leu Asp Gly Phe Gly Arg Thr Pro
            20

<210> SEQ ID NO 72
<211> LENGTH: 24
<212> TYPE: PRT
<213> ORGANISM: Cuphea avigera

<400> SEQUENCE: 72

Tyr Leu Gln Glu Thr Ser Leu Asn His Cys Lys Ser Thr Gly Ile Leu
1               5                   10                  15

Leu Asp Gly Phe Gly Arg Thr Pro
            20

<210> SEQ ID NO 73
<211> LENGTH: 82
<212> TYPE: PRT
<213> ORGANISM: Cuphea palustris

<400> SEQUENCE: 73

Lys Arg Asp Leu Ile Trp Val Val Thr Arg Met Lys Ile Met Val Asn
1               5                   10                  15

Arg Tyr Pro Thr Trp Gly Asp Thr Ile Glu Val Ser Thr Trp Leu Ser
            20                  25                  30

Gln Ser Gly Lys Ile Gly Met Gly Arg Asp Trp Leu Ile Ser Asp Cys
        35                  40                  45

Asn Thr Gly Glu Ile Leu Val Arg Ala Thr Ser Val Tyr Ala Met Met
    50                  55                  60

Asn Gln Lys Thr Arg Arg Phe Ser Lys Leu Pro His Glu Val Arg Gln
65                  70                  75                  80

Glu Phe

<210> SEQ ID NO 74
<211> LENGTH: 82
<212> TYPE: PRT
<213> ORGANISM: Cuphea hookeriana

<400> SEQUENCE: 74

Lys Arg Asp Leu Ile Trp Val Val Ile Lys Met Gln Ile Lys Val Asn
```

```
                1               5                    10                   15
            Arg Tyr Pro Ala Trp Gly Asp Thr Val Glu Ile Asn Thr Arg Phe Ser
                            20                   25                   30

Arg Leu Gly Lys Ile Gly Met Gly Arg Asp Trp Leu Ile Ser Asp Cys
                            35                   40                   45

Asn Thr Gly Glu Ile Leu Val Arg Ala Thr Ser Ala Tyr Ala Met Met
                        50                   55                   60

Asn Gln Lys Thr Arg Arg Leu Ser Lys Leu Pro Tyr Glu Val His Gln
            65                   70                   75                   80

Glu Ile

<210> SEQ ID NO 75
            <211> LENGTH: 82
            <212> TYPE: PRT
            <213> ORGANISM: Cuphea avigera

<400> SEQUENCE: 75

Lys Arg Asp Leu Ile Trp Val Val Thr Lys Met Lys Ile Lys Val Asn
            1               5                    10                   15

Arg Tyr Pro Ala Trp Gly Asp Thr Val Glu Ile Asn Thr Trp Phe Ser
                            20                   25                   30

Arg Leu Gly Lys Ile Gly Lys Gly Arg Asp Trp Leu Ile Ser Asp Cys
                            35                   40                   45

Asn Thr Gly Glu Ile Leu Ile Arg Ala Thr Ser Ala Tyr Ala Thr Met
                        50                   55                   60

Asn Gln Lys Thr Arg Arg Leu Ser Lys Leu Pro Tyr Glu Val His Gln
            65                   70                   75                   80

Glu Ile
```

VARIANT THIOESTERASES AND METHODS OF USE

CROSS-REFERENCE TO RELATED APPLICATIONS

This application is a continuation of U.S. application Ser. No. 15/684,941, filed on Aug. 24, 2017, which is a continuation of U.S. application Ser. No. 14/808,361, filed on Jul. 24, 2015, which claims the benefit under 35 U.S.C. § 119(e) of U.S. Provisional Application No. 62/028,641, filed on Jul. 24, 2014, which are hereby incorporated herein by reference in their entireties for all purposes. This application is technologically related to the subject matter of PCT/US2014/013676, entitled "Variant Thioesterases and Methods of Use," and filed Jan. 29, 2014, which is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 5, 2015, is named SOLAP027US_SL.txt and is 180,154 bytes in size.

FIELD

The present invention relates to variant acyl-ACP thioesterases and their use in oil-producing cells, e.g., to increase enzymatic activity toward certain acyl-ACP substrates and to promote increased production of oils with desired fatty acid profiles.

BACKGROUND

Today, fats and fatty acids primarily come from vegetable and animal sources, with the notable exception of commercial production of omega-3 fatty acids by fermentation of microbes for use in baby formula and nutritional supplements. Progress is being made however toward the commercial production of tailored oils using recombinant microalgae. See PCT Publications WO2008/151149, WO2010/06032, WO2011/150410, WO2011/150411, and international patent application PCT/US12/23696.

One method for producing a desired fatty acid profile in an oleaginous organism is to introduce an acyl-ACP thioesterase transgene; e.g., a transgene from a plant that produces a desired fatty acid.

By terminating fatty acid biosynthesis, the acyl-acyl carrier protein (ACP) thioesterase (TE) functionally determines the length and identity of the fatty acid end product (Salas et al., (2002) *Archives of Biochemistry and Biophysics* 403: 25-34). Based on amino acid sequence alignments, the plant TEs have been shown to cluster into two families, FatAs, which show marked preference for 18:1-ACP with minor activity towards 18:0- and 16:0-ACPs; and FatBs, which hydrolyze primarily saturated acyl-ACPs with chain lengths that vary between 8-16 carbons (Voelker, In Genetic Engineering Volume 18. Edited by: Setlow J K. New York, Plenum Press; 1996:111-133; Ginalski, et al., *Nucl Acids Res* (2003) 31:3291-3292; and Jones, et al., (1995) *Plant Cell* 7:359-371). FatB TEs have a conserved hydrophobic 18-amino acid domain (Facciotti and Yuan (1998) European Journal of Lipid Science and Technology 100:167-172), and a conserved Asn-His-Cys catalytic triad in the C-terminal catalytic domain (Blatti, et al., PLoS ONE (2012) 7(9): e42949. doi:10.1371 and Mayer and Shanklin, *BMC Plant Biology* (2007) 7:1-11). Mayer and Shanklin, *BMC Plant Biology* (2007) 7:1-11, identify a C-terminal conserved acyl-ACP thioesterase catalytic domain characterized by a C-terminal hot dog fold encompassing the Cys-His-Asn catalytic triad.

SUMMARY

Provided is a non-natural protein, an isolated gene encoding the non-natural protein, an expression cassette expressing the non-natural protein, or a host cell comprising the expression cassette. In some embodiments, the non-natural protein has at least 80%, 85%, 90%, 91%, 92%, 93%, 94%, 95%, 96%, 97%, 98% or 99% identity to SEQ ID NO: 1 and comprises Tyrosine (Y) or Phenylalanine (F) at the position corresponding to position 163 of SEQ ID NO: 1 and/or Proline (P), Lysine (K), or Alanine (A) at the position corresponding to position 186 of SEQ ID NO: 1. In some embodiments, the non-natural protein further comprises a Lysine (K) at the position corresponding to position 228 of SEQ ID NO: 1.

In a related aspect, provided is a method for producing a triglyceride oil. In varying embodiments, the methods comprise expressing, in a host cell, the protein of mentioned immediately above, or a protein comprising at least 80%, 85%, 90%, 91%, 92%, 93%, 94%, 95%, 96%, 97%, 98% or 99% identity one of SEQ ID NOs: 3-8 that has Y or F at the position corresponding to position 163 of SEQ ID NO: 1 and/or P, K, or A at the position corresponding to position 186 of SEQ ID NO: 1. In some embodiments, the non-natural protein further comprises K at the position corresponding to position 228 of SEQ ID NO: 1. The method further includes cultivating the host cell and isolating the oil.

In another aspect, provided is a method for increasing the C8 and/or C10 fatty acids in a fatty acid profile of an oil produced by an optionally oleaginous host cell. The method includes, providing a parent gene encoding a FATB enzyme, mutating the gene to so as to have Y or F at the position corresponding to position 163 of SEQ ID NO: 1 and/or P, K, or A at the position corresponding to position 186 of SEQ ID NO: 1. In some embodiments, the non-natural protein further comprises K at the position corresponding to position 228 of SEQ ID NO: 1. In varying embodiments, the method further includes expressing the mutated gene in the host cell and producing the oil. The fatty acid profile of the oil is thereby increased in C8 and/or C10 fatty acids relative to the parent gene. Optionally, the gene encoding the FATB enzyme encodes a protein with at least 80%, 85%, 90%, 91%, 92%, 93%, 94%, 95%, 96%, 97%, 98% or 99% identity to SEQ ID NO: 1, 13 or 14.

In an embodiment, provided is a non-natural protein, an isolated gene encoding the non-natural protein, an expression cassette expressing the non-natural protein, or a host cell comprising the expression cassette. In varying embodiments, the non-natural protein has at least 80%, 85%, 90%, 91%, 92%, 93%, 94%, 95%, 96%, 97%, 98% or 99% identity to SEQ ID NO: 13 and A or K at the position corresponding to position 230 of SEQ ID NO: 13. A method for producingan oil includes expressing, in a host cell, the non-natural proteins described herein, cultivating the cell, and isolating the oil.

In another aspect, provided is a non-natural protein, an isolated gene encoding the non-natural protein, an expression cassette expressing the non-natural protein, or a host cell comprising the expression cassette. In some embodiments, the non-natural protein has at least 80%, 85%, 90%, 91%, 92%, 93%, 94%, 95%, 96%, 97%, 98% or 99% identity to SEQ ID NO: 45 and comprises A, T or V at the position corresponding to position 74 of SEQ ID NO: 45 (G96 of wild-type Gm FATA) and/or F, K or S at the position corresponding to position 69 of SEQ ID NO: 45 (L91 of wild-type Gm FATA), and/or F, A, K or V at the position corresponding to position 134 of SEQ ID NO: 45 (T156 of wild-type Gm FATA). In some embodiments, the non-natural protein further comprises A or V at the position corresponding to position 89 of SEQ ID NO: 45 (S111 of wild-type Gm FATA) and/or A at the position corresponding to position 171 of SEQ ID NO: 45 (V193 of wild-type Gm FATA), and/or A or V at the position corresponding to position 86 of SEQ ID NO: 45 (G108 of wild-type Gm FATA).

In a further aspect, provided is a method for producing a triglyceride oil. In various embodiments, the method comprises expressing, in a host cell, the protein of claim 7 or claim 8, or a protein comprising at least 80%, 85%, 90%, 91%, 92%, 93%, 94%, 95%, 96%, 97%, 98% or 99% identity to one of SEQ ID NOs: 45 and 15-29 and comprises A, T or V at the position corresponding to position 74 of SEQ ID NO: 45 (G96 of wild-type Gm FATA) and/or F, K or S at the position corresponding to position 69 of SEQ ID NO: 45 (L91 of wild-type Gm FATA), and/or F, A, K or V at the position corresponding to position 134 of SEQ ID NO: 45 (G156 of wild-type Gm FATA); cultivating the host cell; and isolating the oil. In some embodiments, the protein further comprises A or V at the position corresponding to position 89 of SEQ ID NO: 45 (S111 of wild-type Gm FATA) and/or A at the position corresponding to position 171 of SEQ ID NO: 45 (V193 of wild-type Gm FATA), and/or A or V at the position corresponding to position 86 of SEQ ID NO: 45 (G108 of wild-type Gm FATA).

In another aspect, provided is a method for increasing the C18:0 fatty acids in a fatty acid profile of an oil produced by an optionally oleaginous host cell. In some embodiments, the method further comprises providing a parent gene encoding a FATB enzyme, mutating the gene to so as to have A, T or V at the position corresponding to position 74 of SEQ ID NO: 45 (G96 of wild-type Gm FATA) and/or F, K or S at the position corresponding to position 69 of SEQ ID NO: 45 (L91 of wild-type Gm FATA), and/or F, A, K or V at the position corresponding to position 134 of SEQ ID NO: 45 (T156 of wild-type Gm FATA); expressing the mutated gene in the host cell; and producing the oil, whereby the fatty acid profile of the oil is increased in C18:0 fatty acids relative to the parent gene. In various embodiments, the method entails further mutating the gene to so as to have A or V at the position corresponding to position 89 of SEQ ID NO: 45 (S111 of wild-type Gm FATA) and/or A at the position corresponding to position 171 of SEQ ID NO: 45 (V193 of wild-type Gm FATA), and/or A or V at the position corresponding to position 86 of SEQ ID NO: 45 (G108 of wild-type Gm FATA). In some embodiments, the gene encoding the FATB enzyme encodes a protein with at least 80%, 85%, 90%, 91%, 92%, 93%, 94%, 95%, 96%, 97%, 98% or 99% identity to one of SEQ ID NOs: 45 and 15-29.

DEFINITIONS

An "acyl-ACP thioesterase" or "acyl-ACP TE" interchangeably refer to an enzyme that catalyzes the cleavage of a fatty acid from an acyl carrier protein (ACP) during lipid synthesis. Acyl-acyl carrier protein (ACP) thioesterases (TEs) hydrolyze acyl-ACP thioester bonds, releasing free fatty acids and ACP.

The term "acyl-ACP preferring TE" refers to the fatty acyl-ACP substrate specificity of a TE. An acyl-ACP preferring TE preferentially liberates a particular fatty acid from an acyl-ACP substrate. For example, the acyl-ACP preferring TE can preferentially liberate a given fatty acid over all other fatty acids in the set of C8:0, C10:0, C12:0, C14:0, C16:0, C18:0, C18:1, and C18:2 fatty acids. The preference of the acyl-ACP preferring TE can be detected as a higher V. (or a higher $k_{cat}$, or a higher V/K) in comparison to other non-preferred fatty acid-ACP substrates. The preference can be inferred from changes in fatty acid profile of a cell genetically engineered to overexpress the acyl-ACP preferring TE relative to a control cell that does not overexpress the acyl-ACP preferring TE.

Numbering of a given amino acid polymer or nucleic acid polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer.

A "variant" is a polypeptide comprising a sequence which differs in one or more amino acid position(s) from that of a parent polypeptide sequence (e.g., by substitution, deletion, or insertion). A variant may comprise a sequence which differs from the parent polypeptides sequence in up to 40% of the total number of residues of the parent polypeptide sequence, such as in up to 40%, 35%, 30%, 25%, 20%, 15%, 10%, 9%, 8%, 7%, 6%, 5%, 4%, 3% 2% or 1% of the total number of residues of the parent polypeptide sequence. For example, a variant of a 400 amino acid polypeptide sequence comprises a sequence which differs in up to 40% of the total number of residues of the parent polypeptide sequence, that is, in up to 160 amino acid positions within the 400 amino acid polypeptide sequence (such as in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 85, 90, 95, 100, 105, 110, 115, 120, 125, 130, 135, 140, 145, 150, 155, or 160 amino acid positions within the reference sequence.

"Naturally occurring" as applied to a composition that can be found in nature as distinct from being artificially produced by man. For example, a polypeptide or polynucleotide that is present in an organism (including viruses, bacteria, protozoa, insects, plants or mammalian tissue) that can be isolated from a source in nature and which has not been intentionally modified by man in the laboratory is naturally occurring. "Non-naturally occurring" (also termed "synthetic" or "artificial") as applied to an object means that the object is not naturally-occurring—i.e., the object cannot be found in nature as distinct from being artificially produced by man.

A "cell oil" or "cell fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the cell oil or cell fat has not been subjected to interesterification or other synthetic process to obtain that regiospecific triglyceride profile, rather the regiospecificity is produced naturally, by a cell or population of cells. For a cell oil or cell fat produced by a cell, the sterol profile of oil is generally determined by the sterols produced by the cell, not by artificial reconstitution of the oil by adding sterols in order to mimic the cell oil. In connection with a cell oil or cell fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "cell oil" and "cell fat" encompass such oils obtained from an organism, where the oil has undergone minimal processing, including refining, bleaching and/or degumming, which does not substantially change its triglyceride profile. A cell oil can also be a "noninteresterified cell oil", which means that the cell oil has not undergone a process in which fatty acids have been redistributed in their acyl linkages to glycerol and remain essentially in the same configuration as when recovered from the organism.

A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

"Microalgae" are microbial organisms that contain a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include eukaryotic Chlorophyceae such as *Chlorella, Dunaliella,* and *Prototheca*. Microalgae also include other microbial photosynthetic organisms that exhibit cell-cell adhesion, such as *Agmenellum, Anabaena,* and *Pyrobotrys*. Microalgae also include obligate heterotrophic microorganisms that have lost the ability to perform photosynthesis, such as certain dinoflagellate algae species and species of the genus *Prototheca*.

An "oleaginous" cell is a non-human cell capable of producing at least 20% lipid by dry cell weight, naturally or through recombinant or classical strain improvement. An "oleaginous microbe" or "oleaginous microorganism is a microbe, including a microalga that is oleaginous.

As used with respect to polypeptides or polynucleotides, the term "isolated" refers to a polypeptide or polynucleotide that has been separated from at least one other component that is typically present with the polypeptide or polynucleotide. Thus, a naturally occurring polypeptide is isolated if it has been purified away from at least one other component that occurs naturally with the polypeptide or polynucleotide. A recombinant polypeptide or polynucleotide is isolated if it has been purified away from at least one other component present when the polypeptide or polynucleotide is produced.

The terms "polypeptide" and "protein" are used interchangeably herein to refer a polymer of amino acids, and unless otherwise limited, include atypical amino acids that can function in a similar manner to naturally occurring amino acids.

The term "sequence", as used in connection with a polypeptide or nucleic acid polymer refers to the order of monomers making up the polymer or the sub-polymer or fragment having that sequence.

A "subsequence" of an amino acid or nucleotide sequence is a portion of a larger sequence or the peptide or nucleic acid sub-polymer or fragment characterized by the portion of the larger sequence.

The terms "identical" or "percent identity," in the context of two or more amino acid or nucleotide sequences, refer to two or more sequences or subsequences that are the same or have a specified percentage of amino acid residues or nucleotides that are the same, when compared and aligned for maximum correspondence, as measured using a sequence comparison algorithm or by visual inspection.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using BLAST set to default parameters.

As used with reference to polypeptides, the term "wild-type" refers to any polypeptide having an amino acid sequence present in a polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized.

The term "mutation" shall mean a change in a protein, polypeptide, or peptide sequence or subsequence produced by altering one or more nucleotides in a nucleotide coding for the protein, polypeptide, or peptide, however the alteration is obtained. For example, a mutation can be produced randomly, by PCR mutation, by synthesis of entire gene, or any other method.

The term "vector" is used herein to describe a DNA construct containing a polynucleotide. Such a vector can be propagated stably or transiently in a host cell. The vector can, for example, be a plasmid, a viral vector, or simply a potential genomic insert. Once introduced into a suitable host, the vector may replicate and function independently of the host genome, or may, in some instances, integrate into the host genome.

As used herein, the terms "expression vector" or "expression construct" or "expression cassette" refer to a nucleic acid construct, generated recombinantly or synthetically, with a series of specified nucleic acid elements that permit transcription of a particular nucleic acid in a host cell. The expression vector can be part of a plasmid, virus, or nucleic acid fragment. An "expression cassette" includes a coding nucleic acid (CDS) to be transcribed operably linked to a promoter and a 3'UTR. Optionally, and in the Examples below, the promoter of an expression cassette is a heterologous promoter.

"Exogenous gene" refers to a nucleic acid transformed into a cell. The exogenous gene may be from a different species (and so heterologous), or from the same species (and so homologous) relative to the cell being transformed. In the case of a homologous gene, it occupies a different location in the genome of the cell relative to the endogenous copy of the gene. The exogenous gene may be present in more than one copy in the cell. The exogenous gene may be maintained in a cell as an insertion into the genome or as an episomal molecule.

An "inducible promoter" is one that mediates transcription of an operably linked gene in response to a particular stimulus.

As used herein, the phrase "in operable linkage" refers to a functional linkage between two sequences, such a control sequence (typically a promoter) and the linked sequence. A promoter is in operable linkage with an exogenous gene if it can mediate transcription of the gene.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

As used herein, the term "recombinant" when used with reference, e.g., to a cell, or nucleic acid, protein, or vector, indicates that the cell, nucleic acid, protein or vector, has been modified by the introduction of an exogenous nucleic acid or protein or the alteration of a native nucleic acid or protein, or that the cell is derived from a cell so modified. Thus, recombinant cells express genes that are not found within the native (non-recombinant) form of the cell or express native genes that are otherwise abnormally expressed, over-expressed, under-expressed or not expressed at all. "Recombinant nucleic acid" as used herein refers to nucleic acid molecules that are initially synthesized through the use of laboratory methods, thereby creating nucleic acid sequences that are not normally found in nature. By using laboratory methods, recombinant nucleic acid molecules in operable linkage with different sequences (e,g., promoter, targeting sequence, etc.) is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes herein. Similarly, a "recombinant protein" is a protein made using recombinant techniques, i.e., through the expression of a recombinant nucleic acid as depicted above.

A "transit peptide" is an amino acid sequence that directs the trafficking of a polypeptide fused to the signal sequence. In connection with plastidic cells expressing the polypeptide, the transit peptide may direct trafficking of the polypeptide to the plastid (i.e., a plastid targeting peptide).

The term "polynucleotide" refers to a deoxyribonucleotide or ribonucleotide polymer, and unless otherwise limited, includes known analogs of natural nucleotides that can function in a similar manner to naturally occurring nucleotides. The term "polynucleotide" refers any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA. The term "polynucleotide" encompasses double-stranded nucleic acid molecules, as well as single-stranded molecules. In double-stranded polynucleotides, the polynucleotide strands need not be coextensive (i.e., a double-stranded polynucleotide need not be double-stranded along the entire length of both strands).

The term "host cell" refers to a cell capable of maintaining a vector either transiently or stably. Host cells include, without limitation, bacterial cells, yeast cells, insect cells, algal cells (e.g., microalgal cells), plant cells and mammalian cells. Other host cells known in the art, or which become known, are also suitable for use in the invention.

As used herein, the term "complementary" refers to the capacity for precise pairing between two nucleotides. For example, if a nucleotide at a given position of a nucleic acid molecule is capable of hybridizing with a nucleotide of another nucleic acid molecule, then the two nucleic acid molecules are considered to be complementary to one another at that position. The term "substantially complementary" describes sequences that are sufficiently complementary to one another to allow for specific hybridization under stringent hybridization conditions. In various embodiments, the variant genes encoding variant FATB genes disclosed below can be replaced with a substantially complementary gene having suitable activity.

The phrase "stringent hybridization conditions" generally refers to a temperature about 5° C. lower than the melting temperature (Tm) for a specific sequence at a defined ionic strength and pH. Exemplary stringent conditions suitable for achieving specific hybridization of most sequences are a temperature of at least about 60° C. and a salt concentration of about 0.2 molar at pH 7.0.

BRIEF DESCRIPTION OF THE DRAWINGS

FIGS. 2A-B illustrate (A) a sequence alignment of FATB thioesterases isolated from Cuphea genomes. The position of the conserved Methione relative to the Catalytic Triad (Cys, His, and Asn) and N-terminal Specificity domain is highlighted; and (B) a sequence comparison of the Cpal FATB1, Ch FATB2 and Ca FATB1 surrounding the highlighted methione (SEQ ID NOS 73-75, respectively, in order of appearance). The Ca FATB1 is unique due to the presence of a lysine instead of the methione.

FIGS. 3A-E illustrate histograms of C8-C14 fatty acid profiles of microalgal oil with mean and median values for multiple transformants of wild type and position 228 variant Cuphea hookeriana FATB2 (ChFATB2), Cuphea avigera FATB1 (CaFATB1) that depart from predictions based on prior data from an E. coli model.

DETAILED DESCRIPTION

Introduction

Figure 1:
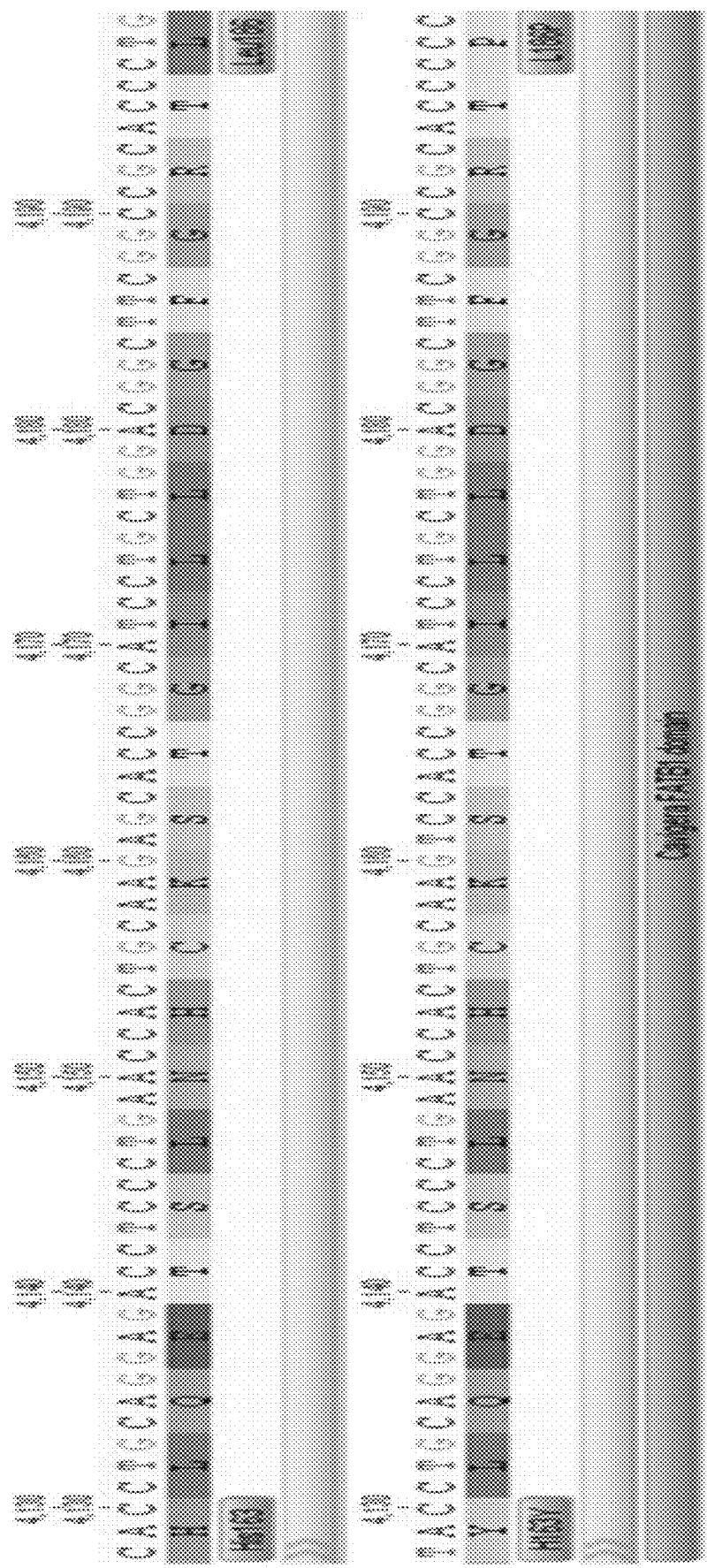
FIG. 1 illustrates a sequence alignment of the Cuphea hookeriana FATB2 (SEQ ID NOS 69 and 70, respectively, in order of appearance) versus the Cuphea avigera FATB1 (SEQ ID NOS 71 and 72, respectively, in order of appearance) illustrates the two amino acid differences between these thioesterases within their N-terminal specificity domain.

In illustrative embodiments, variant FATB acyl-ACP thioesterases described herein allow for control over acyl-ACP thioesterase substrate specificity. As a result, host cells expressing the acyl-ACP thioesterases produce oils with altered fatty acid profiles. In certain embodiments host cells expressing the variant acyl-ACP thioesterases produce triglceride-rich cell oils with fatty acid profiles characterized by elevated mid chain fatty acids such as C8:0, C10:0, C12:0, and C14:0 fatty acids. A specific embodiment includes providing a FATB acyl-ACP thioesterase gene, mutating the gene so as to alter the amino acids in the gene product at the positions corresponding to H163 and/or L186 of the reference Cuphea hookeriana FATB2 gene (SEQ ID NO: 1). Optionally, the H163 and/or L186 mutant is combined with a mutation at M228.

As described in more detail in Example 1, by expressing such variant FATB2 genes, stably integrated in the nucleus of oleaginous plastidic cells, we produced strains that exceeded wildtype ChFATB2 expressing control strains in terms of C8:0, C8:10 or the sum of C8:0 and C10:0 production, including strains that produced oils with fatty acid profiles where the C8 and C10 production exceed 9, 11, 14, or 18% of the profile. In the latter case, the C8+C10 (i.e., the sum of C8:0 and C10:0 production in the fatty acid profile as determined by FAME-GC with FID detection) level was more than doubled relative to the approximately 8% C8+C10 of the wildtype ChFATb2 strain. Specific variants with improved C8 +C10 production include those with P, K, or A at the 186 position; Y or F at the 163 position, or combinations thereof such as 186P/163Y, 186P/163F, 186K/163Y, 186K/163F, 186A/163Y or 186A/163F. Of the double mutants, we found that the H163Y/L186P variant produced an oil having particularly high concentrations of C8+C10. Using single or double variants, the C8:0 fatty acid profile percentages can be increased by 50, 60, 70, 80, 100% or more relative to a control strain expressing wildtype ChFATB2; e.g. to more than 2, 2.5, 3, or 3.5% of the fatty acid profile vs. 1.5% for the control (see Example 1).

The double mutants listed above can also be combined with a third mutation corresponding to 230 of Cuphea palustris FATB1. For many FATB genes such as Cuphea hookeriana FATB2 and Cuphea avigera FATB1, this residue corresponds to residue 228. For example, an M228K mutation in Cuphea hookeriana FATB2 expressed in an oleaginous eukaryotic microalga increased the C8/C10 ratio in the fatty acid profile of the oil from about 0.25 to about 1.0. Mutations at this position to Iso, Val, Phe, and Leu, Ala, or Thr in combination with the single or double mutants at positions 186 and 163 discussed above, can also be advantageous.

Although Cuphea hookeriana FATB2 was used as a model system, the methods of making the above-discussed mutations, methods of expressing these in an oleaginous cell, and methods of producing oil with these variants can be applied to any acyl-ACP thioesterase gene, including those having at least 80%, 85%, 90%, 91%, 92%, 93%, 94%, 95%, 96%, 97%, 98% or 99% identity to SEQ ID NO:1, or the fragment of SEQ ID NO: 1 lacking the transit peptide.

Although these variant genes were discovered using a eukaryotic microalgal expression system, the genes are more generally useful in ways that are known in the art, including their expression in higher plants to produced altered triglyceride oils. When incorporated into an oleaginous cell (e.g., of an oilseed plant, algae (e.g., microalgae)) the variant thioesterases can alter the fatty acid profiles of the cell to produce novel or more economical high-value commercial products.

The single, double or triple mutants can be used to produce an oil with a high ratio of C8:0 to C10:0 fatty acids.

For example, the C8/10 ratio can be equal to or greater than 0.3, 0.5, 0.7, 0.9, 1.0, 1.2, 1.4, 1.6, 1.8, 2.0, 2.2, 2.4, 2.6, 2.8, or 3.0.

The embodiments also encompass the residual biomass from such cells after oil extraction, oleochemicals, fuels and food products made from the oils and methods of cultivating the cells. In varying embodiments, the cells are microalgal cells, including heterotrophic or obligate heterotrophic cells, and cells classified as Chlorophyta, Trebouxiophyceae, Chlorellales, Chlorellaceae, or Chlorophyceae. The cells can also be plant cells or cells of macroalgae. Host cells having a type II fatty acid synthesis pathway are preferred. Although the examples given below use the Trebouxiophyte *Prototheca moriformis* as a host cell, the genes, constructs and methods disclosed may also find use in oilseed crops. Methods for introducing these genes into such crops such as soybean, corn, rapeseed, safflower, sunflower and others are known in the art; see, for example, U.S. Pat. Nos. 6,331,664, 5,512,482, 5,455,167, 5,667,997. Examples of oleochemicals include surfactants and solvents made from fatty acids or oils.

Accordingly, in an embodiment, provided is a non-natural protein, an isolated gene encoding the non-natural protein, an expression cassette expressing the non-natural protein, or a host cell comprising the expression cassette, wherein the non-natural protein has at least 80%, 85%, 90%, 91%, 92%, 93%, 94%, 95%, 96%, 97%, 98% or 99% identity to SEQ ID NO: 1 and comprises Y or F at the position corresponding to position 163 of SEQ ID NO: 1 and/or P, K, or A at the position corresponding to position 186 of SEQ ID NO: 1, and optionally K at the position corresponding to position 228 of SEQ ID NO: 1.

In a related embodiment, there is a method for producing a triglyceride oil. The method includes expressing, in a host cell, the protein of mentioned immediately above, or a protein comprising at least 80%, 85%, 90%, 91%, 92%, 93%, 94%, 95%, 96%, 97%, 98% or 99% identity one of SEQ ID NOs: 3-8 that has Y or F at the position corresponding to position 163 of SEQ ID NO: 1 and/or P, K, or A at the position corresponding to position 186 of SEQ ID NO: 1, and optionally K at the position corresponding to position 228 of SEQ ID NO: 1. The method further includes cultivating the host cell and isolating the oil.

In another embodiment, provided is a method for increasing the C8 and/or C10 fatty acids in a fatty acid profile of an oil produced by an optionally oleaginous host cell. The method includes, providing a parent gene encoding a FATB enzyme, mutating the gene to so as to have Y or F at the position corresponding to position 163 of SEQ ID NO: 1 and/or P, K, or A at the position corresponding to position 186 of SEQ ID NO: 1, and optionally K at the position corresponding to position 228 of SEQ ID NO: 1. The method further includes expressing the mutated gene in the host cell and producing the oil. The fatty acid profile of the oil is thereby increased in C8 and/or C10 fatty acids relative to the parent gene. Optionally, the gene encoding the FATB enzyme encodes a protein with at least 80%, 85%, 90%, 91%, 92%, 93%, 94%, 95%, 96%, 97%, 98% or 99% identity to SEQ ID NO: 1, 13 or 14.

As detailed in Example 3, compared to prior art work in *E. Coli*, the discovery of the advantage of using Ala, or Thr at position 230 of Cpal FATB1 (SEQ ID NO: 13) of in terms of C8+C10 production and/or increased C8/C10 ratio, is new and unexpected. These novel mutations are useful alone, in combination with a mutation at position 163 including the C8-favoring mutations disclosed herein, in combination with a mutation at position 186 including the C8-favoring mutations disclosed herein, or in combination with a double mutation at positions 163 and 186 including the C8-favoring mutations disclosed herein. Accordingly, in an embodiment, there is a non-natural protein, an isolated gene encoding the non-natural protein, an expression cassette expressing the non-natural protein, or a host cell comprising the expression cassette, wherein the non-natural protein has at least 80%, 85%, 90%, 91%, 92%, 93%, 94%, 95%, 96%, 97%, 98% or 99% identity to SEQ ID NO: 13 and A or K at the position corresponding to position 230 of SEQ ID NO: 13. A method for producingan oil includes expressing, in a host cell, the non-natural proteins described herein, cultivating the cell, and isolating the oil.

Variant Acyl-ACP Thioesterases

The variant TEs can be used in genetic constructs and genetically engineered oleaginous cells (e.g., plants, algae, microalgae) with one or more exogenous genes to produce fatty acids, acylglycerides, or derivatives thereof. For example, microalgae or oilseed crops that would naturally, or through genetic modification, produce high levels of lipids can be engineered (or further engineered) to express an exogenous variant fatty acyl-ACP thioesterase, which can facilitate the cleavage of fatty acids from acyl carrier protein (ACP) during fatty acid synthesis. The fatty acids synthesized may be incorporated into acyl glycerides including triacylglycerides (TAGs, triglycerides). The TAGs can be recovered or, through further enzymatic processing within the cell, or in vitro, yield other useful compounds.

In an embodiment, the variant fatty acyl-ACP thioesterases are designed based on the desired specificity for a growing (during fatty acid synthesis) fatty acyl group having a particular carbon chain length. A specificity domain is selected based on its preference for a particular fatty acyl ACP substrate and/or for its ability to influence, increase and/or promote the production of fatty acids of a desired carbon chain length.

Generally, the variant fatty acyl-ACP thioesterases have preferential substrate specificity for mid-chain ACP-fatty acyl substrates (e.g., to liberate C8, C10, C12, and/or C14 fatty acids). In varying embodiments, the specificity domain in the N-terminus of the acyl-ACP thioesterase is heterologous (e.g., due to point mutations and/or domain swapping) to the C-terminal catalytic domain. In certain embodiments, the fatty acid chain length substrate specificity and/or preference of the specificity domain and the catalytic domain is the same or within 1-2 carbons. For example, in varying embodiments, the variant acyl-acyl carrier protein (ACP) thioesterase (TE) comprises:

Codon-Optimization for Expression

DNA encoding a polypeptide to be expressed in a microorganism, e.g., a variant acyl-ACP thioesterase and selectable marker can be codon-optimized cDNA. Methods of recoding genes for expression in microalgae are described in U.S. Pat. No. 7,135,290. Additional information for codon optimization is available, e.g., at the Codon Usage Database at kazusa.or.jp/codon/. The table for *Prototheca* preferred codon usage is also provided in U.S. Patent Publ. No. 2012/0283460, Table 1 of which is hereby incorporated herein by reference.

Expression and Targeting to Plastids

Proteins expressed in the nuclear genome of *Prototheca* can be targeted to the plastid using plastid targeting signals. Plastid targeting sequences endogenous to *Chlorella* are known, such as genes in the *Chlorella* nuclear genome that encode proteins that are targeted to the plastid; see for example GenBank Accession numbers AY646197 and AF499684, and in one embodiment, such control sequences are used in the vectors described herein, e.g., to target expression of a protein to a *Prototheca* plastid.

The Examples below describe the use of algal plastid targeting sequences to target heterologous proteins to the correct compartment in the host cell. cDNA libraries were made using *Prototheca moriformis* and *Chlorella protothecodies* cells and are described in the Examples of U.S. Patent Publ. No. 2012/0283460 and in PCT Application No. PCT/US2009/066142. Amino acid sequences of the algal plastid targeting sequences identified from the cDNA libraries useful plastid targeting of recombinantly expressed variant acyl-ACP thioesterases are provided in U.S. Patent Publ. No. 2012/0283460 and herein. In varying embodiments, the plastid transit peptide comprises an amino acid sequence selected from the group consisting of

```
                                        (SEQ ID NO: 58)
MATASTFSAFNARCGDLRRSAGSGPRRPARPLPVRGRA, (SEQ ID NO: 59)
SGPRRPARPLPVR, (SEQ ID NO: 60)
SGPRRPARPLPVRAAIASEVPVATTSPR, (SEQ ID NO: 61)
RPARPLPVRGRA, (SEQ ID NO: 62)
RPARPLPVRAAIASEVPVATTSPR, (SEQ ID NO: 63)
RCGDLRRSAGSGPRRPARPLPVRGRA, (SEQ ID NO: 64)
RCGDLRRSAGSGPRRPARPLPVRAAIASEVPVATTSPR, (SEQ ID NO: 65)
PARPLPVR, (SEQ ID NO: 66)
PARPLPVRAAIASEVPVATTSPR, (SEQ ID NO: 67)
RRPARPLPVR,
and (SEQ ID NO: 68)
RRPARPLPVRAAIASEVPVATTSPR.
```

Where novel FATB variants are disclosed here, it will be understood that a variety of heterologous plastid transit peptides can be used. In other words, the non-targeting peptide domain is more highly conserved. Accordingly, embodiments described herein feature the novel FATB enzymatic domain with or without a plastid targeting sequence. For example, where a percent identity to a novel FATB gene is given herein, the same identity can be applied (where specified) to the same sequence absent the targeting peptide. A substitute targeting peptide can optionally be used in connection with such a sequence.

Host Cells—Oil- or Lipid-Producing Microorganisms

Any species of organism that produces suitable lipid and/or hydrocarbon can be used, although microorganisms that naturally produce high levels of suitable lipid and/or hydrocarbon are preferred. Production of hydrocarbons by microorganisms is reviewed by Metzger et al. Appl Microbiol Bioethanol (2005) 66: 486-496 and A Look Back at the U.S. Department of Energy's Aquatic Species Program: Biodiesel from Algae, NREUTP-580-24190, John Sheehan, Terri Dunahay, John Benemann and Paul Roessler (1998).

Considerations for the selection of microorganisms include, in addition to production of suitable lipids or hydrocarbons for production of oils, fuels, and oleochemicals: (1) high lipid content as a percentage of cell weight; (2) ease of growth; (3) ease of genetic engineering; and (4) ease of biomass processing. In particular embodiments, the wild-type or genetically engineered microorganism yields cells that are at least 40%, at least 45%, at least 50%, at least 55%, at least 60%, at least 65%, or at least 70% or more lipid. Preferred organisms grow heterotrophically (on sugars in the absence of light) or can be engineered to do so using, for example, methods disclosed herein. The ease of transformation and availability of selectable markers and promoters, constitutive or inducible, that are functional in the microorganism affect the ease of genetic engineering.

Processing considerations can include, for example, the availability of effective means for lysing the cells.

A. Algae

In one embodiment, the microorganism is a microalgae. Nonlimiting examples of microalgae that can be used for expression of variant acyl-ACP thioestesterases include, e.g., *Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri subsalsum, Chaetoceros* sp., *Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora* (strain SAG 37.88), *Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides* (including any of UTEX strains 1806, 411, 264, 256, 255, 250, 249, 31, 29, 25), *Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris f. tertia, Chlorella vulgaris* var. *autotrophica, Chlorella vulgaris* var. *viridis, Chlorella vulgaris* var. *vulgaris, Chlorella vulgaris* var. *vulgaris f. tertia, Chlorella vulgaris* var. *vulgaris f. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena, Franceia* sp., *Fragilaria crotonensis, Fragilaria* sp., *Gleocapsa* sp., *Gloeothamnion* sp., *Hymenomonas* sp., *Isochrysis aff. galbana, Isochrysis galbana, Lepocinclis, Micractinium, Micractinium* (UTEX LB 2614), *Monoraphidium minutum, Monoraphidium* sp., *Nannochloris* sp., *Nannochloropsis salina, Nannochloropsis* sp., *Navicula acceptata, Navicula biskanterae, Navicula pseudote nelloides, Navicula pelliculosa, Navicula saprophila, Navicula* sp., *Nephrochloris* sp., *Nephroselmis* sp., *Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, ParaChlorella kessleri, Pascheria acidophila, Pavlova* sp., *Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, PseudoChlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Tetraedron, Tetraselmis* sp., *Tetraselmis suecica, Thalassiosira weissflogii,* and *Viridiella fridericiana.*

Illustrative host cells feature oleaginous cells that produce altered fatty acid profiles and/or altered regiospecific distribution of fatty acids in glycerolipids, and products produced from the cells. Examples of oleaginous cells include microbial cells having a type II lipid biosynthesis pathway, including plastidic oleaginous cells such as those of oleaginous algae. Specific examples of cells include heterotrophic or obligate eukaryotic heterotophic microalgae of the phylum Chlorpophya, the class Trebouxiophytae, the order Chlorellales, or the family Chlorellacae. Examples of oleaginous microalgae are provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25%, 30%, 40%, 50%, 60%, 70%, 80%, 85%, or about 90% oil by cell weight, ±5%. The above mentioned publications also disclose methods for cultivating such cells and extracting oil, especially from microalgal cells; such methods are applicable to the cells disclosed herein. In any of the embodiments described herein, the cells can be heterotrophic cells comprising an exogenous invertase gene so as to allow the cells to produce oil from a sucrose feedstock.

Illustrative embodiments of host cells include recombinant oleaginous cells expressing one or more exogenous genes encoding fatty acid biosynthesis enzymes. As a result, some embodiments feature cell oils never before obtainable in a cell oil. In some cases, the cell oils were not obtainable from a non-plant or non-seed oil, or not obtainable at all.

The oleaginous cells produce a storage oil, which may be stored in storage vesicles of the cell. A raw cell oil may be obtained from the cells by disrupting the cells and isolating the oil. The oils produced may be refined, bleached and deodorized (RBD) as known in the art or as described in WO2010/120939. The raw or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride cell oil is given, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). Because the cells are oleaginous, in some cases the storage oil will constitute the bulk of all the TAGs in the cell.

In varying embodiments, the host cell is a plastidic cell, e.g., a heterotrophic microalgae of the phylum Chlorpophya, the class Trebouxiophytae, the order Chlorellales, or the family Chlorellacae. In varying embodiments, the cell is oleaginous and capable of accumulating at least 40% oil by dry cell weight. The cell can be an obligate heterotroph, such as a species of *Prototheca*, including *Prototheca moriformis* or *Prototheca zopfii*. The nucleic acid encoding the variant acyl-ACP TEs described herein can also be expressed in autotrophic algae or plants. Optionally, the cell is capable of using sucrose to produce oil and a recombinant invertase gene may be introduced to allow metabolism of sucrose, as described in PCT Publications WO2008/151149, WO2010/06032, WO2011/150410, WO2011/150411, and international patent application PCT/US12/23696. The invertase may be codon optimized and integrated into a chromosome of the cell, as may all of the genes mentioned here. Codon usage for different algal and plant species of interest is known in the art and can be found, e.g., on the internet at the Codon Usage Database at kazusa.or.jp/codon/.

The polynucleotides encoding the variant acyl-ACP TEs described herein further can be expressed in a wide variety of plant host cells. Of particular interest are plant cells of plants involved in the production of vegetable oils for edible and industrial uses, including e.g., temperate oilseed crops. Plants of interest include, but are not limited to, grapeseed (Canola and High Erucic Acid varieties), sunflower, safflower, cotton, Cuphea, soybean, peanut, coconut and oil palms, and corn. See, U.S. Pat. Nos. 5,850,022; 5,723,761; 5,639,790; 5,807,893; 5,455,167; 5,654,495; 5,512,482;5,298,421;5,667,997; and 5,344,771; 5,304,481.

Oils with Non-Naturally Occurring Fatty Acid Profiles

Oils disclosed herein are distinct from other naturally occurring oils that are high in mid-chain fatty acids, such as palm oil, palm kernel oil, and coconut oil. For example, levels of contaminants such as carotenoids are far higher in palm oil and palm kernel oil than in the oils described herein. Palm and palm kernel oils in particular contain alpha and beta carotenes and lycopene in much higher amounts than is in the oils described herein. In addition, over 20 different carotenoids are found in palm and palm kernel oil, whereas the Examples demonstrate that the oils described herein contain very few carotenoids species and very low levels. In addition, the levels of vitamin E compounds such as tocotrienols are far higher in palm, palm kernel, and coconut oil than in the oils described herein.

Generally, *Prototheca* strains have very little or no fatty acids with the chain length C8-C14. For example, *Prototheca* strains *Prototheca moriformis* (UTEX 1435), *Prototheca krugani* (UTEX 329), *Prototheca stagnora* (UTEX 1442) and *Prototheca zopfii* (UTEX 1438) produce no (or undetectable amounts) C8 fatty acids, between 0-0.01% C10 fatty acids, between 0.03-2.1% C12 fatty acids and between 1.0-1.7% C14 fatty acids.

In some cases, the oleaginous cells (e.g, *Prototheca* strains) containing a transgene encoding a variant fatty acyl-ACP thioesterase has a fatty acid profile characterized by 5-10%, 10-20%, 20-30%, 30-40%, 40-50%, 50-60%, 60-70%, 70-80%, 80-90%, or 90-99% C8, C10, C12, or C14 fatty acids. In other cases, the *Prototheca* strains containing a transgene encoding a fatty acyl-ACP thioesterase that has activity towards fatty acyl-ACP substrates of chain length C12 and C14 and produces fatty acids of the chain length C12 and the chain length C14 at a ratio of 1:1+/−20%.

In some instances, keeping the transgenic *Prototheca* strains under constant and high selective pressure to retain exogenous genes is advantageous due to the increase in the desired fatty acid of a specific chain length. High levels of exogenous gene retention can also be achieved by inserting exogenous genes into the nuclear chromosomes of the cells using homologous recombination vectors and methods disclosed herein. Recombinant cells containing exogenous genes integrated into nuclear chromosomes are also contemplated.

Microalgal oil can also include other constituents produced by the microalgae, or incorporated into the microalgal oil from the culture medium. These other constituents can be present in varying amount depending on the culture conditions used to culture the microalgae, the species of microalgae, the extraction method used to recover microalgal oil from the biomass and other factors that may affect microalgal oil composition. Non-limiting examples of such constituents include carotenoids, present from 0.1-0.4 micrograms/ml, chlorophyll present from 0-0.02 milligrams/kilogram of oil, gamma tocopherol present from 0.4-0.6 milligrams/100 grams of oil, and total tocotrienols present from 0.2-0.5 milligrams/gram of oil.

The other constituents can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-crytoxanthin), and various organic or inorganic compounds.

In some cases, the oil extracted from *Prototheca* species comprises no more than 0.02 mg/kg chlorophyll. In some cases, the oil extracted from *Prototheca* species comprises no more than 0.4 mcg/ml total carotenoids. In some cases the *Prototheca* oil comprises between 0.40-0.60 milligrams of gamma tocopherol per 100 grams of oil. In other cases, the *Prototheca* oil comprises between 0.2-0.5 milligrams of total tocotrienols per gram of oil.

Oils produced from host cells expressing a variant acyl-ACP thioesterase will have an isotopic profile that distinguishes it, e.g., from blended oils from other sources. The stable carbon isotope value δ13C is an expression of the ratio of 13C/12C relative to a standard (e.g. PDB, carbonite of fossil skeleton of *Belemnite americana* from Peedee formation of South Carolina). The stable carbon isotope value δ13C (0/00) of the oils can be related to the δ13C value of the feedstock used. In some embodiments the oils are derived from oleaginous organisms heterotrophically grown on sugar derived from a C4 plant such as corn or sugarcane. In some embodiments, the δ13C (0/00) of the oil is from 10 to −17 0/00 or from 13 to −16 0/00.

In varying embodiments, a host cell expressing a variant acyl-ACP thioesterase comprising all or specificity-determining residues of a specificity domain from a C10-preferring acyl-ACP thioesterase (e.g., an acyl-ACP thioesterase from *Cuphea hookeriana*), and a catalytic domain from a C12-preferring acyl-ACP thioesterase (e.g., an acyl-ACP thioesterase from Cuphea wrightii or Umbellularia californica) produces an oil comprising at least about 10% C12:0 fatty acids, and at least about 10% C14:0 fatty acids.

In varying embodiments, a host cell expressing a variant acyl-ACP thioesterase comprising all or specificity-determining residues of a modified specificity domain of a first acyl-ACP thioesterase having one or both His163→Tyr or Leu186→Pro substitutions (or at positions corresponding to His163→Tyr or Leu186→Pro of SEQ ID NO:61), and a catalytic domain of a second acyl-ACP thioesterase produces an oil comprising at least about 5%, e.g., at least about 6%, 7%, 8%, 9%, 10%, 12%, 15%, or more, C8:0 fatty acids or at least about 5%, e.g., at least about 6%, 7%, 8%, 9%, 10%, 12%, 15%, or more, C10:0 fatty acids or a C8:0/C10:0 ratio that is at least about 5%, e.g., at least about 6%, 7%, 8%, 9%, 10%, 12%, 15%, or more. As appropriate, the specificity domain can be derived from a C8:0-, C10:0- or a C12:0- preferring acyl-ACP thioesterase and independently the catalytic domain can be derived from a C8:0-, C10:0- or a C12:0- preferring acyl-ACP thioesterase. The specificity domain and the catalytic domain can be from the same or different acyl-ACP thioesterases. In varying embodiments, a host cell expressing a variant acyl-ACP thioesterase comprising all or specificity-determining residues of a modified specificity domain from a C10-preferring acyl-ACP thioesterase (e.g., an acyl-ACP thioesterase from Cuphea hookeriana having one or both His163→Tyr or Leu186→Pro substitutions), and a catalytic domain from a C10-preferring acyl-ACP thioesterase (e.g., an acyl-ACP thioesterase from Cuphea hookeriana) produces an oil comprising at least about 5%, e.g., at least about 6%, 7%, 8%, 9%, 10%, 12%, 15%, or more, C8:0 fatty acids or at least about 5%, e.g., at least about 6%, 7%, 8%, 9%, 10%, 12%, 15%, or more, C10:0 fatty acids or a C8:0/C10:0 ratio that is at least about 5%, e.g., at least about 6%, 7%, 8%, 9%, 10%, 12%, 15%, or more.

In varying embodiments, a host cell expressing a variant acyl-ACP thioesterase comprising all or specificity-determining residues of a specificity domain from a C14-preferring acyl-ACP thioesterase (e.g., an acyl-ACP thioesterase from Cinnamomum camphorum), and a catalytic domain from a C12-preferring acyl-ACP thioesterase (e.g., an acyl-ACP thioesterase from Cuphea wrightii or Umbellularia californica) produces an oil comprising C12:0 fatty acids and C14:0 fatty acid at an approximate 1:1 ratio; e.g, a ratio of 1:1+/−20%.

Further, host cells expressing a variant acyl-ACP thioesterase comprising 5 or more amino acid residues extending from the C-terminus of a linker domain positioned N-terminal to the hydrophobic domain, produce an oil comprising relatively elevated mid-chain length fatty acids (e.g., C8:0, C10:0, C12:0, C14:0) in comparison to host cells expressing the same acyl-ACP thioesterase without a linker domain. In varying embodiments, host cells expressing a variant acyl-ACP thioesterase comprising 5 or more amino acid residues extending from the C-terminus of a linker domain positioned N-terminal to the hydrophobic domain, produce an oil comprising mid-chain length fatty acids increased by at least 1-fold, 2-fold, 3-fold, or more, in comparison to host cells expressing the same acyl-ACP thioesterase without a linker domain.

In a specific embodiment, a recombinant cell comprises nucleic acids operable to express a product of an exogenous gene encoding a variant acyl-ACP thioesterase exogenous gene encoding an active acyl-ACP thioesterase that catalyzes the cleavage of mid-chain fatty acids from ACP. As a result, in one embodiment, the oil produced can be characterized by a fatty acid profile elevated in C8, C10, C12, and/or C14 fatty acids and reduced in C16, C18, and C18:1 fatty acids as a result of expression of the recombinant nucleic acids. In varying embodiments, the increase in C8, C10, C12, and/or C14 fatty acids is greater than 1%, 2%, 3%, 4%, 5%, 6%, 7%, 8%, 9%, 10%, 20%, 30%, 40%, 50%, 60%, 70%, from 75-85%, from 70-90%, from 90-200%, from 200-300%, from 300-400%, from 400-500%, or greater than 500%.

In some embodiments, an additional genetic modification to increase the level of mid-chain fatty acids in the cell or oil of the cell includes the expression of an exogenous lysophosphatidic acid acyltransferase gene encoding an active lysophosphatidic acid acyltransferase (LPAAT) that catalyzes the transfer of a mid-chain fatty-acyl group to the sn-2 position of a substituted acylglyceroester. In a specific related embodiment, both an exogenous acyl-ACP thioesterase and LPAAT are stably expressed in the cell. As a result of introducing recombinant nucleic acids into an oleaginous cell (and especially into a plastidic microbial cell) an exogenous mid-chain-specific thioesterase and an exogenous LPAAT that catalyzes the transfer of a mid-chain fatty-acyl group to the sn-2 position of a substituted acylglyceroester, the cell can be made to increase the percent of a particular mid-chain fatty acid in the triacylglycerides (TAGs) that it produces by 10, 20 30, 40, 50, 60, 70, 80, 90-fold, or more. Introduction of the exogenous LPAAT can increase mid-chain fatty acids at the sn-2 position by 1, 2, 3, 4 fold or more compared to introducing an exogenous mid-chain preferring acyl-ACP thioesterase alone. In an embodiment, the mid-chain fatty acid is greater than 30, 40, 50 60, 70, 80, or 90% of the TAG fatty acids produced by the cell. In various embodiments, the mid-chain fatty acid is capric, caprylic, lauric, myristic, and/or palmitic.

In varying embodiments, the gene encoding an lysophosphatidic acid acyltransferase (LPAAT) is selected from the group consisting of Arabidopsis thaliana 1-acyl-sn-glycerol-3-phosphate acyltransferase (GenBank Accession No. AEE85783), Brassica juncea 1-acyl-sn-glycerol-3-phosphate acyltransferase (GenBank Accession No. ABQ42862), Brassica juncea 1-acyl-sn-glycerol-3-phosphate acyltransferase (GenBank Accession No. ABM92334), Brassica napus 1-acyl-sn-glycerol-3-phosphate acyltransferase (GenBank Accession No. CAB09138), Chlamydomonas reinhardtii lysophosphatidic acid acyltransferase (GenBank Accession No. EDP02300), Cocos nucifera lysophosphatidic acid acyltransferase (GenBank Acc. No. AAC49119), Limnanthes alba lysophosphatidic acid acyltransferase (GenBank Accession No. EDP02300), Limnanthes douglasii 1-acyl-sn-glycerol-3-phosphate acyltransferase (putative) (GenBank Accession No. CAA88620), Limnanthes douglasii acyl-CoA:sn-1acylglycerol-3-phosphate acyltransferase (GenBank Accession No. ABD62751), Limnanthes douglasii 1-acylglycerol-3-phosphate O-acyltransferase (GenBank Accession No. CAA58239), Ricinus communis 1-acyl-sn-glycerol-3-phosphate acyltransferase (GenBank Accession No. EEF39377).

Alternately, or in addition to expression of an exogenous LPAAT, the cell may comprise recombinant nucleic acids that are operable to express an exogenous KASI or KASIV enzyme and optionally to decrease or eliminate the activity of a KASII, which is particularly advantageous when a mid-chain-preferring acyl-ACP thioesterase is expressed. Engineering of Prototheca cells to overexpress KASI and/or KASIV enzymes in conjunction with a mid-chain preferring acyl-ACP thioesterase can generate strains in which production of C10-C12 fatty acids is at least about 40% of total fatty acids, e.g., at least about 45%, 50%, 55%, 60% or more, of total fatty acids. Mid-chain production can also be increased by suppressing the activity of KASI and/or KASII (e.g., using a knockout or knockdown). Chromosomal knockout of different alleles of Prototheca moriformis (UTEX 1435) KASI in conjunction with overexpression of a mid-chain preferring acyl-ACP thioesterase can achieve fatty acid profiles that are at least about 60% C10-C14 fatty acids, e.g., at least about 65%, 70%, 75%, 80%, 85% or more C10-C14 fatty acids. Elevated mid-chain fatty acids can also be achieved as a result of expression of KASI RNA hairpin polynucleotides. In addition to any of these modifications, unsaturated or polyunsaturated fatty acid production can be suppressed (e.g., by knockout or knockdown) of a SAD or FAD enzyme.

In an embodiment, one of the above described high mid-chain producing cells is further engineered to produce a low polyunsaturated oil by knocking out or knocking down one or more fatty acyl desaturases. Accordingly, the oil produced has high stability.

The high mid-chain oils or fatty acids derived from hydrolysis of these oils may be particularly useful in food, fuel and oleochemical applications including the production of lubricants and surfactants. For example, fatty acids derived from the cells can be esterified, cracked, reduced to an aldehyde or alcohol, aminated, sulfated, sulfonated, or subjected to other chemical process known in the art.

The invention, having been described in detail above, is exemplified in the following examples, which are offered to illustrate, but not to limit, the claimed invention.

EXAMPLES

The following examples are offered to illustrate, but not to limit the claimed invention.

Example 1

Mutagenesis of Cuphea Hookeriana FATB2

We modified the activity and specificity of a FATB2 thioesterase originally isolated from *Cuphea hookeriana* (Ch FATB2, accession U39834), using site directed mutagenesis of H163 and L186 within the enzymatic core (H163 and L186 within Ch FATB2.).

For the above examples, an expression construct was used that targeted the FATB variants and selection markers to the Thi4 (thiamine biosynthesis) locus. An antibiotic resistance gene was used to select for resistance to G418 antibiotic. The UAPA promoter was used to drive FATB. The construct is exemplifided in SEQ ID NO: 9.

As disclosed in PCT/US2014/013676 we discovered that grafting the Cuphea avigera FATB1 (Ca FATB1) N-terminal specificity domain (FIG. 2B) onto the Cuphea hookeriana FATB2 (FIG. 2A) improves activity and C8-C10 ratio. *Prototheca moriformis* transfomants expressing Ch FATB2 H163Y, L186P (D3130) mutants exhibited about 2 fold increase in the average C8-C10 sum as well as a shift in fatty acid profile specificity relative to the wild-type Ch FATB2 (D3042).

The His at position 163 within the Ch FATB2 (FIG. 2A) is highly conserved across FATB thioesterases. In contrast, the Leu at position 186 within the Ch FATB is rare. In other FATB's, position 186 is typically occupied by a Pro or Leu. Due to these observations and also the increased activity and shift in fatty acid profile specificity of *Prototheca moriformis* strains expressing the Ch FATB2 H163Y, L186P mutant (D3130), we identified H163 and L186 as "hot spots" for mutagenesis and performed exhaustive mutagenesis at both H163 and L186 to explore the effect of amino acid combinations on activity of the Ch FATB2 when expressed within the *Prototheca moriformis* model system. Details of the cloning system are given in PCT/US2014/013676.

Thirty-eight individual Ch FATB2 variants were generated and their effect on C8:0 and C10:0 fatty acid accumulation was quantified. Transformants with C8-C10 sum within 3 standard deviations above the wild-type Ch FATB2 control(D3598) were classified as positive and those within 3 standard deviations below were scored as negative. See Table 1. The remaining transformants were classified as neutral. As shown in Table 1, *Prototheca moriformis* transformed with six of the Ch FATB2 mutants (D3570, D3573, D3582, D3584, D3588, and D3599) accumulated C8:0-C10:0 fatty acids within 3 standard above transformants expressing the wild type Ch FATB2 (D3598) control.

TABLE 1

Analysis of FATB varaiants for C8-C14 fatty acid productionin *P. moriformis*.*

| Ch FABT2 variant | | C8:0 | C10:0 | C12:0 | C14:0 | C8-C10sum |
|---|---|---|---|---|---|---|
| D3565-186V | average | 1.82 | 6.86 | 0.20 | 1.64 | 8.68 |
| | STDEV | 0.28 | 0.76 | 0.02 | 0.05 | 1.04 |
| D3566-186Y | average | 1.94 | 7.17 | 0.22 | 1.72 | 9.11 |
| | STDEV | 0.45 | 1.11 | 0.03 | 0.08 | 1.56 |
| D3567-186W (negative) | average | 0.78 | 3.98 | 0.16 | 1.66 | 4.76 |
| | STDEV | 0.06 | 0.20 | 0.05 | 0.02 | 0.26 |
| D3568-186T | average | 1.78 | 7.00 | 0.21 | 1.61 | 8.78 |
| | STDEV | 0.38 | 0.89 | 0.02 | 0.06 | 1.27 |
| D3569-186S | average | 1.85 | 7.05 | 0.20 | 1.61 | 8.9 |
| | STDEV | 0.32 | 0.75 | 0.02 | 0.06 | 1.07 |
| D3570-186P (positive) | average | 2.86 | 8.68 | 0.25 | 1.65 | 11.54 |
| | STDEV | 0.25 | 0.61 | 0.02 | 0.05 | 0.86 |
| D3571-186F | average | 1.46 | 5.98 | 0.19 | 1.62 | 7.44 |
| | STDEV | 0.32 | 0.78 | 0.02 | 0.06 | 1.1 |
| D3572-186M | average | 1.48 | 6.13 | 0.18 | 1.59 | 7.61 |
| | STDEV | 0.23 | 0.46 | 0.01 | 0.03 | 0.69 |
| D3573-186K(positive) | average | 2.62 | 8.74 | 0.23 | 1.54 | 11.36 |
| | STDEV | 0.66 | 1.33 | 0.03 | 0.05 | 1.99 |
| D3574-186I | average | 1.56 | 6.35 | 0.18 | 1.63 | 7.91 |
| | STDEV | 0.26 | 0.55 | 0.01 | 0.04 | 0.81 |
| D3575-186H | average | 1.97 | 7.38 | 0.19 | 1.60 | 9.35 |
| | STDEV | 0.29 | 0.58 | 0.01 | 0.03 | 0.87 |
| D3576-186G | average | 1.41 | 5.83 | 0.18 | 1.70 | 7.24 |
| | STDEV | 0.25 | 0.69 | 0.02 | 0.07 | 0.94 |
| D3577-186E | average | 2.14 | 7.91 | 0.21 | 1.68 | 10.05 |
| | STDEV | 0.54 | 1.29 | 0.03 | 0.08 | 1.83 |

TABLE 1-continued

Analysis of FATB varaiants for C8-C14 fatty acid productionin *P. moriformis*.*

| Ch FABT2 variant | | C8:0 | C10:0 | C12:0 | C14:0 | C8-C10sum |
|---|---|---|---|---|---|---|
| D3578-186Q | average | 2.07 | 7.69 | 0.20 | 1.61 | 9.76 |
| | STDEV | 0.46 | 0.96 | 0.02 | 0.06 | 1.42 |
| D3579-186C | average | 0.95 | 4.77 | 0.16 | 1.60 | 5.72 |
| | STDEV | 0.07 | 0.23 | 0.01 | 0.03 | 0.3 |
| D3580-186N | average | 2.25 | 7.93 | 0.21 | 1.55 | 10.18 |
| | STDEV | 0.33 | 0.79 | 0.02 | 0.04 | 1.12 |
| D3581-186R | average | 2.21 | 7.74 | 0.22 | 1.63 | 9.95 |
| | STDEV | 0.73 | 1.90 | 0.04 | 0.07 | 2.63 |
| D3582-186A(positive) | average | 2.39 | 8.74 | 0.23 | 1.58 | 11.13 |
| | STDEV | 0.78 | 1.94 | 0.04 | 0.06 | 2.72 |
| D3603-186D | average | 1.91 | 7.02 | 0.19 | 1.54 | 8.93 |
| | STDEV | 0.41 | 1.14 | 0.02 | 0.05 | 1.55 |
| D3583-163V(negative) | average | 0.00 | 0.12 | 0.03 | 1.89 | 0.12 |
| | STDEV | 0.00 | 0.07 | 0.04 | 0.21 | 0.07 |
| D3584-163Y(positive) | average | 3.71 | 10.52 | 0.30 | 1.61 | 14.23 |
| | STDEV | 0.92 | 1.75 | 0.04 | 0.04 | 2.67 |
| D3585-163W | average | 1.11 | 4.88 | 0.18 | 1.67 | 5.99 |
| | STDEV | 0.12 | 0.28 | 0.01 | 0.04 | 0.4 |
| D3586-163T(negative) | average | 0.00 | 0.01 | 0.01 | 1.78 | 0.01 |
| | STDEV | 0.00 | 0.03 | 0.02 | 0.13 | 0.03 |
| D3587-163P(negative) | average | 0.00 | 0.01 | 0.01 | 1.84 | 0.01 |
| | STDEV | 0.00 | 0.03 | 0.03 | 0.14 | 0.03 |
| D3588-163F(positive) | average | 3.79 | 10.82 | 0.31 | 1.59 | 14.61 |
| | STDEV | 0.54 | 0.77 | 0.01 | 0.03 | 1.31 |
| D3589-163K(negative) | average | 0.00 | 0.01 | 0.06 | 1.79 | 0.01 |
| | STDEV | 0.00 | 0.02 | 0.01 | 0.07 | 0.02 |
| D3590-163L | average | 1.95 | 7.49 | 0.20 | 1.66 | 9.44 |
| | STDEV | 0.38 | 1.15 | 0.03 | 0.08 | 1.53 |
| D3591-163I(negative) | average | 0.06 | 0.70 | 0.07 | 1.74 | 0.76 |
| | STDEV | 0.02 | 0.15 | 0.01 | 0.11 | 0.17 |
| D3592-163G(negative) | average | 0.00 | 0.01 | 0.06 | 1.81 | 0.01 |
| | STDEV | 0.00 | 0.02 | 0.01 | 0.03 | 0.02 |
| D3593-163E(negative) | average | 0.00 | 0.02 | 0.06 | 1.99 | 0.02 |
| | STDEV | 0.01 | 0.05 | 0.02 | 0.20 | 0.06 |
| D3594-163Q(negative) | average | 0.06 | 0.69 | 0.07 | 1.74 | 0.75 |
| | STDEV | 0.05 | 0.36 | 0.01 | 0.06 | 0.41 |
| D3595-163C(negative) | average | 0.00 | 0.02 | 0.01 | 1.80 | 0.02 |
| | STDEV | 0.00 | 0.05 | 0.02 | 0.17 | 0.05 |
| D3596-163R(negative) | average | 0.00 | 0.01 | 0.01 | 1.92 | 0.01 |
| | STDEV | 0.00 | 0.04 | 0.02 | 0.36 | 0.04 |
| D3597-163A(negative) | average | 0.00 | 0.00 | 0.01 | 1.72 | 0 |
| | STDEV | 0.00 | 0.00 | 0.03 | 0.14 | 0 |
| D3600-163S12 (negative) | average | 0.00 | 0.00 | 0.02 | 1.74 | 0 |
| | STDEV | 0.00 | 0.00 | 0.03 | 0.12 | 0 |
| D3601-163M(negative) | average | 0.02 | 0.76 | 0.02 | 1.75 | 0.78 |
| | STDEV | 0.05 | 0.16 | 0.04 | 0.15 | 0.21 |
| D3602-163N(negative) | average | 0.00 | 0.00 | 0.01 | 1.74 | 0 |
| | STDEV | 0.00 | 0.00 | 0.02 | 0.07 | 0 |
| D3609-163D(negative) | average | 0.00 | 0.00 | 0.01 | 1.80 | 0 |
| | STDEV | 0.00 | 0.00 | 0.02 | 0.15 | 0 |
| D3598- wild type Ch FATB2 | average | 1.52 | 6.55 | 0.19 | 1.60 | 8.07 |
| | STDEV | 0.19 | 0.62 | 0.02 | 0.11 | 0.81 |
| D3599- H163Y, L186P(positive) | average | 5.77 | 12.50 | 0.39 | 1.73 | 18.27 |
| | STDEV | 0.63 | 0.99 | 0.03 | 0.05 | 1.62 |

*12 transformants were screened per mutant. The length of lipid production unde low lintrogen conditions was 3 days.

In summary, we have shown that it is possible to increase activity and shift profile specificity within C8-C10 specific FATB thioesterases derived from *Cuphea hookeriana* by using site directed mutagenesis of H163 and L186 within the N-terminal specificity domain. We found cells expressing variants that exceeded the parent ChFATB2 sequence in terms of sum of C8:0+C10:0 production including strains that produced oils with fatty acid profiles where the C8 and C10 production exceed 9, 11, 14, of the profile.

Example 2

Identification of Double Mutants in FATB

Based on the demonstrated ability to modify the activity and specificity of a FATB2 thioesterase originally isolated from *Cuphea hookeriana* (Ch FATB2, accession U39834), using site directed mutagenesis of H163 and L186 a second round of mutagenesis was initiated. Six constructs combining the positive mutations from Rd1 (C8+C10 within 3 standard deviations above the wild-type Ch FATB2 control (D3598)) were generated (Table 2).

TABLE 2

| | Beneficial Mutations Constructs | |
|---|---|---|
| 1) | 163Tyr | 186Lys |
| 2) | 163Tyr | 186Ala |
| 3) | 163Phe | 186Pro |

TABLE 2-continued

Beneficial Mutations Constructs

| | | |
|---|---|---|
| 4) | 163Phe | 186Lys |
| 5) | 163Phe | 186Ala |

For the above examples, an expression construct was used that targeted the FATB variants and selection markers to the Thi4 (thiamine biosynthesis) locus. An antibiotic resistance gene was used to select for resistance to G418 antibiotic. The UAPA promoter was used to drive FATB. The construct is exemplified in SEQ ID NO: 9.

Five individual Ch FATB2 variants were generated and their effect on C8:0 and C10:0 fatty acid accumulation was quantified. Transformants with C8-C10 sum within 3 standard deviations above the wild-type Ch FATB2 control (D3598) were classified as positive (Table 3) and those within 3 standard deviations below were scored as negative (Table 3). The remaining transformants were classified as neutral. As shown in Table 3, *Prototheca moriformis* transformed with three of the Ch FATB2 mutants (D3875, D3876, and D3885) accumulated C8:0-C10:0 fatty acids within 3 standard above transformants expressing the wild type Ch FATB2 (D3598) control.

TABLE 3

| Ch FABT2 variant | | C8:0 | C10:0 | C12:0 | C14:0 | C8-C10sum |
|---|---|---|---|---|---|---|
| D3875-163F, 186A | average | 4.66 | 12.40 | 0.34 | 1.61 | 19.02 |
| (positive) | STDEV | 1.27 | 2.39 | 0.05 | 0.19 | 3.73 |
| D3876-163F,186K | average | 5.25 | 13.12 | 0.36 | 1.55 | 20.28 |
| (positive) | STDEV | 1.19 | 2.05 | 0.05 | 0.03 | 3.31 |
| D3877-163F, 186P | average | 0.00 | 0.00 | 0.00 | 1.90 | 1.90 |
| (negative) | STDEV | 0.00 | 0.00 | 0.00 | 0.28 | 0.28 |
| D3884-163Y, 186A | average | 4.29 | 11.69 | 0.32 | 1.52 | 17.81 |
| | STDEV | 0.58 | 1.06 | 0.03 | 0.04 | 1.69 |
| D3885-163Y, 186K | average | 5.39 | 13.14 | 0.36 | 1.49 | 20.38 |
| (positive) | STDEV | 1.31 | 2.18 | 0.05 | 0.03 | 3.52 |
| D3598- wild type | average | 1.14 | 5.72 | 0.15 | 1.56 | 8.57 |
| Ch FATB2 | STDEV | 0.27 | 0.77 | 0.06 | 0.05 | 1.12 |
| D3599- H163Y, | average | 5.65 | 12.91 | 0.39 | 1.74 | 20.69 |
| L186P | STDEV | 1.29 | 2.06 | 0.06 | 0.02 | 3.42 |

Example 3

Mutations at FATB Position 230

In the example below, we demonstrate the ability to modify the activity and specificity of three FATB thioesterases originally isolated from Cuphea hookeriana (Ch FATB2, Uniprot accession U39834), Cuphea palustris (Cpal FATB1, Uniprot accession Q39554, SEQ ID NO: 13) and *Cuphea avigera* FATB1 (Ca FATB1 accession R4J2L6, SEQ ID NO: 14) using site directed mutagenesis of a conserved Met within the enzymatic core (M230 within Cpal FATB1).

It has recently been reported that substitution of the conserved M230 within the Cpal FATB1 with Iso, Val, Phe or Leu will increase the enzymatic activity of this thioesterase. Because these results were obtained using *E. coli*, we performed a similar screen to see if the results could be reproduced when expressed in *Prototheca moriformis* microalgae. The wild-type and thirteen Cpal FATB1 M230 mutants were generated and their effect on C8:0 fatty acid accumulation quantified. As shown in Table 4, *Prototheca moriformis* transformed with six of the Cpal FATB1 M230 mutants (D3206, D3208, D3211, D3212, D3214, and D3215) exhibited fatty acid profiles that were similar to the non-transformed S6165 host algal strain which likely is due to the mutation inactivating the Cpal FATB1 enzyme. In contrast, *Prototheca moriformis* transfomants expressing one of the remaining seven Cpal FATB1 M230 mutants accumulated C8:0 fatty acids to varying degrees above the non-transformed S6165 host. D3213 (M230P) was less effective than the wild-type Cpal FATB1 transformants (D3004), while D3207 (M230L) exhibited the same C8:0 fatty acid levels as the wild-type Cpal FATB1. D3210 (M230A), D3216 (M230T), and D3217 (M230F) all accumulated ≠1-1.5% more C8:0 than the wild-type D3004. Finally, D3132 (M230I) and D3209 (M230V) exhibited a 4 fold increase in C8:0 levels compared to the D3004 wild-type. While these results share some similarity with the published data derived from expression in *E. coli*, there are some notable exceptions. For example, unlike in *E. coli*, substitution of M230 with Leu did not improve C8:0 fatty acid accumulation compared to the wild-type Cpal FATB1. In addition, replacing the M230 with an Ala or Thr increased C8:0 accumulation relative to the wild-type Cpal FATB1, which was not expected based on the *E. coli* based screen.

TABLE 4

Impact on fatty acid profiles upon expression of the wild-type Cpal FATB1 or the indicated mutant within the *P. moriformis* algal strain S6165.

| Transformant | | C8:0 | C10:0 | C12:0 | C14:0 |
|---|---|---|---|---|---|
| Wild-type Cpal FATB1 - | average | 3.67 | 0.52 | 0.21 | 1.43 |
| D3004 | median | 2.98 | 0.44 | 0.19 | 1.45 |
| M230I - D3132 | average | 13.04 | 1.66 | 0.40 | 1.13 |
| | median | 12.13 | 1.53 | 0.37 | 1.15 |
| M230K - D3206 | average | 0.01 | 0.01 | 0.06 | 1.46 |
| | median | 0.00 | 0.00 | 0.06 | 1.45 |
| M230L - D3207 | average | 3.32 | 0.44 | 0.55 | 1.54 |
| | median | 3.45 | 0.44 | 0.56 | 1.53 |
| M230G - D3208 | average | 0.05 | 0.01 | 0.07 | 1.58 |
| | median | 0.07 | 0.00 | 0.07 | 1.58 |
| M230V - D3209 | average | 14.13 | 1.96 | 0.81 | 1.36 |
| | median | 14.31 | 1.97 | 0.80 | 1.36 |
| M230A - D3210 | average | 4.06 | 0.35 | 0.47 | 1.82 |
| | median | 3.92 | 0.34 | 0.45 | 1.80 |
| M230R - D3211 | average | 0.00 | 0.02 | 0.06 | 1.43 |
| | median | 0.00 | 0.00 | 0.06 | 1.44 |
| M230H - D3212 | average | 0.00 | 0.05 | 0.10 | 1.49 |
| | median | 0.00 | 0.05 | 0.09 | 1.47 |
| M230P - D3213 | average | 1.78 | 0.54 | 1.24 | 2.85 |
| | median | 1.65 | 0.52 | 1.20 | 2.77 |

TABLE 4-continued

Impact on fatty acid profiles upon expression of
the wild-type Cpal FATB1 or the indicated mutant within
the *P. moriformis* algal strain S6165.

| Transformant | | C8:0 | C10:0 | C12:0 | C14:0 |
|---|---|---|---|---|---|
| M230D - D3214 | average | 0.00 | 0.03 | 0.05 | 1.50 |
| | median | 0.00 | 0.03 | 0.05 | 1.50 |
| M230E - D3215 | average | 0.00 | 0.00 | 0.05 | 1.49 |
| | median | 0.00 | 0.00 | 0.05 | 1.46 |
| M230T - D3216 | average | 5.83 | 0.57 | 0.39 | 1.48 |
| | median | 5.77 | 0.57 | 0.40 | 1.52 |
| M230F - D3217 | average | 5.75 | 0.97 | 0.93 | 1.78 |
| | median | 5.24 | 0.91 | 0.89 | 1.77 |
| S6165 parent | | 0 | 0 | 0 | 1.50 |

Data shown is the average and median of 12-24 individual transformants for each Cpal FATB1 expression construct.

Due to the discrepancies in outcome between the *E. coli* and *P. moriformis* expression, we explored the consequence of generating mutants at the parallel position within C8-C10 specific FATB thioesterases derived from *C. hookeriana* (Ch FATB2) and *C. avigera* (Ca FATB1). FIG. 2 shows the results of replacing the Met with Iso in the Ch FATB2 (D3455, M228I) and Lys with Met or Iso in the Ca FATB1 (D3458 and D3459, respectively). Interestingly, the transformants expressing the Ch FATB2 M228I (D3455) mutant exhibit ~50% lower total C8:0-C14:0 fatty acids compared to wild-type Ch FATB2 (D3042) expression. Transformants expressing the K228M Ca FATB1 (D3458) produced ~1.5 fold greater C8:0-C14:0 fatty acid level compared to the wild-type Ca FATB1 (D3456), while the K228I Ca FATB1 (D3459) was slightly less effective than wild-type Ca FATB1 expression. Importantly, both K228M and K228I Ca FATB1 mutants exhibited a novel fatty acid preference. Both Ca FATB1 mutants accumulated a lower percent of C8:0 relative to the total C8:0-C14:0 compared to the wild-type Ca FATB1. In addition, transformants expressing the K228I Ca FATB1 mutant (D3459) produced C12:0 and C14:0 fatty acids which was not observed with the wild-type or K228M Ca FATB1.

In summary, we have shown that the conclusions drawn from the *e coli* expression screen only partially agrees with our data derived from expressing the Cpal FATB1 mutants in our *P. moriformis* platform. In addition, the phenotypes observed upon substitution of the same amino acid position within the Ch FATB2 and Ca FATB1 are not what would have been expected based on the original *e coli* expression screen. Our results demonstrate that the expression platform and the thioesterase influence the outcome of a mutagenesis study.

Example 4

In addition to the results shown in Table 3 we discovered that *Prototheca moriformis* transfomants expressing Ch FATB2 H163Y, L186P, and 230K (D3599) mutants exhibited a shift in fatty acid profile specificity relative to the best Ch FATB2 mutant (D3599). Therefore an additional set of mutants were generated to alter the activity and specificity of Ch FATB2, Table 5. The 228K mutation corresponds to position 230 of Cuphea palustris FATB1 (SEQ ID NO: 13). Residue 230 of *Cuphea palustris* FATB1 corresponds to M228 in the Cuphea hookeriana FATB2 and *Cuphea avigera* FATB1.

TABLE 5

Beneficial Mutations Constructs

| 1) | 163Tyr | 186Pro | 228Lys |
| 2) | 163Tyr | 186Lys | 228Lys |
| 3) | 163Tyr | 186Ala | 228Lys |
| 4) | 163Phe | 186Pro | 228Lys |
| 5) | 163Phe | 186Lys | 228Lys |
| 6) | 163Phe | 186Ala | 228Lys |

Five individual Ch FATB2 variants were generated and their effect on C8:0 and C10:0 fatty acid accumulation was quantified.

TABLE 6

| Ch FABT2 variant | | C8:0 | C10:0 | C12:0 | C14:0 | C8-C10sum |
|---|---|---|---|---|---|---|
| D3886-163F, | average | 3.72 | 2.33 | 0.20 | 1.80 | 8.05 |
| 186A, 228K | STDEV | 1.06 | 0.46 | 0.03 | 0.10 | 1.64 |
| D3887-163F, | average | 5.16 | 2.97 | 0.25 | 1.88 | 10.25 |
| 186K, 228K | STDEV | 1.34 | 0.61 | 0.04 | 0.12 | 2.11 |
| D3888-163F, | average | 4.57 | 2.72 | 0.18 | 1.85 | 9.32 |
| 186P, 228K | STDEV | 1.42 | 0.71 | 0.06 | 0.07 | 2.24 |
| D3895-163Y, | average | 4.17 | 2.51 | 0.20 | 1.84 | 8.71 |
| 186A, 228K | STDEV | 1.72 | 0.93 | 0.07 | 0.10 | 2.80 |
| D3896-163Y, | average | 4.35 | 2.70 | 0.22 | 1.80 | 9.06 |
| 186K, 228K | STDEV | 0.73 | 0.28 | 0.02 | 0.07 | 1.08 |
| D3598- wild type | average | 1.14 | 5.72 | 0.15 | 1.56 | 8.57 |
| Ch FATB2 | STDEV | 0.27 | 0.77 | 0.06 | 0.05 | 1.12 |
| D3519- H163Y, | average | 6.27 | 3.57 | 0.22 | 1.89 | 11.94 |
| L186P, 228K | STDEV | 2.10 | 0.86 | 0.05 | 0.08 | 3.07 |

Example 5

In the example below, we demonstrate the ability to modify the activity and specificity of a FATA thioesterase originally isolated from Garcinia mangostana (GmFATA, accession 004792), using site directed mutagenesis targeting six amino acid positions within the enzyme. The rational for targeting three of the amino acids (G108, S111, V193) was based on research published by Facciotti, et al., Nat Biotechnol. (1999) 17(6):593-7. The remaining three amino acids (L91, G96, T156) were targeted based on research performed at Solazyme with other thioesterases.

To test the impact of each mutation on the activity of the GmFATA, the wild-type and mutant genes were cloned into a vector enabling expression within the *P. moriformis* strain 53150. Table 7 summarizes the results from a three day lipid profile screen comparing the wild-type GmFATA with the 14 mutants. Three GmFATA mutants (D3998, D4000, D4003) increased the amount of C18:0 by at least 1.5 fold compared to the wild-type protein (D3997). D3998 and D4003 were mutations that had been described by Facciotti et al (Nat-Biotech 1999) as substitutions that increased the activity of the GmFATA. In contrast, the D4000 mutation was based on research at Solazyme which demonstrated this position influenced the activity of the FATB thioesterases.

PAT2) and the above-mentioned combinations of GarmFATA1 site-directed mutants to the FATA-1 locus. TcLPAT2 is highly specific for incorporation of unsaturated fatty acids at the sn-2 position of TAGs. The S5780 strain, containing a deletion of a stearoyl ACP desaturase (SAD) allele, was made according to the teachings in co-owned

TABLE 7

| Algal Strain | DNA # | SEQ ID NO: | GmFATA | C14:0 | C16:0 | C18:0 | C18:1 | C18:2 |
|---|---|---|---|---|---|---|---|---|
| *P. moriformis* | — | — | — | 1.63 | 29.82 | 3.08 | 55.95 | 7.22 |
| S3150 | D3997 | 15 | Wild-Type GmFATA | 1.79 | 29.28 | 7.32 | 52.88 | 6.21 |
| | D3998 | 16 | S111A, V193A | 1.84 | 28.88 | 11.19 | 49.08 | 6.21 |
| | D3999 | 17 | S111V, V193A | 1.73 | 29.92 | 3.23 | 56.48 | 6.46 |
| | D4000 | 18 | G96A | 1.76 | 30.19 | 12.66 | 45.99 | 6.01 |
| | D4001 | 19 | G96T | 1.82 | 30.60 | 3.58 | 55.50 | 6.28 |
| | D4002 | 20 | G96V | 1.78 | 29.35 | 3.45 | 56.77 | 6.43 |
| | D4003 | 21 | G108A | 1.77 | 29.06 | 12.31 | 47.86 | 6.08 |
| | D4007 | 25 | G108V | 1.81 | 28.78 | 5.71 | 55.05 | 6.26 |
| | D4004 | 22 | L91F | 1.76 | 29.60 | 6.97 | 53.04 | 6.13 |
| | D4005 | 23 | L91K | 1.87 | 28.89 | 4.38 | 56.24 | 6.35 |
| | D4006 | 24 | L91S | 1.85 | 28.06 | 4.81 | 56.45 | 6.47 |
| | D4008 | 26 | T156F | 1.81 | 28.71 | 3.65 | 57.35 | 6.31 |
| | D4009 | 27 | T156A | 1.72 | 29.66 | 5.44 | 54.54 | 6.26 |
| | D4010 | 28 | T156K | 1.73 | 29.95 | 3.17 | 56.86 | 6.21 |
| | D4011 | 29 | T156V | 1.80 | 29.17 | 4.97 | 55.44 | 6.27 |

Example 6

Wild-type *P. moriformis* storage lipid is comprised of ~60% oleic (C18:1), ~25-30% palmitic (C16:0), and ~5-8% linoleic (C18:2) acids, with minor amounts of stearic (C18:0), myristic (C14:0), α-linolenic (C18:3α), and palmitoleic (C16:1) acids. This fatty acid profile results from the relative activities and substrate affinities of the enzymes of the endogeneous fatty acid biosynthetic pathway. The introduction of Garcinia mangostana FATA thioesterase (GarmFATA1) gene into *P. moriformis* results in oils with increased levels of stearate (C18:0). Furthermore we demonstrated that the G96A and G108A single mutations, and the (S111A, V193A) double mutations in GarmFATA1 increased C18:0 accummulation relative to the native GarmFATA1 protein.

In the present example we assessed the thioesterase activity of a series of additional GarmFATA1 mutants. These mutants were generated by combining the above-described G96A, G108A, S111A and V193A mutations into double, triple or quadruple mutants. Specifically we tested GarmFATA1 (G96A, G108A), GarmFATA1 (G96A, S111A), GarmFATA1 (G96A, V193A), GarmFATA1 (G108A, S111A), GarmFATA1 (G108A, V193A), GarmFATA1 (G96A, G108A, S111A), GarmFATA1 (G96A, G108A, V193A), GarmFATA1 (G96A, S111A, V193A), GarmFATA1 (G108A, S111A, V193A), and GarmFATA1 (G96A, G108A, S111A, V193A) mutant combinations. GarmFATA1 (G108A) was used as a control since out of all the mutants tested earlier this one gave the best increase in C18:0 levels over the native GARMFATA1 protein. The screen was carried out in S5780, a strain previously constructed in S5100 —a high oleic base strain. S5780 was created through the targeted deletion of the dominant SAD2-1 allele, reducing the rate of conversion of C18:0 to C18:1 and overexpression of PmKASII, increasing elongation of C16:0 to C18:0. S5780 was transformed with constructs that targeted the LPAT2 gene from *T. cacao* (TcLapplications WO2010/063031, WO2011/150411, and/or WO2012/106560, all of which are herein incorporated by reference.

Construct used for the Expression of TcLPAT2 and GarmFATA1 (G96A, G108A) at PmFATA1 locus—(pSZ5990)

In this example 55780 strain, transformed with the construct pSZ5990, was generated which express *Saccharomyces carlbergenesis* SUC2 gene (allowing for their selection and growth on medium containing sucrose), a *T. cacao* LPAT2 and *G. mangostana* FATA1 (G96A, G108A) thioesterase targeted at endogenous PmFATA1 genomic region. Construct pSZ5990 introduced for expression in S5780 can be written as FATA-1 3' flank::CrTub2-ScSUC2-PmPGH: Spacer1:PmG3PDH-1-TcLPAT2-PmATP:Spacer2:Pm-SAD2-2v2-CpSAD1tp_GarmFATA1(G96A, G108A)_FLAG-PmSAD2-1::FATA-1 5' flank The sequence of the transforming DNA is provided in FIG. 1. Relevant restriction sites in the construct are indicated in lowercase, underlined bold, and are from 5'-3' BspQI, KpnI, XbaI, MfeI, BamHI, AvrII, NdeI, NsiI, AflII, EcoRI, SpeI, AscII, ClaI, SacI and BspQI respectively. BspQI sites delimit the 5' and 3' ends of the transforming DNA. Bold, lowercase sequences represent genomic DNA from *P. moriformis* that permit targeted integration at the FATA1 locus via homologous recombination. Proceeding in the 5' to 3' direction, the *Chlorella reinhardtii* Tubulin 2, driving the expression of the *S. cervisiae* SUC2 gene is indicated by lowercase, boxed text. Uppercase italics indicate the initiator ATG and terminator TGA for SUC2, while the coding region is indicated with lowercase italics. The *P. moriformis* Phosphoglycerate dehydratase (PGH) gene 3' UTR is indicated by lowercase underlined text followed by buffer/spacer-1 DNA sequence indicated by lowercase bold italic text. Immediately following the buffer nucleotide is an endogenous G3PDH-1 promoter of *P. moriformis*, indicated by boxed lowercase text. Uppercase italics indicate the Initiator ATG and terminator TGA codons of the T cacao LPAT2 gene, while the lowercase italics indicate the remainder of the gene. The *P. moriformis* Adenosine triphosphate (ATP) gene 3' UTR is indicated by lowercase underlined text followed by the buffer/spacer 2 nucleotide sequence indicated by lowercase bold italic text. Immediately following the spacer-2 sequence is the endogenous PmSAD2-2 promoter of *P. moriformis*, indicated by boxed lowercase text. Uppercase italics indicate the initiator ATG and terminator TGA for G. mangostana FATA1 gene while the coding region is indicated with lowercase italics. The FATA1 gene is translationally fused to *C. protothecoides* Stearoyl ACP Desaturase-1 (CpSAD1) transit peptide at the N terminal (indicated by underlined lowercase italic text) for proper targeting to chloroplast and the 3XFLAG tag at the C terminal (indicated double underlined, italic, bold lowercase text). GarmFATA1 with CpSAD transit peptide and 3XFLAG sequence is followed by endogenous Stearoyl ACP Desaturase-1 (SAD1) gene 3' UTR indicated by lowercase underlined text. The genomic sequence of endogenous FATA1 gene is indicated by lowercase bold text. The final construct was sequenced to ensure correct reading frames and targeting sequences, and is provided as SEQ ID NO:46.

In addition to *T cacao* LPAT2 and *G. mangostana* FATA1 (G96A, G108A) genes targeted at PmFAFA1 locus (pSZ5990) several other constructs incorporating the various mutations described above were designed for transformation into S5780. These constructs are summarized below in Table 8:

In addition, the constructs pSZ6019 t0 pSZ6023, pSZ6026 and pSZ6028 differ in promoter driving the particular GarmFATA1 mutant. While in pSZ5990 GarmFATA1 (G96A, G108A) is driven by PmSAD2-2v2 promoter, the various GarmFATA1 mutant combinations in pSZ6019-pSZ6028 are driven by PmACP-P1 promoter. The nucleotide sequences of various GarmFATA1 mutants used in the above constructs are shown in SEQ ID NOS: 47-56. The promoter sequence of PmACP-P1 is pSZ6019-pSZ6028 is shown in SEQ ID NO: 57. Relevant restriction sites as bold text are shown 5'-3' respectively.

To determine their impact on fatty acid profiles, all the constructs described above were transformed independently into either S5780. Primary transformants were clonally purified and grown under standard lipid production conditions at pH5.0. The resulting profiles from a set of representative clones arising from transformation of S5780 with pSZ5936 (D4933), pSZ5990 (D4950), pSZ5991 (D4951), pSZ5986 (D4948), pSZ5982 (4931), pSZ5983 (D4932), pSZ6005 (D4952), pSZ5984 (D4933), pSZ6004 (D4953), pSZ5985 (D4934), pSZ5987 (D4949), pSZ6018 (D4978), pSZ6019 (D4979), pSZ6020 (D4980), pSZ6021 (D4981), pSZ6022 (D4982), pSZ6023 (D4983), pSZ6026 (D4986), pSZ6028 (D4988) are shown in Tables 9-19 respectively.

Table 13 lists the average fatty acid profiles and glucose consumption (relative to the S7485 base strain) for each set of transformants. Disruption of one allele of FATA-1 reduces C16:0 by 1-2%, while TcLPAT2 activity manifests as a 1-1.5% increase in C18:2 in these strains. D4993 and D4978

TABLE 8

| Plasmid | SEQ ID NO: | Genotype |
| --- | --- | --- |
| pSZ5936 | 47 | FATA-1::CrTUB2-ScSUC2-PmPGH:PmG3PDH-1-TcLPAT2-PmATP:PmSAD2-2-CpSAD1_GarmFATA1(G108A)_FLAG-PmSAD2-1::FATA-1_5' |
| pSZ5991 | 48 | FATA-1_3'::CrTUB2-ScSUC2-PmPGH:PmG3PDH-1-TcLPAT2-PmATP:PmSAD2-2-CpSAD1_GarmFATA1(G96A, S111A)_FLAG-PmSAD2-1::FATA-1_5' |
| pSZ5986 | 49 | FATA-1_3'::CrTUB2-ScSUC2-PmPGH:PmG3PDH-1-TcLPAT2-PmATP:PmSAD2-2-CpSAD1_GarmFATA1(G96A, V193A)_FLAG-PmSAD2-1::FATA-1_5' |
| pSZ5982 | 50 | FATA-1_3'::CrTUB2-ScSUC2-PmPGH:PmG3PDH-1-TcLPAT2-PmATP:PmSAD2-2-CpSAD1_GarmFATA1(G108A, S111A)_FLAG-PmSAD2-1::FATA-1_5' |
| pSZ5983 | 51 | FATA-1_3'::CrTUB2-ScSUC2-PmPGH:PmG3PDH-1-TcLPAT2-PmATP:PmSAD2-2-CpSAD1_GarmFATA1(G108A, V193A)_FLAG-PmSAD2-1::FATA-1_5' |
| pSZ6005 | 52 | FATA-1_3'::CrTUB2-ScSUC2-PmPGH:PmG3PDH-1-TcLPAT2-PmATP:PmSAD2-2-CpSAD1_GarmFATA1(G96A, G108A, S111A)_FLAG-PmSAD2-1::FATA-1_5' |
| pSZ5984 | 53 | FATA-1_3'::CrTUB2-ScSUC2-PmPGH:PmG3PDH-1-TcLPAT2-PmATP:PmSAD2-2-CpSAD1_GarmFATA1(G96A, G108A, V193A)_FLAG-PmSAD2-1::FATA-1_5' |
| pSZ6004 | 54 | FATA-1_3'::CrTUB2-ScSUC2-PmPGH:PmG3PDH-1-TcLPAT2-PmATP:PmSAD2-2-CpSAD1_GarmFATA1(G96A, S111A, V193A)_FLAG-PmSAD2-1::FATA-1_5' |
| pSZ5985 | 55 | FATA-1_3'::CrTUB2-ScSUC2-PmPGH:PmG3PDH-1-TcLPAT2-PmATP:PmSAD2-2-CpSAD1_GarmFATA1(G108A, S111A, V193A)_FLAG-PmSAD2-1::FATA-1_5' |
| pSZ5987 | 56 | FATA-1_3'::CrTUB2-ScSUC2-PmPGH:PmG3PDH-1-TcLPAT2-PmATP:PmSAD2-2-CpSAD1_GarmFATA1(G96A, G108A, S111A, V193A)_FLAG-PmSAD2-1::FATA-1_5' |
| pSZ6018 | 47 | FATA-1::CrTUB2-ScSUC2-PmPGH:PmG3PDH-1-TcLPAT2-PmATP:PmACPp1p CpSAD1_GarmFATA1(G108A)_FLAG-PmSAD2-1::FATA-1_5' |
| pSZ6019 | 50 | FATA-1::CrTub2-ScSUC2-PmPGH:PmG3PDH-1-TcLPAT2-PmATP:PmACP-P1p-CpSAD1tp_GarmFATA1(G108A, S111A)_FLAG-PmSAD2-1:FATA-1 |
| pSZ6020 | 51 | FATA-1::CrTub2-ScSUC2-PmPGH:PmG3PDH-1-TcLPAT2-PmATP:PmACP-P1p-CpSAD1tp_GarmFATA1(G108A, V193A)_FLAG-PmSAD2-1::FATA-1 |
| pSZ6021 | 53 | FATA-1::CrTub2-ScSUC2-PmPGH:PmG3PDH-1-TcLPAT2-PmATP:PmACP-P1p-CpSAD1tp_GarmFATA1(G96A, G108A, V193A)_FLAG-PmSAD2-1::FATA-1 |
| pSZ6022 | 55 | FATA-1::CrTub2-ScSUC2-PmPGH:PmG3PDH-1-TcLPAT2-PmATP:PmACP-P1p-CpSAD1tp_GarmFATA1(G108, S111A, V193A)_FLAG-PmSAD2-1::FATA-1 |
| pSZ6023 | 49 | FATA-1::CrTub2-ScSUC2-PmPGH:PmG3PDH-1-TcLPAT2-PmATP:PmACP-P1p-CpSAD1tp_GarmFATA1(G96A, V193A)_FLAG-PmSAD2-1::FATA-1 |
| pSZ6026 | 48 | FATA-1::CrTub2-ScSUC2-PmPGH:PmG3PDH-1-TcLPAT2-PmATP:PmACP-P1p-CpSAD1tp_GarmFATA1(G96A, S111A)_FLAG-PmSAD2-1:FATA-1 |
| pSZ6028 | 52 | FATA-1::CrTub2-ScSUC2-PmPGH:PmG3PDH-1-TcLPAT2-PmATP:PmACP-P1p-CpSAD1tp_GarmFATA1(G96A G108A, S111A)_FLAG-PmSAD2-1::FATA-1 |

All these constructs have the same vector backbone, selectable marker, promoters, genes and 3' UTRs as pSZ5990 differing only in the mutations in the GarmFATA1.

expressing GarmFATA1 (G108A) mutant accumulated between 44.69% to 45.33% and 34.26 to 50.94% C18:0 respectively. D4993 has GarmFATA1 (G108A) driven by PmSAD2-2 promoter while for D4978 PmACP-P1 promoter drives the GarmFATA1 (G108A). Strains with the (G96A, G108A), (G108A, S111A) and (G108A, V193A) combinations consistently accumulated more C18:0 than the (G108A) single mutant, with minimal increases in C16:0. D4950 (G96A, G108A) produced more than 50% C18:0 in multiple strains. The (G96A, G108A, S111A), (G96A, G108A, V193A) and (G96A, S111A, V193A) triple mutants also produced generally higher C18:0, but at a cost of increased C16:0. The (G108A, S111A, V193A) triple mutant and (G96A, G108A, S111A, V193A) quadruple mutant produced C18:0 less than the G108 single mutant. PmACP-P1 promoter generally resulted in more C18:0 than the ones driven by PmSAD2-2 promoter.

TABLE 9

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780 | 0.75 | 7.07 | 30.32 | 51.61 | 5.96 | 0.79 | 2.16 |
| S5780; T1402; D4993-7 | 0.65 | 4.66 | 45.33 | 38.86 | 7.42 | 0.64 | 1.50 |
| S5780; T1402; D4993-4 | 0.66 | 4.62 | 45.22 | 38.64 | 7.70 | 0.67 | 1.51 |
| S5780; T1402; D4993-2 | 0.63 | 4.54 | 44.94 | 39.11 | 7.59 | 0.66 | 1.54 |
| S5780; T1402; D4993-8 | 0.65 | 4.52 | 44.92 | 39.22 | 7.62 | 0.65 | 1.50 |
| S5780; T1402; D4993-9 | 0.64 | 4.60 | 44.69 | 39.45 | 7.52 | 0.64 | 1.48 |
| S5780; T1395; D4978-1 | 0.72 | 5.22 | 50.94 | 32.58 | 7.49 | 0.67 | 1.43 |
| S5780; T1395; D4978-6 | 0.68 | 5.15 | 49.26 | 34.74 | 7.17 | 0.65 | 1.45 |
| S5780; T1395; D4978-2 | 0.78 | 6.21 | 43.12 | 39.62 | 7.01 | 0.72 | 1.57 |
| S5780; T1395; D4978-3 | 0.79 | 6.90 | 34.26 | 48.01 | 6.41 | 0.79 | 1.91 |

Table 9 provides primary 3-day Fatty acid profiles of representative 55780 strains transformed with D4993 (pSZ5936) and D4978 (pSZ6018). Both pSZ5936 and pSZ6018 have GarmFATA1 (G108) mutant driven by PmSAD2-2 or PmACP-P1 respectively.

TABLE 10

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780 | 0.70 | 6.98 | 30.82 | 51.28 | 5.80 | 0.77 | 2.27 |
| S5780; T1402; D4950-3 | 0.64 | 5.16 | 50.73 | 32.92 | 7.34 | 0.62 | 1.41 |
| S5780; T1402; D4950-8 | 0.64 | 5.17 | 50.63 | 33.10 | 7.28 | 0.62 | 1.41 |
| S5780; T1402; D4950-5 | 0.66 | 5.20 | 50.23 | 33.31 | 7.42 | 0.62 | 1.40 |
| S5780; T1402; D4950-7 | 0.65 | 5.15 | 49.90 | 33.81 | 7.31 | 0.63 | 1.40 |
| S5780; T1402; D4950-4 | 0.66 | 5.22 | 49.53 | 34.13 | 7.21 | 0.61 | 1.42 |

Table 10 provides primary 3-day Fatty acid profiles of representative S5780 strains transformed with D4950 (pSZ5990). pSZ5990 expresses GarmFATA1 (G96A, G108) mutant driven by PmSAD2-2.

TABLE 11

| Sample ID | Fatty acid profile | | | | | | |
|---|---|---|---|---|---|---|---|
| | C14:0 | C16:0 | C18:0 | C18:1 | C18:2 | C18:3 α | C20:0 |
| S5780 | 0.81 | 7.56 | 31.15 | 50.19 | 6.12 | 0.82 | 2.18 |
| S5780; T1402; D4951-18 | 0.73 | 5.11 | 46.22 | 36.56 | 7.92 | 0.72 | 1.54 |
| S5780; T1402; D4951-8 | 0.70 | 4.80 | 42.65 | 40.59 | 7.77 | 0.72 | 1.58 |
| S5780; T1402; D4951-3 | 0.70 | 4.82 | 42.42 | 40.74 | 7.76 | 0.71 | 1.58 |
| S5780; T1402; D4951-4 | 0.69 | 4.82 | 42.28 | 40.88 | 7.76 | 0.73 | 1.60 |
| S5780; T1402; D4951-15 | 0.72 | 4.95 | 42.07 | 40.72 | 8.00 | 0.73 | 1.58 |
| S5780; T1395; D4986-21 | 0.79 | 5.78 | 48.77 | 33.99 | 7.54 | 0.69 | 1.48 |
| S5780; T1395; D4986-18 | 0.77 | 5.77 | 48.43 | 34.61 | 7.32 | 0.65 | 1.46 |
| S5780; T1395; D4986-23 | 0.78 | 5.66 | 47.64 | 35.30 | 7.44 | 0.69 | 1.49 |
| S5780; T1395; D4986-15 | 0.75 | 5.52 | 47.60 | 35.80 | 7.21 | 0.67 | 1.50 |
| S5780; T1395; D4986-1 | 0.84 | 6.38 | 46.95 | 34.55 | 8.29 | 0.64 | 1.33 |

Table 11 provides Primary 3-day Fatty acid profiles of representative S5780 strains transformed with D4951 (pSZ5991) and D4986 (pSZ6026). pSZ5991 and pSZ6026 express GarmFATA1 (G96A, S111A) mutant driven by PmSAD2-2 and PmACP-P1 respectively.

TABLE 12

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780 | 0.82 | 7.51 | 30.86 | 50.34 | 6.27 | 0.86 | 2.16 |
| S5780; T1388; D4948-6 | 0.70 | 4.93 | 46.65 | 36.92 | 7.66 | 0.68 | 1.50 |
| S5780; T1388; D4948-10 | 0.66 | 4.79 | 46.23 | 37.72 | 7.51 | 0.68 | 1.43 |
| S5780; T1388; D4948-11 | 0.72 | 5.05 | 46.18 | 36.89 | 8.04 | 0.67 | 1.47 |
| S5780; T1388; D4948-4 | 0.72 | 5.11 | 46.11 | 36.97 | 8.00 | 0.66 | 1.45 |
| S5780; T1388; D4948-9 | 0.72 | 5.06 | 46.09 | 36.96 | 8.05 | 0.67 | 1.45 |
| S5780; T1395; D4983-25 | 0.73 | 5.85 | 49.47 | 32.96 | 7.77 | 0.62 | 1.49 |
| S5780; T1395; D4983-14 | 0.68 | 5.25 | 48.53 | 35.02 | 7.32 | 0.63 | 1.52 |
| S5780; T1395; D4983-27 | 0.70 | 5.66 | 48.35 | 34.56 | 7.56 | 0.62 | 1.50 |
| S5780; T1395; D4983-18 | 0.67 | 5.30 | 48.26 | 35.35 | 7.29 | 0.62 | 1.51 |
| S5780; T1395; D4983-13 | 0.68 | 5.31 | 48.09 | 35.59 | 7.27 | 0.63 | 1.48 |

Table 12 provides primary 3-day Fatty acid profiles of representative S5780 strains transformed with D4948 (pSZ5986) and D4983 (pSZ6023). pSZ5986 and pSZ6023 express GarmFATA1 (G96A, V193A) mutant driven by PmSAD2-2 and PmACP-P1 respectively.

TABLE 13

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780 | 0.77 | 7.36 | 30.84 | 50.71 | 6.24 | 0.87 | 2.12 |
| S5780; T1388; D4931-25 | 0.70 | 5.13 | 48.48 | 35.40 | 7.25 | 0.64 | 1.43 |
| S5780; T1388; D4931-9 | 0.73 | 5.43 | 48.29 | 34.92 | 7.63 | 0.65 | 1.41 |
| S5780; T1388; D4931-13 | 0.72 | 5.24 | 48.13 | 35.22 | 7.64 | 0.66 | 1.45 |
| S5780; T1388; D4931-17 | 0.76 | 5.14 | 48.07 | 35.08 | 7.86 | 0.68 | 1.42 |
| S5780; T1388; D4931-12 | 0.73 | 5.33 | 47.91 | 35.27 | 7.65 | 0.67 | 1.42 |
| S5780; T1395; D4979-36 | 0.89 | 6.91 | 50.03 | 31.13 | 7.83 | 0.67 | 1.40 |
| S5780; T1395; D4979-5 | 0.77 | 5.88 | 49.65 | 33.24 | 7.25 | 0.68 | 1.48 |
| S5780; T1395; D4979-41 | 0.79 | 6.25 | 49.52 | 33.09 | 7.28 | 0.63 | 1.42 |
| S5780; T1395; D4979-39 | 0.82 | 6.36 | 49.43 | 32.49 | 7.66 | 0.66 | 1.48 |
| S5780; T1395; D4979-32 | 0.82 | 6.49 | 49.12 | 32.98 | 7.45 | 0.63 | 1.43 |

Table 13 provides primary 3-day Fatty acid profiles of representative S5780 strains transformed with D4931 (pSZ5982) and D4979 (pSZ6019). pSZ5982 and pSZ6019 express GarmFATA1 (G108A, S111A) mutant driven by PmSAD2-2 and PmACP-P1 respectively.

TABLE 14

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780 | 0.79 | 7.46 | 31.60 | 49.57 | 6.28 | 0.86 | 2.19 |
| S5780; T1388; D4932-48 | 0.78 | 4.59 | 49.48 | 31.74 | 9.13 | 1.30 | 1.84 |
| S5780; T1388; D4932-36 | 0.66 | 4.89 | 49.25 | 34.63 | 7.53 | 0.66 | 1.43 |
| S5780; T1388; D4932-28 | 0.66 | 4.93 | 49.04 | 34.91 | 7.50 | 0.65 | 1.38 |
| S5780; T1388; D4932-23 | 0.67 | 4.95 | 49.03 | 34.55 | 7.69 | 0.66 | 1.42 |
| S5780; T1388; D4932-5 | 0.68 | 4.93 | 49.01 | 34.77 | 7.54 | 0.67 | 1.38 |
| S5780; T1395; D4980-21 | 0.71 | 4.54 | 51.48 | 32.09 | 7.54 | 0.87 | 1.78 |
| S5780; T1395; D4980-1 | 0.72 | 5.80 | 48.65 | 33.81 | 8.04 | 0.62 | 1.46 |
| S5780; T1395; D4980-25 | 0.68 | 5.46 | 47.67 | 35.53 | 7.61 | 0.66 | 1.47 |
| S5780; T1395; D4980-18 | 0.77 | 6.49 | 46.51 | 34.39 | 8.69 | 0.71 | 1.45 |
| S5780; T1395; D4980-30 | 0.70 | 5.22 | 45.14 | 38.84 | 6.80 | 0.70 | 1.70 |

Table 14 provides primary 3-day Fatty acid profiles of representative S5780 strains transformed with D4932 (pSZ5983) and D4980 (pSZ6020). pSZ5983 and pSZ6020 express GarmFATA1 (G108A, V193A) mutant driven by PmSAD2-2 and PmACP-P1 respectively.

TABLE 15

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780 | 0.75 | 7.14 | 30.84 | 51.19 | 5.87 | 0.79 | 2.26 |
| S5780; T1402; D4952-9 | 0.77 | 5.68 | 48.96 | 33.44 | 7.70 | 0.68 | 1.50 |
| S5780; T1402; D4952-5 | 0.75 | 5.58 | 48.60 | 33.94 | 7.60 | 0.70 | 1.52 |
| S5780; T1402; D4952-1 | 0.75 | 5.62 | 48.59 | 33.94 | 7.63 | 0.69 | 1.51 |
| S5780; T1402; D4952-8 | 0.78 | 5.78 | 48.51 | 33.71 | 7.74 | 0.67 | 1.50 |
| S5780; T1402; D4952-10 | 0.77 | 5.65 | 48.35 | 34.15 | 7.59 | 0.70 | 1.52 |
| S5780; T1395; D4988-5 | 0.99 | 8.68 | 48.51 | 31.29 | 7.08 | 0.64 | 1.51 |
| S5780; T1395; D4988-7 | 0.75 | 5.50 | 46.63 | 36.68 | 7.41 | 0.69 | 1.43 |
| S5780; T1395; D4988-8 | 0.77 | 5.57 | 46.51 | 36.73 | 7.47 | 0.70 | 1.42 |
| S5780; T1395; D4988-3 | 1.12 | 9.63 | 44.06 | 33.16 | 8.33 | 0.76 | 1.57 |
| S5780; T1395; D4988-10 | 1.27 | 11.45 | 43.35 | 31.26 | 8.95 | 0.74 | 1.49 |

Table 15 provides primary 3-day Fatty acid profiles of representative S5780 strains transformed with D4952 (pSZ6005) and D4988 (pSZ6028). pSZ6005 and pSZ6028 express GarmFATA1 (G96A, G108A, S111A) mutant driven by PmSAD2-2 and PmACP-P1 respectively.

TABLE 16

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780 | 0.79 | 7.46 | 31.60 | 49.57 | 6.28 | 0.86 | 2.19 |
| S5780; T1388; D4933-12 | 0.67 | 5.48 | 50.40 | 32.85 | 7.31 | 0.63 | 1.36 |
| S5780; T1388; D4933-9 | 0.69 | 5.68 | 50.20 | 32.58 | 7.55 | 0.65 | 1.41 |
| S5780; T1388; D4933-8 | 0.66 | 5.46 | 50.07 | 33.20 | 7.35 | 0.63 | 1.39 |
| S5780; T1388; D4933-2 | 0.70 | 5.66 | 49.99 | 32.81 | 7.61 | 0.63 | 1.38 |
| S5780; T1388; D4933-5 | 0.85 | 5.84 | 41.97 | 39.70 | 7.94 | 0.97 | 1.36 |
| S5780; T1395; D4981-1 | 0.63 | 5.07 | 37.33 | 46.45 | 6.75 | 0.76 | 2.00 |
| S5780; T1395; D4981-3 | 0.71 | 5.70 | 34.96 | 47.88 | 7.02 | 0.86 | 1.88 |
| S5780; T1395; D4981-7 | 0.70 | 5.87 | 34.44 | 48.58 | 6.52 | 0.78 | 2.04 |
| S5780; T1395; D4981-4 | 0.75 | 6.18 | 33.78 | 48.83 | 6.61 | 0.83 | 1.98 |
| S5780; T1395; D4981-8 | 0.71 | 6.42 | 33.38 | 49.33 | 6.05 | 0.78 | 2.21 |

Table 16 provides primary 3-day Fatty acid profiles of representative S5780 strains transformed with D4933 (pSZ5984) and D4981 (pSZ6021). pSZ5984 and pSZ6021 express GarmFATA1 (G96A, G108A, V193A) mutant driven by PmSAD2-2 and PmACP-P1 respectively.

TABLE 17

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780 | 0.74 | 7.27 | 31.04 | 50.75 | 5.96 | 0.81 | 2.18 |
| S5780; T1388; D4953-6 | 0.84 | 6.99 | 47.90 | 33.26 | 7.58 | 0.65 | 1.46 |
| S5780; T1388; D4953-4 | 0.85 | 7.09 | 47.54 | 33.64 | 7.46 | 0.66 | 1.42 |
| S5780; T1402; D4953-3 | 0.89 | 6.91 | 47.54 | 33.36 | 7.56 | 0.71 | 1.60 |
| S5780; T1402; D4953-9 | 0.91 | 7.26 | 46.67 | 33.52 | 7.90 | 0.70 | 1.49 |
| S5780; T1402; D4953-1 | 0.90 | 7.20 | 46.37 | 33.86 | 7.91 | 0.72 | 1.54 |

Table 17 provides primary 3-day Fatty acid profiles of representative S5780 strains transformed with D4953 (pSZ6004). pSZ6004 expresses GarmFATA1 (G96A, S111A, V193A) mutant driven by PmSAD2-2.

TABLE 18

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780 | 0.78 | 8.24 | 30.24 | 50.34 | 6.00 | 0.79 | 2.23 |
| S5780; T1402; D4934-20 | 0.84 | 7.10 | 46.71 | 34.60 | 7.34 | 0.65 | 1.47 |

TABLE 18-continued

| Sample ID | Fatty acid profile | | | | | | |
|---|---|---|---|---|---|---|---|
| | C14:0 | C16:0 | C18:0 | C18:1 | C18:2 | C18:3α | C20:0 |
| S5780; T1402; D4934-15 | 0.78 | 6.76 | 44.01 | 38.09 | 6.88 | 0.65 | 1.59 |
| S5780; T1402; D4934-24 | 1.03 | 10.69 | 39.82 | 33.95 | 11.12 | 0.71 | 1.36 |
| S5780; T1402; D4934-14 | 0.77 | 6.83 | 38.68 | 43.31 | 6.51 | 0.71 | 1.88 |
| S5780; T1402; D4934-16 | 0.75 | 6.91 | 35.57 | 46.50 | 6.20 | 0.71 | 1.92 |
| S5780; T1395; D4982-1 | 0.00 | 6.19 | 39.51 | 41.35 | 8.23 | 0.78 | 1.92 |
| S5780; T1395; D4982-2 | 0.03 | 7.02 | 35.52 | 46.24 | 6.59 | 0.81 | 1.89 |

Table 18 provides primary 3-day Fatty acid profiles of representative S5780 strains transformed with D4934 (pSZ5985) and D4982 (pSZ6022). pSZ5985 and pSZ6022 express GarmFATA1 (G108A, S111A, V193A) mutant driven by PmSAD2-2 and PmACP-P1 respectively.

TABLE 19

| Sample ID | Fatty acid profile | | | | | | |
|---|---|---|---|---|---|---|---|
| | C14:0 | C16:0 | C18:0 | C18:1 | C18:2 | C18:3 α | C20:0 |
| S5780 | 0.70 | 6.98 | 30.82 | 51.28 | 5.80 | 0.77 | 2.27 |
| S5780; T1402; D4949-2 | 0.62 | 4.54 | 46.07 | 38.20 | 7.44 | 0.63 | 1.46 |
| S5780; T1402; D4949-13 | 0.66 | 4.57 | 45.33 | 38.42 | 7.85 | 0.68 | 1.50 |
| S5780; T1402; D4949-7 | 0.64 | 4.61 | 45.02 | 39.06 | 7.55 | 0.64 | 1.50 |
| S5780; T1402; D4949-8 | 0.64 | 4.62 | 44.87 | 39.16 | 7.51 | 0.67 | 1.54 |
| S5780; T1402; D4949-3 | 0.64 | 4.88 | 44.18 | 39.83 | 7.18 | 0.65 | 1.56 |

Table 19 provides primary 3-day Fatty acid profiles of representative 55780 strains transformed with D4949 (pSZ5987). pSZ5985 expresses GarmFATA1 (G96A, G108A, S111A, V193A) mutant driven by PmSAD2-2.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A non-natural fatty acyl-ACP thioesterase wherein the non-natural thioesterase has at least 85%, 90%, 91%, 92%, 93%, 94%, 95%, 96%, 97%, 98% or 99% identity to SEQ ID NO: 13 and comprises alanine (A), threonine (T), phenylalanine (F), isoleucine(I), or valine (V) at the position corresponding to position 230 of SEQ ID NO: 13, wherein the non-natural thioesterase catalyzes the production of increased levels of C8:0 and/or C10:0 fatty acids in comparison to a wild-type thioesterase.

2. A non-natural fatty acyl-ACP thioesterase protein of claim 1, wherein the non-natural thioesterase has at least 90% identity to SEQ ID NO:13.

3. A method for increasing the C8 and/or C10 fatty acids in a fatty acid profile of an oil produced by an optionally oleaginous host cell, the method comprising, providing a parent gene encoding a fatty acyl-ACP thioesterase B (FATB) enzyme, mutating the gene to so as to encode a non-natural thioesterase of claim 1.

4. A method for producing a triglyceride oil, the method comprising expressing, in a host cell, the non-natural thioesterase of claim 1.

5. An isolated polynucleotide encoding a non-natural fatty acyl-ACP thioesterase wherein the non-natural thioesterase has at least 85%, 90%, 91%, 92%, 93%, 94%, 95%, 96%, 97%, 98% or 99% identity to SEQ ID NO: 13 and comprises alanine (A), threonine (T), phenylalanine (F), isoleucine(I), or valine (V) at the position corresponding to position 230 of SEQ ID NO: 13, wherein the non-natural thioesterase catalyzes the production of increased levels of C8:0 and/or C10:0 fatty acids in comparison to a wild-type thioesterase.

6. An expression cassette comprising the isolated polynucleotide of claim 5.

7. A host cell comprising the expression cassette of claim 6.

8. The host cell of claim 7, wherein the cell is an oleaginous microalga cell.

9. The host cell of claim 8, wherein the microalga cell is classified as Chlorophyta, Trebouxiophyceae, Chlorellales, Chlorellaceae, or Chlorophyceae.

10. The host cell of claim 9, wherein the microalga cell is of a genus selected from the group consisting of *Chlorella, Dunaliella,* and *Prototheca.*

11. The host cell of claim 10, wherein the microalga cell is of a species selected from the group consisting of *Prototheca moriformis* and Chlorella protothecoides.

12. The non-natural fatty acyl-ACP thioesterase of claim 1, wherein the non-natural thioesterase comprises alanine or threonine at the position corresponding to position 230 of SEQ ID NO: 13.

13. The method of claim 2, wherein the non-natural thioesterase comprises alanine or threonine at the position corresponding to position 230 of SEQ ID NO: 13.

14. The method of claim 2, wherein the non-natural thioesterase comprises alanine or threonine at the position corresponding to position 230 of SEQ ID NO: 13.

15. The method of claim 4, wherein the non-natural thioesterase comprises alanine or threonine at the position corresponding to position 230 of SEQ ID NO: 13.

16. The isolated polynucleotide of claim 5, wherein the non-natural thioesterase comprises alanine or threonine at the position corresponding to position 230 of SEQ ID NO: 13.

17. The host cell of claim 7, wherein the non-natural thioesterase comprises alanine or threonine at the position corresponding to position 230 of SEQ ID NO: 13.

18. The host cell of claim 8, wherein the non-natural thioesterase comprises alanine or threonine at the position corresponding to position 230 of SEQ ID NO: 13.

19. The host cell of claim 10, wherein the non-natural thioesterase comprises alanine or threonine at the position corresponding to position 230 of SEQ ID NO: 13.

20. The host cell of claim 11, wherein the non-natural thioesterase comprises alanine or threonine at the position corresponding to position 230 of SEQ ID NO: 13.

* * * * *